United States Patent
Lakadamyali et al.

(10) Patent No.: US 10,564,167 B2
(45) Date of Patent: Feb. 18, 2020

(54) METHOD FOR DETECTING CELLS

(71) Applicants: FUNDACIÓ INSTITUT DE CIÈNCIES FOTÒNIQUES, Castelldefels-Barcelona (ES); FUNDACIÓ CENTRE DE REGULACIÓ GENÒMICA, Barcelona (ES); INSTITUCIÓ CATALANA DE RECERCA I ESTUDIS AVANçATS, Barcelona (ES)

(72) Inventors: Melike Lakadamyali, Castelldefels-Barcelona (ES); Carlo Manzo, Castelldefels-Barcelona (ES); Maria Aurelia Ricci, Barcelona (ES); Maria Pia Cosma, Barcelona (ES)

(73) Assignees: FUNDACIÓ INSTITUT DE CIÈNCIES FOTÓNEQUES, Castelldefels-Barcelona (ES); FUNDACIÓ CENTRE DE REGULACIÓ GENÒMICA, Barcelona (ES); INSTITUCIÓ CATALANA DE RECERCA↑ESTUDIS AVANçATS, Barcelona (ES)

( * ) Notice: Subject to any disclaimer, the term of this patent is extended or adjusted under 35 U.S.C. 154(b) by 149 days.

(21) Appl. No.: 15/510,082

(22) PCT Filed: Sep. 10, 2015

(86) PCT No.: PCT/EP2015/070734
§ 371 (c)(1),
(2) Date: Mar. 9, 2017

(87) PCT Pub. No.: WO2016/038145
PCT Pub. Date: Mar. 17, 2016

(65) Prior Publication Data
US 2017/0299610 A1    Oct. 19, 2017

Related U.S. Application Data

(63) Continuation-in-part of application No. 14/482,586, filed on Sep. 10, 2014, now abandoned.

(51) Int. Cl.
*C07K 16/18* (2006.01)
*G01N 33/68* (2006.01)
(Continued)

(52) U.S. Cl.
CPC ......... *G01N 33/6875* (2013.01); *C07K 16/18* (2013.01); *G01N 21/6428* (2013.01);
(Continued)

(58) Field of Classification Search
CPC ......... G01N 33/6875; G01N 33/56966; G01N 21/6428; G01N 21/6458;
(Continued)

(56) References Cited

U.S. PATENT DOCUMENTS 7,776,613 B2   8/2010  Zhuang et al.
8,084,257 B2   12/2011 Donndelinger
(Continued)

FOREIGN PATENT DOCUMENTS

EP   2378343 A2   10/2011
WO   0218418 A1   3/2002
(Continued)

OTHER PUBLICATIONS

Nela et al. Quantitative super-resolutionn microscopy: pitfalls and strategies of image analysis. Current Opinion in Chemical Biology. 20: 22-28 (Jun. 1, 2004).*
(Continued)

*Primary Examiner* — Gailene Gabel
(74) *Attorney, Agent, or Firm* — Tristan A. Fuierer; Olive Law Group, PLLC

(57) ABSTRACT

The present invention relates to methods for detecting the chromatin state of a cell based on recording a super resolution image of nucleosome organization and correlating said imaged with size of nucleosomal clutches, nucleosomal density and/or number of nucleosomes per nucleosomal clutches. Additionally, the invention relates to a kit comprising a first antibody capable of specifically binding to a histone protein and a photoswitchable fluorophore linked-secondary antibody and the use of the kit of the invention for detecting the chromatin state of a cell and isolating a cell in an open chromatin state or in a closed chromatin state. The invention also relates to a device adapted to detect the chromatin state of a cell.

15 Claims, 35 Drawing Sheets

(51) Int. Cl.
  *G01N 21/64* (2006.01)
  *G01N 33/569* (2006.01)
  *G06T 7/00* (2017.01)
(52) U.S. Cl.
  CPC ... *G01N 21/6458* (2013.01); *G01N 33/56966* (2013.01); *G06T 7/0012* (2013.01); *G01N 2021/6439* (2013.01); *G01N 2201/12* (2013.01); *G01N 2333/47* (2013.01)
(58) Field of Classification Search
  CPC ....... G01N 2021/6439; G01N 2201/12; G01N 2333/47; C07K 16/18; G06T 7/0012
  See application file for complete search history.

(56) References Cited

U.S. PATENT DOCUMENTS

| | | | |
|---|---|---|---|
| 9,137,516 | B2 | 9/2015 | Zhuang et al. |
| 2004/0197838 | A1* | 10/2004 | Allis ..................... C07K 16/18 |
| | | | 435/7.23 |
| 2010/0002929 | A1 | 1/2010 | Sammak et al. |
| 2014/0333750 | A1 | 11/2014 | Zhuang et al. |
| 2016/0305885 | A1 | 10/2016 | Panicker et al. |

FOREIGN PATENT DOCUMENTS

| | | | | |
|---|---|---|---|---|
| WO | WO 02/18418 | * | 3/2002 | ............... C07K 7/00 |
| WO | 03014142 | A2 | 2/2003 | |
| WO | 2008091296 | A2 | 7/2008 | |
| WO | 2008101249 | A1 | 8/2008 | |
| WO | 2009085218 | A1 | 7/2009 | |
| WO | 2014072960 | A2 | 5/2014 | |
| WO | 2013090360 | A2 | 6/2016 | |

OTHER PUBLICATIONS

Bates et al. Super-resolution imaging by nanoscale localization of photoswitchable fluorescent probes. Curr Opin Chem Biol. 15 (5): 505-514 (Oct. 2008).*
Wang et al. Super-resolution microscopy reveals decondensed chromatin structure at transcription sites. Scientific Reports 4 (4477) : 1-8 (Mar. 2014).*
Meshorer, et al.; Hyperdynamic plasticity of chromatin proteins in pluripotent embryonic stem cells. Developmental cell, 2006, vol. 10, pp. 105-116.
Altschul, S., et al.; BLASTManual, NCBI NLM NIH Bethesda, MD. 20894, J. Mol. Biol. vol. 215: pp. 403-410 (1990).
Dani, A., et al.; "Superresolution imaging of chemical synapses in the brain," Neuron, 2010, vol. 68, pp. 843-856.
Bock, C., et al.; "Reference Maps of human ES and iPS cell variation enable high-throughput characterization of pluripotent cell lines," Cell, 2011, vol. 144, pp. 439-452.
Bates, M., et al.; "Multicolor super-resolution imaging with photoswitchable fluorescent probes," Science, 2007, vol. 317, pp. 1749-1753.
Fan, Y., et al.; "Histone H1 depletion in mammals alters global chromatin structure but causes specific changes in gene regulation," Cell, 2005, vol. 123, pp. 1199-1212.
Bibel, M., et al.; "Generation of a defined and uniform population of CNS progenitors and neurons from mouse embryonic stem cells," Nature protocols, 2007, vol. 2, pp. 1034-1043.
Grigoryev, S.A., et al.; "Evidence for heteromorphic chromatin fibers from analysis of nucleosome interactions," Proceedings of the National Academy of Sciences of the United States of America, 2009, vol. 106, pp. 13317-13322.
Workman, Jerry L., et al.; "Nucleosome Core Displacement in Vitro via a Metastable Transcription Factor-Nucleosome Complex," Science, 1992, vol. 258, pp. 1780-1784.
Huang, B., et al.; "Whole-cell 3D Storm reveals interactions between cellular structures with nanometer-scale resolution," Nature methods, 2008, vol. 5, pp. 1047-1052.
Huang, B., et al.; "Three-dimensional super-resolution imaging by stochastic optical reconstruction microscopy," Science, 2008, vol. 319, pp. 810-813.
Marks, H., et al.; "The transcriptional and epigenomic foundations of ground state pluripotency," Cell, 2012, vol. 149, pp. 590-604.
Nieuwenhuizen, R.P., et al.; Measuring image resolution in optical nanoscopy, Nature methods, 2013, vol. 10, pp. 557-562.
Meister, Peter, et al.; "Building silent compartments at the nuclear periphery: a recurrent theme," Genetics & Development, 2013, vol. 23, pp. 96-103.
Fussner, E., et al.; "Living without 30nm chromatin fibers," Trends in biochemical sciences, 2011, vol. 36, pp. 1-6.
Fussner, E., et al.; "Constitutive heterochromatin reorganization during somatic cell reprogramming," The EMBO journal, 2011, vol. 30, pp. 1778-1789.
Kornberg, R.D., et al.; "Twenty-five years of the nucleosome, fundamental particle of the eukaryote chromosome," Cell, 1999, vol. 98, pp. 285-294.
Kühl, S.J., et al.; "On the role of Wnt/beta-catenin signaling in stem cells," Biochimica et biophysica acta, 2013, vol. 1830, pp. 2297-2306.
Ying, Q.L., et al.; "The ground state of embryonic stem cell self-renewal," Nature, 2008, vol. 453, pp. 519-523.
Rust, M.J., et al.; "Sub-diffraction-limit imaging by stochastic optical reconstruction microscopy (STORM)," Nature methods, 2006, vol. 3, pp. 793-795.
Struhl, K., et al.; "Determinants of nucleosome positioning," Nature structural & molecular biology, 2013, vol. 20, pp. 267-273.
Toth, K.F., et al.; "Trichostatin A-induced histone acetylation causes decondensation of interphase chromatin," Journal of cell science, 2004, vol. 117, pp. 4277-4287.
Woodcock, C.L., et al.; "Chromatin higher-order structure and dynamics," Cold Spring Harbor perspectives in biology, 2010, vol. 2, a000596.
Yi, F., et al.; "Tcf3 functions as a steady-state limiter of transcriptional programs of mouse embryonic stem cell self-renewal," Stem cells, 2008. vol. 26, pp. 1951-1960.
Abstract of the Seminar: Advance Fuorescence Imaging and Biophysics Group. ICFO—Institut de Ciènces Fotòniqes. Nov. 4, 2013 Departament de Fisica Fonomental.
Kamiyama, D, et al.; "Development in the Storm," Developmental Cell, 2012, vol. 23, pp. 1103-1110.
Wang, Y, et al.; "Super-resolution microscopy reveals decondensed chromatin structure at transcription sites," Scientific Reports, 2014, vol. 4, 4477, DOI: 10.1038/srep04477.
Hu, Ying, S., et al.; "Light-sheet Bayesian microscopy enables deep-cell super-resolution imaging of heterochromatin in live human embryonic stem cells," Optical Nanoscopy, 2013, vol. 7.
Pereira, Carlos F., et al.; "Heterokaryon-Based Reprogramming of Juman B Lymphocytes for Pluripotency Requires Oct4 but Not Sox2," PLOS Genetics, 2008, vol. 4, Issue 9, e1000170.

(56) References Cited

OTHER PUBLICATIONS

Durisic, et al.; "Quantitative super-resolution microscopy: pitfalls and strategies for image analysis," Current Opinion in Chemical Biology, 2014, vol. 20: pp. 22-28.
Bates, M., et al.; "Super-resolution imaging by nanoscale localization of photo-switchable fluorescent probes," Current Opinion in Chemical Biology, 2008, vol. 12, pp. 505-514.
Ricci, et al.; "Chromatin Fibers Are Formed by Heterogeneous Groups of Nucleosomes In Vivo," Cell, 2015, vol. 160, pp. 1145-1158.
International Search Report, dated Nov. 4, 2015.

* cited by examiner

C

D

E

F

C

D

D

E

B

C

Electron Microscopy 12-array

A

B

A

B

E

METHOD FOR DETECTING CELLS

CROSS-REFERENCE TO RELATED APPLICATIONS

This application is filed under the provisions of 35 U.S.C. § 371 and claims the priority of International Patent Application No. PCT/EP2015/070734 filed on 10 Sep. 2015 entitled "METHOD FOR DETECTING CELLS" in the name of Melike LAKADAMYALI, et al., which is a continuation-in-part of, and claims priority to, U.S. patent application Ser. No. 14/482,586, filed on 10 Sep. 2014, both of which are hereby incorporated by reference herein in their entirety.

TECHNICAL FIELD OF INVENTION

The present invention belongs to the field of methods for cell identification.

BACKGROUND OF INVENTION

Pluripotent stem cells have potential to differentiate into any of the three germ layers: endoderm, mesoderm, or ectoderm and provide a chance to obtain a renewable source of healthy cells and tissues to treat a wide array of diseases.

Methods currently used to detect/isolate pluripotent cells have inherent experimental variability and low efficiency, and are (1) mechanical isolation based on morphology that requires experience, and is laborious and not efficient; (2) quantification of the endogenous expression of stem cell transcription factors (OCT4, SOX2, etc.) in live cells, which requires genome modification; (3) fluorescence-activated cell sorting (FACS)-based analysis using cell surface markers (SSEA-4, TRA-1-60, etc.), which requires use of antibody based staining that is inherently variable; and (4) more recently, a pluripotent stem cell-specific adhesion signature, which is dependent on the surface properties of cell clusters and thus interrogates the population and not individual cells. Additionally, the identification of high-grade pluripotent hiPSCs is time consuming, requiring the generation of teratomas and several additional pluripotency test.

Several studies of chromosome territory occupation and genome distribution inside the nucleus show that the epigenome is dynamic and, that among other processes; it contributes to gene expression and cell differentiation.

Recent studies have revealed key differences in chromatin states of pluripotent cells as compared to differentiated cell types.

The spatial organization of chromatin inside the nucleus plays a key functional role. However, how nucleosomes are arranged to form the chromatin fiber is still highly debated.

The existence of a hierarchical organization of the chromatin fiber inside intact eukaryotic nuclei in vivo has recently been debated after cryo-electron microscopy, small-angle X-ray scattering (SAXS) and electron spectroscopic imaging experiments failed to detect the 30-nm fiber. The structural information obtained in these studies led to the overall conclusion that the eukaryotic nuclei are mainly composed of 10 nm fibers even though the core histone proteins could not be identified unequivocally using these methods due to their lack of molecular specificity. In addition, genome-wide analyses have revealed that nucleosomes are depleted at promoter and terminator regions and at many enhancers and that nucleosomes occupy preferred positions in genes and non-gene regions. Since the 30-nm fiber arrangement imposes specific constrains on nucleosome occupancy and positioning, these genome-wide analyses along with the latest imaging results argue against a hierarchical organization of nucleosomes along the chromatin fiber.

Conventional microscopy have shown that heterochromatin appears in large regions in pluripotent cells but it was confined to small foci in differentiated cells, confirming that chromatin in pluripotent cells assumes a globally more open conformation (Meshorer E. et al., 2006).

Up to date, however, the super-resolution studies of DNA and histones have not addressed questions regarding the organization of single or groups of nucleosomes, the overall nucleosome occupancy level of DNA and whether these parameters are consistent with the 30 nm fiber model of chromatin. How the chromatin organization changes at the nanoscale level as a function of cell state such as pluripotency and differentiation, while of fundamental importance, has also not been studied. In general, what has been lacking is a quantitative approach that can count and determine the number of nucleosomes within the chromatin fiber and thus identify nucleosome spatial arrangement at the nanoscale level.

Given the current debate on nucleosome occupancy, positioning and organization, and the importance of these parameters for DNA accessibility and gene expression, novel methods that allow quantitative visualization of nucleosome organization with high molecular specificity at the nanometer length scales in individual intact nuclei and leading to determine the chromatin state of a cell without the disadvantages of harsh sample preparation, lack of molecular specificity or low spatial resolution are needed.

SUMMARY OF THE INVENTION

Combining quantitative super-resolution nanoscopy with computer simulations the inventors detected a striking heterogeneity in the nucleosome organization of intact eukaryotic nuclei. Nucleosomes formed groups of varying sizes, which they term "clutches" and these were interspersed with nucleosome-depleted regions. Remarkably, the median number of nucleosomes and their compaction inside clutches highly correlated with cellular state, such that clutch size is predictive of pluripotency grade. Ground-state pluripotent stem cells had, on average, less dense clutches containing fewer nucleosomes. RNA polymerase II preferentially associated with the smallest clutches. These results provide novel insights into chromatin organization at the nanoscale level and open new possibilities for identification of stem cells through the structural organization of their chromatin fibers.

In a first aspect, the invention relates to a method for detecting the chromatin state of a cell comprising
 a) contacting a sample containing cells with a first antibody capable of specifically binding to a histone protein,
 b) contacting the antibody:histone complex formed in step a) with a secondary antibody having at least one photoswitchable fluorophore adapted to be optically excited at a certain wavelength and to emit light at a wavelength $\lambda_2$ different from $\lambda_1$,
 c) recording a super resolution image of nucleosome organization by means of a sensor being sensitive at least to the wavelength of emission of the photoswitchable fluorophore by exciting the sample with an optical radiation having a wavelength $\lambda_1$, d) correlating the image obtained in step c) with size of nucleosomal clutches, nucleosomal density and/or number of nucleosomes per nucleosomal clutches, and e) comparing data obtained in step d) with a corresponding reference value to obtain a score based on size of nucleosomal clutches, nucleosomal density and/or number of nucleosomes per nucleosomal clutch, wherein if the cell comprises smaller clutches, less densely compacted nucleosomes or less nucleosomes per clutches compared to the corresponding reference value is indicative that said cell is in an open chromatin state and wherein if the cell comprises bigger clutches, more densely compacted nucleosomes or more nucleosomes per clutches compared to the corresponding reference value is indicative that said cell is in a closed chromatin state.

In a second aspect, the invention relates to a method for isolating a cell in an open chromatin state comprising a) detecting the chromatin state of a cell by a method according to the invention, and b) isolating a cell having smaller clutches, less densely compacted nucleosomes or less nucleosomes per clutches.

In a third aspect, the invention relates to a method for isolating a cell in a closed chromatin state comprising a) detecting the chromatin state of a cell by a method according to the invention, and b) isolating a cell having bigger clutches, more densely compacted nucleosomes or more nucleosomes per clutches In a fourth aspect, the invention relates to a kit comprising a first antibody capable of specifically binding to a histone protein and a photoswitchable fluorophore linked-secondary antibody.

In a fifth aspect, the invention relates to the use of a kit of the invention for detecting and isolating a cell in an open chromatin state or in a closed chromatin state.

In a sixth aspect, the invention relates to a device adapted to detect the chromatin state of a cell comprising a source of optical radiation adapted to emit light at a wavelength $\lambda_1$ over an interrogation area adapted to receive a biological sample, an optical sensor sensible to a second wavelength $\lambda_2$ adapted to measure the optical radiation at $\lambda_2$, a control unit connected to the optical sensor and to the source of optical radiation wherein said control unit is adapted to carry out the method of the invention.

DETAILED DESCRIPTION OF THE INVENTION

Figure 1:
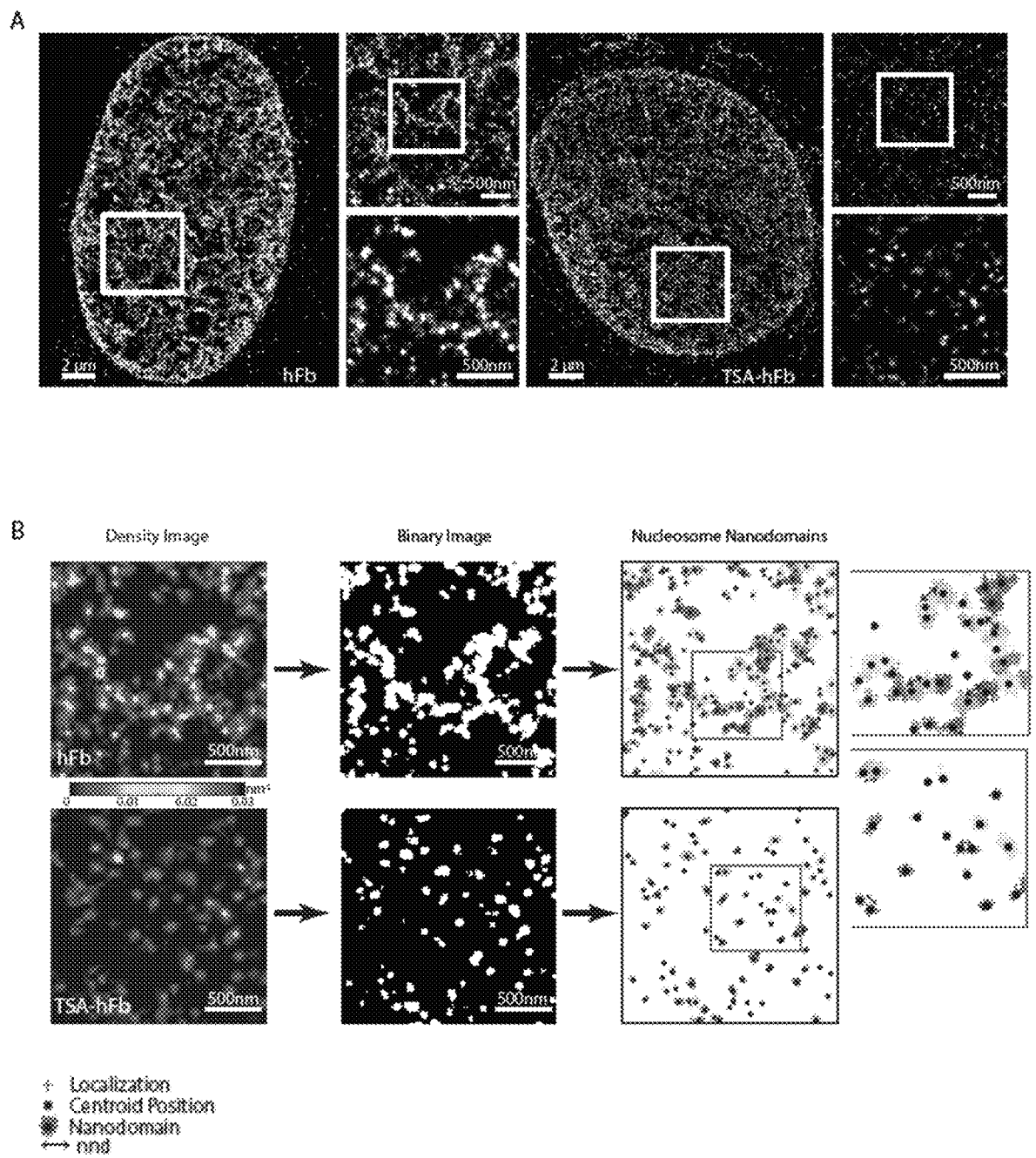
FIG. 1: Nucleosomes are arranged in discrete nanodomains in interphase nuclei of human somatic cells. (A) Super-resolution images of H2B in human fibroblast nucleus (hFb, left) and human fibroblast nucleus after treatment with trichostatin A (TSA-hFb, right). Progressively higher zooms of the regions inside the white squares are shown next to each nucleus. (B) Density images showing regions of high (light grey, spotted) and low (dark grey, background) H2B density (number of H2B localizations per unit area) in hFb (upper) and TSA-hFb (lower) according to the grey scale bar. After thresholding, the density images are converted into binary images in which regions containing H2B localizations appear white. Every white region is analyzed using a cluster identification algorithm that groups the individual localizations based on their proximity into nanodomains. Shown are example nanodomains in hFb (upper) and TSA-hFb (lower) for which localizations (crosses) having the same shade belong to the same nanodomain. The centroid position of each nanodomain is shown as a black dot. The nearest neighbor distances (nnds) between nanodomains inside the white regions are calculated (double head black arrows), along with the number of localizations per nanodomain and the nanodomain area. (C) Distribution of the number of H2B localizations per nanodomain, nanodomain area and nnds between nanodomains in hFb (dark grey) and TSA-hFb (light grey). Statistical significance between the different distributions is shown as ***($p<10^{-3}$). See also FIG. 7.
Figure 1:
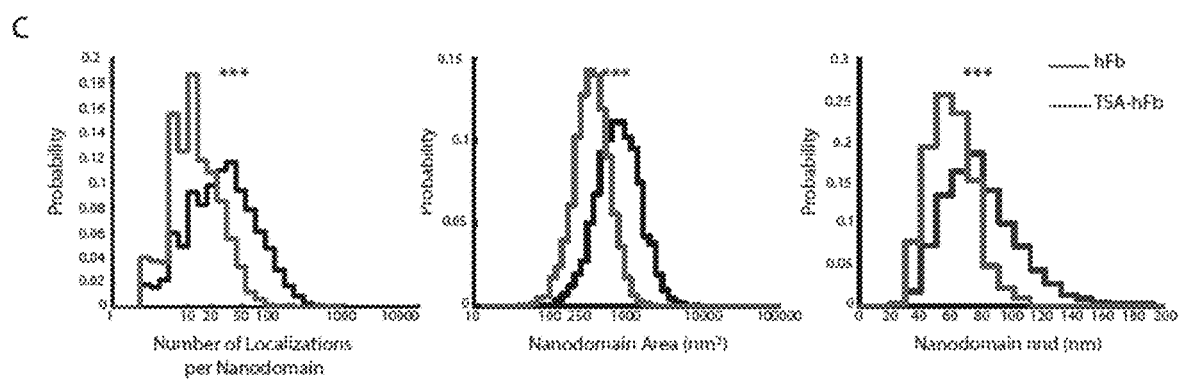

The authors of the present invention have resolved how nucleosomes are arranged along the chromatin fiber in a large number of different cell types. Their observations indicate that nucleosomes are grouped in discrete domains, which they termed "nucleosome clutches" in analogy with "egg clutches" (Example 1). They developed quantitative methods to assess clutch size, defined as the number of nucleosomes per clutch, and found that this number is very heterogeneous in a given nucleus arguing against the existence of a well-organized and ordered fiber. By comparing experimental data to computer simulations they estimated the nucleosome occupancy of the chromatin fiber and found that nucleosome-depleted regions intersperse nucleosome clutches. Two-color super-resolution imaging showed increased levels of H1 in larger clutches containing more nucleosomes suggesting that H1 might be responsible for bringing nucleosomes into closed proximity inside the clutches. On the other hand, RNA Polymerase II associated more closely with smaller clutches containing fewer nucleosomes, suggesting that the chromatin fiber within these regions is more accessible (Example 5). Strikingly, despite the heterogeneity in the clutch size in a given nucleus, on average differentiated cells contained clutches with larger number of nucleosomes compared to stem cells. Furthermore, there was a high degree of correlation between clutch size and pluripotency grade of wild-type and mutant mouse embryonic stem cells (mESC) cultured under different conditions and pluripotency grade of a number of different human induced pluripotent stem cell (hiPSC) clones. Therefore, nucleosome organization is predictive of cell pluripotency (Example 4). These results open up exciting possibilities for identifying stem cells by analyzing their nucleosome arrangement organization is predictive of cell pluripotency. Thus, the inventors have developed a method for identifying the chromatin state of a cell by analyzing their nucleosome arrangement.

Method for Detecting the Chromatin State of a Cell

According to the "textbook picture", chromatin compaction follows a hierarchical model where nucleosomes from a "beads-on-string" fiber of 10 nm in diameter, which folds into higher ordered fibers of 30 nm, which in turn compact progressively into larger fibers of 100-200 nm.

The structural information needs to be obtained using optical means having optical sensors combined with post-processing software configured to reveal internal structures having a length scale of about 10 nm.

In a first aspect, the invention relates to a method for detecting the chromatin state of a cell comprising,
  a) contacting a sample containing cells with a first antibody capable of specifically binding to a histone protein,
  b) contacting the antibody:histone complex formed in step a) with a secondary antibody having at least one photoswitchable fluorophore adapted to be optically excited at a certain wavelength and to emit light at a wavelength $\lambda_2$ different from $\lambda_1$,
  c) recording a super resolution image of nucleosome organization by means of a sensor being sensitive at least to the wavelength of emission of the photoswitchable fluorophore by exciting the sample with an optical radiation having a wavelength $\lambda_1$,
  d) correlating the image obtained in step c) with size of nucleosomal clutches, nucleosomal density and/or number of nucleosomes per nucleosomal clutches, and
  e) comparing data obtained in step d) with a corresponding reference value to obtain a score based on size of nucleosomal clutches, nucleosomal density and/or number of nucleosomes per nucleosomal clutch,
  wherein if the cell comprises smaller clutches, less densely compacted nucleosomes or less nucleosomes per clutches compared to the corresponding reference value is indicative that said cell is in an open chromatin state and wherein if the cell comprises bigger clutches, more densely compacted nucleosomes or more nucleosomes per clutches compared to the corresponding reference value is indicative that said cell is in a closed chromatin state.

Detecting, as used herein, refers both to determine and/or identify if a cell is in an open or closed chromatin state. As will be understood by those skilled in the art, the detection, although preferred to be, need not be correct for 100% of the cells to be detected or evaluated. The term, however, requires that a statistically significant portion of cells can be identified as in an open chromatin state or in a closed chromatin state. Whether a cell is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

As the skill person can understand, the method of the invention allows comparing the chromatin state between two cells, and thus it is possible to determine if two cells have a similar or different chromatin state.

"Chromatin state of a cell", as used herein relates to a condition of a cell showing open (active) chromatin or closed (inactive) chromatin. Said terms are known by a skill person. "Open chromatin" means a DNA in which histone modifications such as acetylation lead to exposure of a DNA sequence thus allowing binding of transcription factors and transcription to take place. Open chromatin is structurally loose to allow access to RNA and DNA polymerases that transcribe and replicate the DNA. "Closed chromatin" is found associated with structural proteins and include modifications of the histone tails that lead to are more tightly packaged state of the chromatin, which is less accessible to the binding of the majority of transcription factors and polymerases.

In a preferred embodiment the cell in an open chromatin state is selected from the group consisting of transcriptionally active cells, pluripotent cells, cancer cells, drug perturbed cells and reprogrammed cells. In a more preferred embodiment, the cell in an open chromatin state is a pluripotent cell. The term "transcriptionally active cell" as used herein, relates to a cell having an active chromatin, which means a DNA in which histone modifications such as acetylation lead to exposure of a DNA sequence thus allowing binding of transcription factors and transcription to take place.

"Pluripotent cell" as used herein, relates to a primordial cell that can differentiate into a sub-group of specialized types of cells, for example, a stem cell that has the potential to differentiate into any of the three germ layers: endoderm (interior stomach lining, gastrointestinal tract, the lungs), mesoderm (muscle, bone, blood, urogenital), or ectoderm (epidermal tissues and nervous system). Pluripotent stem cells can give rise to any fetal or adult cell type. However, alone they cannot develop into a fetal or adult animal because they lack the potential to contribute to extraembryonic tissue, such as the placenta. Illustrative, non-limitative examples of pluripotent cells include adipose-derived stem cells (ASCs), amniotic stem cells, bone marrow-derived stem cells (BMSCs), cord blood-derived stem cells (CB-SCs), embryonic stem cells (ESCs), fetal stem cells (FSCs), amniotic stem cells, endothelial stem cells, epidermal stem cells, haematopoietic stem and progenitor cells (HSPCs), mesenchymal stem cells (MSCs), neural stem cells (NSCx), retinal stem and progenitor cells (RSPCs), etc.

In a further embodiment, the pluripotent cell is an induced pluripotent stem cell, commonly abbreviated as iPS cell or iPSC, which is a type of pluripotent stem cell artificially derived from a non-pluripotent cell, typically an adult somatic cell, by inducing a "forced" expression of specific genes. iPSCs are similar to natural pluripotent stem cells in many respects, such as the expression of certain stem cell genes and proteins, chromatin methylation patterns, doubling time, embryoid body formation, teratoma formation, viable chimera formation, and potency and differentiability.

"Cancer cell" refers to a cell from a cancer or tumor or a cancer cell line. "Cancer" refers to a broad group of diseases involving unregulated cell growth and which are also referred to as malignant neoplasms. The term is usually applied to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. Biological processes known to be related to cancer include angiogenesis, immune cell infiltration, cell migration and metastasis. Cancers usually share some of the following characteristics: sustaining proliferative signalling, evading growth suppressors, resisting cell death, enabling replicative immortality, inducing angiogenesis, and activating invasion and eventually metastasis. Cancers invade nearby parts of the body and may also spread to more distant parts of the body through the lymphatic system or bloodstream. Cancers are classified by the type of cell that the tumour cells resemble, which is therefore presumed to be the origin of the tumour. These types include:

Carcinoma: Cancers derived from epithelial cells. This group includes many of the most common cancers, particularly in the aged, and include nearly all those developing in the breast, prostate, lung, pancreas, and colon.

Sarcoma: Cancers arising from connective tissue (i.e. bone, cartilage, fat, nerve), each of which develop from cells originating in mesenchymal cells outside the bone marrow.

Lymphoma and leukaemia: These two classes of cancer arise from hematopoietic (blood-forming) cells that leave the marrow and tend to mature in the lymph nodes and blood, respectively.

Germ cell tumour: Cancers derived from pluripotent cells, most often presenting in the testicle or the ovary (seminoma and dysgerminoma, respectively).

Blastoma: Cancers derived from immature "precursor" cells or embryonic tissue. Blastomas are more common in children than in older adults.

In a preferred embodiment the cancer cells are cells from a cancer selected from breast, ovarian, prostate, brain, pancreas, skin, bone, bone marrow, blood, thymus, uterus, testicles, hepatobiliary and liver tumors, adenoma, angiosarcoma, astrocytoma, epithelial carcinoma, germinoma, glioblastoma, glioma, hemangioendothelioma, hemangiosarcoma, hematoma, hepatoblastoma, leukaemia, lymphoma, medulloblastoma, melanoma, neuroblastoma, hepatobiliary cancer, osteosarcoma, retinoblastoma, rhabdomyosarcoma, sarcoma, and teratoma, acrallentiginous melanoma, actinic keratosis adenocarcinoma, adenoid cystic carcinoma, adenomas, adenosarcoma, adenosquamous carcinoma, astrocytictumors, bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, germ cell tumors, glioblastoma, glucagonoma, hemangioblastoma, hemangioendothelioma, hemangioma, hepatic adenoma, hepatic adenomatosis, hepatocellular carcinoma, hepatobiliary cancer, insulinoma, intraepithelial neoplasia, interepithelial squamous cell neoplasia, invasive squamous cell carcinoma, large cell carcinoma, leiomyosarcoma, melanoma, malignant melanoma, malignant mesothelialtumor, medulloblastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinoma, somatostatin-secreting tumor, squamous carcinoma, squamous cell carcinoma, undifferentiated carcinoma, uveal melanoma, verrucous carcinoma, vipoma, Wilm's tumor, intracerebral cancer, head and neck cancer, rectal cancer, astrocytoma, glioblastoma, small cell cancer, and non-small cell cancer.

"Drug perturbed cell", as used herein relates to a cell treated with a compound that target the cell machinery of transcription, the cell cycle or proliferation process. Illustrative non-limitative examples of components of the transcription machinery are RNA polymerase; specificity factors (alter the specificity of RNA polymerase for a given promoter or set of promoters, making it more or less likely to bind to them (i.e. sigma factors used in prokaryotic transcription); repressors (bind to non-coding sequences on the DNA strand that are closed to or overlapping the promoter region, impeding RNA polymerase's progress along the strand, thus impeding the expression of the gene; general transcription factors (position RNA polymerase at the start of a protein-coding sequence and then release the polymerase to transcribe the mRNA); activators (enhance the interaction between RNA polymerase and a particular promoter, encouraging the expression of the gene. Activators do this by increasing the attraction of RNA polymerase for the promoter, through interactions with subunits of the RNA polymerase or indirectly by changing the structure of the DNA); enhancers (sites on the DNA helix that are bound to by activators in order to loop the DNA bringing a specific promoter to the initiation complex); silencers (regions of DNA that are bound by transcription factors in order to silence gene expression); chromatin remodeling through specific use of miRNA molecules presents one method by which euchromatin, typically associated with transcriptional activity, is converted to heterochromatin, reducing transcription. This occurs by means of RNA induced transcriptional silencing complex or "RITS."

Illustrative non-limitative examples of such drugs are tamoxifene, bicalutamide and various types of anti-inflammatory and anabolic steroid, enzyme inhibitors such as kinase and acetylase inhibitors or activators. As a result of treatment with the drug the cell could suffer transcription of a gene.

"Reprogrammed cell" as used herein, can be referred in general to the passage of a cell from the differentiated state (or differentiated cell—i.e., a cell specialized for a specific function, such as a heart, liver, etc., that cannot generate other types of cells) to an undifferentiated state (or undifferentiated stem cell—i.e., a cell not specialized for a specific function that retains the potential to give rise to specialized cells), both at level of embryonic state or progenitor state; but also reprogramming can be referred to the passage from one differentiated state to another differentiated state (for example, a fibroblast that becomes a neuron without going back to a precursor/embryonic state, or a retinal neuron that becomes another retinal neuron without going back to a precursor/embryonic state). Reprogramming of a somatic cells can be achieved via cell fusion, via overexpression of specific transcription factors, via nuclear transfer and via the use of protein extracts. The reprogrammed cell (obtained after transcription factor overexpression, nuclear transfer or via protein extracts), the reprogrammed hybrids (formed as a result of the cell fusion between a cell, e.g. stem cell and a somatic cell) might be differentiated.

Step a) of the method for detecting the chromatin state of a cell comprises contacting a sample containing cells with a first antibody capable of specifically binding to a histone protein. Thus, according to an embodiment of the invention, an antibody:histone complex is formed contacting a sample containing cells with a first antibody capable of specifically binding to a histone protein.

"Sample", as used herein refers to any biological sample susceptible of containing cells, and it can be obtained by conventional methods known by those of average skill in the art, depending on the nature of the sample.

In a particular embodiment, said biological sample is a biopsy sample, tissue, cell or biofluid sample (plasma, serum, saliva, semen, sputum, cerebral spinal fluid (CSF), tears, mucus, sweat, milk, brain extracts and the like). Said biological samples can be obtained by any conventional method. In another aspect, the sample is a cell culture sample.

In a more preferred embodiment, the sample is a mouse or human commercial cell line. In another preferred embodiment, the sample is a biopsy sample from a human patient. In another preferred embodiment, the sample comprises primary cells purified from body parts of human donors.

As used herein, the term "antibody" refers to immunoglobulin molecules and immunologically active portions of immunoglobulin molecules, i.e., molecules containing an antigen fixing site binding specifically (immunoreacting) with an antigen, such as a protein for example. There are 5 isotypes or main classes of immunoglobulins: immunoglobulin M (IgM), immunoglobulin D (IgD), immunoglobulin G (IgG), immunoglobulin A (IgA) and immunoglobulin E (IgE).

The antibodies that are going to be used in the present invention can be, for example, polyclonal sera, hybridoma supernatants or monoclonal antibodies, antibody fragments, Fv, Fab, Fab' and F(ab')2, scFv, diabodies, triabodies, tetrabodies and humanized antibodies.

The suitable conditions for the formation of the antibody: histone complex to take place are known by the skilled in the art. If the sample containing cells contains histone proteins, then the corresponding antibody:histone complex will be formed.

"Histone protein", as used herein relates to a highly alkaline protein found in eukaryotic cell nuclei that packages and orders the DNA into structural units called nucleosomes. Five major families of histones exist: H1/H5, H2A, H2B, H3 and H4. Histones H2A, H2B, H3 and H4 are known as the core histones, while histones H1 and H5 are known as the linker histones. "Nucleosomes" are a repeating unit of the chromatin, formed by 146 base pairs (bp) of DNA wrapped around octamers of the four core histone proteins (H2A, H2B, H3 and H4).

As a person skilled in the art can know, the histone protein can also be detected by detecting a functionally equivalent variant of a histone protein.

"Functionally equivalent variant" is understood to mean all those proteins derived from a histone sequence by modification, insertion and/or deletion or one or more amino acids, whenever the function is substantially maintained.

Assays to determine the function of an enzyme are known by the skilled person and include, without limitation, initial rate assays, progress curve assays, transient kinetics assays and relaxation assays. Continuous assays of enzymatic activity include, without limitation, spectrophotometric, fluorometric, calorimetric, chemiluminiscent, light scattering and microscale thermophoresis assays. Discontinuous assays of enzymatic activity include, without limitation, radiometric and chromatographic assays. As the skilled person understands, factors that may influence enzymatic activity comprise salt concentration, temperature, pH, and substrate concentration.

The function of a histone can be determined by analyzing the compaction of DNA. The compaction of DNA can be assay using several methods known in the art, by way of illustrative-non limitative example by density gradient centrifugation on MNase digested samples, comet assay. Particularly the function of H2B can be assayed by determining the phosphorylation of H2B at serine 14, which is linked to chromatin condensation. Additionally, by way of illustrative-non limitative example, the function of the H2B can be assayed by detecting acetylation in Lys12 and in Lys15 or ubiquitylation in Lys120, all of these modifications, associated with transcriptionally activation, and thus with an open chromatin state.

Preferably, variants of a histone protein are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (v) polypeptides resulting from a histone fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

As known in the art, the "similarity" between two polypeptides is determined by comparing the amino acid sequence and the substituted amino acids preserved from a polypeptide with the sequence of a second polypeptide. The variants are defined to include polypeptide sequences different from the original sequence, preferably different from the original sequence in less than 40% of residues per segment concerned, more preferably different from the original sequence in less than 25% of residues per segment concerned, more preferably different from the original sequence in less than 10% of residues per segment concerned, more preferably different from the original sequence in only a few residues per segment concerned and, at the same time, sufficiently homologous to the original sequence to preserve functionality of the original sequence. The present invention includes amino acid sequences which are at least 60%, 65%, 70%, 72%, 74%, 76%, 78%, 80%, 90%, or 95% similar or identical to the original amino acid sequence. The degree of identity between two polypeptides may be determined using computer algorithms and methods which are widely known to those skilled in the art. The identity between two amino acid sequences is preferentially determined using BLASTP algorithm [BLASTManual, Altschul, S. et al., NCBI NLM NIH Bethesda, Md. 20894, Altschul, S., et al., J. Mol. Biol. 215: 403-410 (1990)].

In a preferred embodiment, the histone protein is core histone protein.

"Core histone protein", as used herein, refers to any histone selected from the group consisting of histone H2A, H2B, H3 and H4. In a more preferred embodiment, the core histone protein is H2B.

"H2B", as used herein, refers to one of the 5 main histone proteins involved in the structure of chromatin in eukaryotic cells. Featuring a main globular domain and a long N terminal tail H2B is involved with the structure of the nucleosomes of the 'beads on a string' structure. H2B has 19 variants in humans. The detection of any variant of H2B can be used in the present invention.

As the person skilled in the art understands it may be necessary that, after contacting the sample with the first antibody, the sample is properly collected, fixed and/or sectioned. Cells in a sample can be fixed by any suitable process including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum. In a preferred embodiment, the fixative used in the present invention is a combination of methanol and ethanol, more particularly in a 1:1 ratio.

To reduce background staining, samples can be incubated with a buffer that blocks the reactive sites to which the primary or secondary antibodies may otherwise bind. Common blocking buffers include normal serum, non-fat dry milk, BSA, or gelatin. Commercial blocking buffers with proprietary formulations are available. Methods to eliminate background staining include dilution of the primary or secondary antibodies, changing the time or temperature of incubation, or using a different primary antibody. In a preferred embodiment, the blocking is carry out by a buffer comprising BSA The detection of the antibody:histone complex (step b) is carried out by contacting said complex with a secondary antibody, having at least one photoswitchable fluorophore adapted to be optically excited at a certain wavelength and to emit light at a wavelength $\lambda_2$ different from $\lambda_1$. When the sample having the antibody:histone complex is excited with optical energy, for instance by means of a laser beam of a wavelength $\lambda_1$, those locations of the antibody:histone complex linked to the photoswitchable fluorophore emit light at the wavelength $\lambda_2$.

"Fluorophore", as used herein, refers to entities that can emit light of a certain emission wavelength when exposed to a stimulus, for example, an excitation wavelength.

"Photoswitchable" as used herein, relates to an entity which can be switched between different light-emitting or non-emitting states by incident light of different wavelengths. Typically, a "switchable" entity can be identified by one of ordinary skill in the art by determining conditions under which an entity in a first state can emit light when exposed to an excitation wavelength, switching the entity from the first state to the second state, e.g., upon exposure to light of a switching wavelength, then showing that the entity, while in the second state can no longer emit light (or emits light at a reduced intensity) or emits light at a different wavelength when exposed to the excitation wavelength. Examples of switchable entities are disclosed in WO 2008/091296. As a non-limiting example of a switchable fluorophore, Cy5 can be switched between a fluorescent and a dark state in a controlled and reversible manner by light of different wavelengths, e.g., 633 nm or 657 nm red light can switch or deactivate Cy5 to a stable dark state, while 405 nm or 532 nm light can switch or activate the Cy5 back to the fluorescent state.

In some cases, the fluorophore can be reversibly switched between the two or more states, e.g., upon exposure to the proper stimuli. For example, a first stimuli (e.g., a first wavelength of light) may be used to activate the switchable fluorophore, while a second stimuli (e.g., a second wavelength of light) may be used to deactivate the switchable fluorophore, for instance, to a non-emitting state. Any suitable method may be used to activate the fluorophore. For example, in one embodiment, incident light of a suitable wavelength may be used to activate the entity to emit light, i.e., the entity is photoswitchable. Thus, the photoswitchable fluorophore can be switched between different light-emitting or non-emitting states by incident light, e.g., of different wavelengths. The light may be monochromatic (e.g., produced using a laser) or polychromatic.

In another embodiment, the entity may be activated upon stimulation by electric field and/or magnetic field. In other embodiments, the entity may be activated upon exposure to a suitable chemical environment, e.g., by adjusting the pH, or inducing a reversible chemical reaction involving the entity, etc.

Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

In some embodiments, the switchable entity includes a first, light-emitting portion (e.g., a fluorophore), and a second portion that activates or "switches" the first portion.

Upon exposure to light, the second fluorophore may activate the first fluorophore a, causing the first fluorophore to emit light. Examples of activator fluorophores include, but are not limited to Alexa Fluor 405 (Invitrogen), Alexa 488 (Invitrogen), Cy2 (GE Healthcare), Cy3 (GE Healthcare), Cy3.5 (GE Healthcare), or Cy5 (GE Healthcare), or other suitable dyes. Examples of light-emitting portions include, but are not limited to, Cy5, Cy5.5 (GE Healthcare), or Cy7 (GE Healthcare), Alexa Fluor 647 (Invitrogen), or other suitable dyes. These may linked together, e.g., covalently, for example, directly, or through a linker, e.g., forming compounds such as, but not limited to, Cy5-Alexa Fluor 405, Cy5-Alexa Fluor 488, Cy5-Cy2, Cy5-Cy3, Cy5-Cy3.5, Cy5.5-Alexa Fluor 405, Cy5.5-Alexa Fluor 488, Cy5.5-Cy2, Cy5.5-Cy3, Cy5.5-Cy3.5, Cy7-Alexa Fluor 405, Cy7-Alexa Fluor 488, Cy7-Cy2, Cy7-Cy3, Cy7-Cy3.5, or Cy7-Cy5. In a more preferred embodiment the first fluorophore (activator) is Alexa 405 and the second fluorophore is Alexa 647.

In another preferred embodiment, wavelength $\lambda_1$ is 647 nm, wavelength $\lambda_2$ is 670 nm and wavelength $\lambda_3$ is 405 nm.

Any suitable method may be used to link the first, light-emitting fluorophore and the second, activation fluorophore. In some cases, a linker is chosen such that the distance between the first and second fluorophore is sufficiently close to allow the activator fluorophore to activate the light-emitting fluorophore as desired, e.g., whenever the light-emitting fluorophore has been deactivated in some fashion. Typically, the fluorophore will be separated by distances on the order of 500 nm or less, for example, less than about 300 nm, less than about 100 nm, less than about 50 nm, less than about 20 nm, less than about 10 nm, less than about 5 nm, less than about 2 nm, less than about 1 nm, etc. Examples of linkers include, but are not limited to, carbon chains (e.g., alkanes or alkenes), polymer units, or the like.

The switchable entity may comprise a first fluorophore directly bonded to the second fluorophore, or the first and second entity may be connected via a linker or a common entity. Whether a pair of light emitting portion and activator portion produces a suitable switchable entity can be tested by methods known to those of ordinary skills in the art. For example, light of various wavelength can be used to stimulate the pair and emission light from the light-emitting portion can be measured to determine whether the pair makes a suitable switch.

Additional details about fluorophores can be found in WO2009/085218.

Step c) of the method of the invention comprises recording a super resolution image of nucleosome organization by means of a sensor being sensitive at least to the wavelength of emission of the photoswitchable fluorophore by exciting the sample with an optical radiation having a wavelength $\lambda_1$. Recording an image by means of an optical sensor aiming to the optically excited sample provides a bitmap image at certain resolution having information about the nucleosome organization. In particular, the image shows the projection over the focal plane of the sensor used for recording the image of the location of the photoswitchable fluorophores that have emitted light. This information will be used to provide characteristic length scales and density of some relevant structural parts of the protein that allows identifying nucleosomal organization and thus the chromatin state of a cell.

"Super resolution image" as used herein, refers to an image with an axial and lateral resolution under 100 nm allowing single molecule localization. At present, super resolution images provides a resolution near the limit of the length scale defined by chromatin fibers, that is 10-30 nm.

In a preferred embodiment, the images obtained are characterized by a lateral (XY) resolution of approximately 20-30 nm and axial (Z) resolution of 50-60 nm.

The super resolution images can be obtained by any super resolution techniques known in the art. Super-resolution techniques allow the capture of images with a higher resolution than the diffraction limit. They fall into two broad categories, "true" super-resolution techniques, which capture information contained in evanescent waves, and "functional" super-resolution techniques, which use clever experimental techniques and known limitations on the matter being imaged to reconstruct a super-resolution image. There are two major groups of methods for functional super-resolution microscopy:

1. Deterministic super-resolution: The most commonly used emitters in biological microscopy, fluorophores, show a nonlinear response to excitation, and this nonlinear response can be exploited to enhance resolution. These methods include without limitation STED, GSD, RESOLFT and SSIM.

2. Stochastical super-resolution: The chemical complexity of many molecular light sources gives them a complex temporal behaviour, which can be used to make several close-by fluorophores emit light at separate times and thereby become resolvable in time. These methods include without limitation SOFI and all single-molecule localization methods (SMLM) such as SPDM, SPDMphymod, PALM, FPALM, STORM and dSTORM.

In a preferred embodiment, the super resolution image is obtained by a stochastical super resolution technique, preferably STORM, PALM and fPALM, and more preferably by STORM. STORM combines two concepts: single molecule localization and fluorophore photoswitching. The first concept allows one to localize the position of a single fluorophore with nanometer precision. Photoswitching makes it possible to "turn off" most fluorophores into a dark state and "turn on" only a small subset of them at a time. As a result, the images of the "active" fluorophores are isolated in space and their positions can be localized with high precision. Once all the fluorophores are imaged and their positions are localized, a high-resolution image can be reconstructed from these localizations. To date, the spatial resolution achieved by this technique is ~20 nm in the lateral dimensions and ~50 nm in the axial dimension. More details of STORM technology are described in WO2013090360, WO2009085218 and EP2378343.

In a preferred embodiment, a plurality of super resolution images are taken by means of a sensor being sensitive at least to the wavelength of emission of the second fluorophore $\lambda_2$ rendering a further super resolution image by collecting the sensed light emissions recorded in the plurality of images. According to said further embodiment, a plurality of images are recorded and post-processed in order to obtain a new image with the accumulated value of the optical radiation emitted by the sample. When a sample is exited with an optical radiation some of the photoswitchable fluorophores are activated and other photoswitchable fluorophores are not. The new image provides information of a large number of locations of photoswitchable fluorophores because the probability of recording the emission of light of certain photoswitchable fluorophore being excited is higher.

According to an embodiment, a pair of different photoswitchable fluorophores is used. The first photoswitchable fluorophore is adapted to be optically excited at a certain wavelength $\lambda_1$ and to emit light at a wavelength $\lambda_2$ different from $\lambda_1$; and, the second photoswitchable fluorophore is adapted to be optically excited at a wavelength $\lambda_3$ and reactivate the first fluorophore by bringing it from its dark state back to its ground state.

Thus, in a preferred embodiment of the method of the invention, the secondary antibody further comprises a second fluorophore adapted to be optically excited at a wavelength $\lambda_3$ and reactivate the first fluorophore by bringing it from its dark state back to its ground state, upon which the first fluorophore can be excited again at its excitation wavelength and emit light at its emission wavelength $\lambda_2$.

In this case, a first step the sample is excited with an optical radiation having a wavelength $\lambda_2$ turning the first fluorophore to a dark state. A further optical radiation having a wavelength $\lambda_3$ excites the second photoswitchable fluorophore which reactivates the first fluorophore by bringing it from its dark state back to its ground state, upon which the first fluorophore can be excited again at its excitation wavelength $\lambda_1$ and emit light at its emission wavelength $\lambda_2$. This last excitation using an optical radiation at a wavelength $\lambda_1$ provides the emission at an emission wavelength $\lambda_2$ that is recorded at least in one image.

In a preferred embodiment, the power of the optical radiation having a wavelength $\lambda_3$ is monotonically increased. In an example, the optical radiation at a wavelength $\lambda_3$ has been gradually increased in a sigmoidal manner reaching a maximum power value, keeping this maximum value until the fluorophores are exhaustively imaged and photobleached.

In another preferred embodiment before recording each super resolution image of the plurality of super resolution images, the sample is excited once or more times with an optical radiation having a wavelength $\lambda_1$ and subsequently excited once or more times with an optical radiation having a wavelength $\lambda_3$.

As the skill person knows, during imaging, only an optically resolvable subset of fluorophores is activated to a fluorescent state at any given moment, such that the position of each fluorophore can be determined with high precision by finding the centroid position of the single-molecule images of particular fluorophore. The fluorophore is subsequently deactivated, and another subset is activated and imaged. Iteration of this process allows numerous fluorophores to be localized and a super-resolution image to be constructed from the image data.

One fluorophore is recorded in the image by a plurality of pixels grouped in a region of the said image. The value of each pixel is associated to a certain value of radiation. The location of the fluorophore needs to be determined for the set of pixels having information of that fluorophore.

A more complex situation is found when two or more fluorophores are close enough as for a plurality of pixels show the accumulated radiation of the plurality of fluorophores. That is, the radiation value represented in a single pixel may be the contribution of the radiation from more than one fluorophore.

The individual locations of photoswitchable fluorophores and cluster information need to be identified over the image.

Step d) of the present invention, comprises correlating the image obtained in step c) with size of nucleosomal clutches, nucleosomal density and/or number of nucleosomes per nucleosomal clutches.

"Nucleosome clutch", as used herein relates to a heterogeneous nucleosome group.

"Size of nucleosomal clutches" as used herein relates to the number of nucleosomes per clutch.

"Nucleosomal density", as used herein, relates to the number of nucleosomes in a clutch divided by the unit area of that clutch.

Thus, according to the invention, the image obtained in step c) is converted to a list of "fluorescent probe positions". Several known softwares can be used for obtaining fluorescent probe positions, as illustrative non-limiting example the Insight 3 provided by BO Huang, University of California, San Francisco. Briefly, peaks in single-molecule images are identified based on a threshold and fit to a simple Gaussian to determine the x and y positions. The final images are rendered by representing each x-y position (localization) as a Gaussian with a width that corresponds to the determined localization precision (9 nm). Sample drift during acquisition is calculated and subtracted by reconstructing STORM images from subsets of frames (typically 500-1000 frames, for which drift was assumed to be small) and correlating these images to a reference frame (typically one that is reconstructed at the initial time segment). For multicolor images, each peak is color coded based on whether the emission is recorded immediately after $\lambda_3$ or another activation wavelength ($\lambda_4$). The peaks coming from a frame not belonging to the one right after an activation frame were coded as "non-specific". A crosstalk algorithm as described previously is applied to correct for non-specific activations by the imaging laser (Dani et al., 2010). Briefly, the number of "apparent specific" activations are calculated from the frame immediately following the activation pulse and the number of "non-specific" activations from subsequent imaging frames in the imaging cycle. Assuming that the probability of "non-specific" activations is constant across all frames, it could be determined the number of "actual specific" activations by subtracting the "non-specific activation" number from the "apparent specific" activation number. We then used these numbers to statistically subtract crosstalk due to "non-specific" activations in an unbiased way as previously described (Dani et al., 2010).

Additionally, the position lists can be used to construct discrete localization images, such that each pixel has a value equal to the number of localizations falling within the pixel area, as a way of illustrative-non limitative example the pixel size is ≥ the location accuracy, in a more preferred embodiment the pixel size is 10 nm. From the localization images, density maps may be obtained by 2-dimensional convolution with a square kernel, as a way of illustrative-non limitative example, preferably ≥1×1 pixels$^2$, more preferably 5×5 pixels$^2$, although the kernel can have different shapes. A constant threshold may be used to digitize the density maps into binary images, such that pixels have a value of 1 where the density is larger than the threshold value and a value of 0 elsewhere. Localizations falling on zero-valued pixels of the binary images (low-density areas) may be discarded from further analysis. Connected components of the binary image, composed by adjacent non-zero pixels (4-connected neighborhood), are sequentially singled out and analyzed. Localization coordinates within each connected component can be grouped by means of a distance-based clustering algorithm. Initialization values for the number of clusters and the relative centroid coordinates can be obtained from local maxima of the density map within the connected region, calculated by means of a peak finding routine. Localizations may be associated to clusters based on their proximity to cluster centroids. New cluster centroid coordinates can be iteratively calculated as the average of localization coordinates belonging to the same cluster. The procedure was iterated until convergence of the sum of the squared distances between localizations and the associated cluster and provided cluster centroid positions and number of localizations per cluster. Cluster sizes can be calculated as the standard deviation of localization coordinates from the relative cluster centroid.

In an embodiment, a super resolution image is rendered from the list of locations (x,y) determined as the coordinates in the sample where an optical emission of a photoswitchable fluorophore adapted to emit light at a wavelength $\lambda_2$ is present. In an example, peaks in single-molecule image are identified wherein only values over a predetermined threshold value are taken into account. The relevant values, those values over the threshold value, are fit to a simple Gaussian to determine the x and y positions over the image. The x and y position over the image can be correlated to the physical x and y coordinates over the sample for instance once the limits of the image over the sample are known. Then, the set of locations (x,y) may be provided as a list.

A further procedure uses data in a form of a list of coordinates (x, y), each coordinate (x, y) corresponding to one location of a photoswitchable fluorophore.

Departing from the information having the location (x, y) of the fluorophores obtained from the image or images, in an embodiment of the invention clutches and relevant parameters on said clutches is provided.

In a first step, a density image of resolution lower than or equal to the rendered high resolution image used for the determination of the locations (x, y) and representing the same area as said rendered high resolution image is provided wherein each pixel of the density image has a value proportional to the number of locations of the location list falling within the area represented by said pixel. In particular, the value is taken as the number of localizations falling within the pixel area represented by the pixel.

In a second step, a binary image representing the same area than the density image comprising zero value pixels if the corresponding value represented by the density image in the same location is lower than a predefined threshold; and, nonzero if said value is higher, is provided. Zero and nonzero values (for example 1), are examples of binary values representing two different levels. A first level corresponding to pixel values under the threshold value and a second level corresponding to pixel values equal or over the threshold value.

Regions of pixels corresponding to the second level comprise clutches, which are shows as clusters of pixels. A third step identifies connected regions of pixels representing values higher than the predefined threshold, that is, the binary value representing the second level.

In a fourth step, the localization of clutches is identified from the binary image and the list of localizations. For each connected region, the localization coordinates falling within said connected region is grouped according to a distance-based criterion. Each group of locations is deemed to belong to the same clutch.

The position of the clutch is taken as the centroid position of the localization coordinates associated with said clutch.

The fourth step provides a list of the position of clutches calculated as disclosed. Once the position of the clutches being in each region, the number of clutches per region, the density calculated using a distance-based criterion and other statistical values may be used as measurements parameters for the determination of criteria that allows discerning if a cell is in an open chromatin state or in a closed chromatin state according to particular embodiments of the invention.

Thus, in an embodiment, a density image of resolution lower than or equal to the rendered high resolution image and representing the same area than said rendered high resolution image is provided wherein each pixel of the density image has a value proportional to the number of locations of the list of location coordinates falling within the area represented by said pixel,
  a binary image representing the same area than the density image comprising zero value pixels if the corresponding value represented by the density image in the same location is lower than a predefined threshold; and, nonzero if said value is higher, is provided,
  identifying connected regions of pixels representing values higher than the predefined threshold,
  for each connected region, providing a list of clutch positions by grouping the localization coordinates within said connected region according to a distance-based criterion being the position of the clutch the centroid position of the localization coordinates associated with said clutch.

In a preferred embodiment, the method comprises identifying connected regions of nonzero pixels.

In a preferred embodiment, the size of nucleosomal clutch is calculated as a measure of the spreading of the positions of all the localization coordinates associated with said clutch and/or the number of nucleosomes within said clutch.

In another preferred embodiment, the density of clutches within a connected region is calculated as the number of nucleosomes per clutch divided by the area occupied by said clutches.

The method of the invention further comprises step e) comparing data obtained in step d) with a corresponding reference value to obtain a score based on size of nucleosomal clutches, nucleosomal density and/or number of nucleosomes per nucleosomal clutch.

"Reference value", as used herein relates to a laboratory value used as a reference for the values/data obtained from samples. The reference value (or reference level) can be an absolute value, a relative value, a value which has an upper and/or lower limit, a series of values, an average value, a median, a mean value, or a value expressed by reference to a control or reference value. A reference value can be based on the value obtained from an individual sample, such as, for example, a value obtained from a sample of study but obtained at a previous point in time. The reference value can be based on a high number of samples, such as the values obtained in a population of samples. In order to detect a cell in an open chromatin state, the reference value can be based on the clutches area, number of nucleosomes per nucleosomal clutch, or nucleosome density of clutches from a cell in a closed chromatin state, by way of illustrative non-limitative example from a non-cancer cell, a terminally differentiated cell or from a cell wherein the machinery of transcription is inactive.

In another preferred embodiment, the reference value can be based on the clutch area, number of nucleosomes per nucleosomal clutch or nucleosome density of clutches from cells with an open chromatin state or alternatively with a more open chromatin state, by way of illustrative, non-limitative example highly transcriptionally activated cells, highly pluripotent cell, ESCs and iPSCs. Cells with a more open chromatin state may correspond to cells with higher grade of pluripotency. The grade of pluripotency in a cell can be determined, for example, with a gene card technology (Bock et al, 2011).

In another preferred embodiment, in order to detect a cell in a closed chromatin state, the reference value is based on the clutch area, number of nucleosomes per nucleosomal clutch or nucleosome density of clutches from cell known to be in a closed chromatin state.

In a preferred embodiment, the reference value for discriminating among different cell types, based on the number of nucleosomes per clutch by way of illustrative non-limitative example is $<=5$ nucleosomes per clutch. In another preferred embodiment, the reference value for discriminating different among different cell types, based on the density of nucleosomes per clutch by way of illustrative non-limitative example is $<=0.005$ nucleosomes/nm$^2$.

Once the reference value has been established, the size of nucleosomal clutches, nucleosomal density and/or number of nucleosomes per nucleosomal clutch is compared with the reference value. As a consequence of this comparison the size of nucleosomal clutches, nucleosomal density and/or number of nucleosomes per nucleosomal clutch can be "greater than" or "bigger than" or "more that"; "less than" or "smaller than" or "equal to" the corresponding reference value.

In the context of the present invention, the size of nucleosomal clutches, the nucleosomal density or the number of nucleosomes per nucleosomal clutches are "greater than or more than or bigger than" the corresponding reference value, when the size of nuclesomal clutches, the nucleosomal density or the number of nucleosomes per nucleosomal clutches is by way of illustrative, non-limitative example, at least 1.1-fold, 1.5-fold, 2-fold, 5-fold, 10-fold, 20-fold, 30-fold, 40-fold, 50-fold, 60-fold, 70-fold, 80-fold, 90-fold, 100-fold or even more when compared with the reference value for said marker. On the other hand, the size of nucleosomal clutches, the nucleosomal density or the number of nucleosomes per nucleosomal clutches are "lower than or smaller than" the corresponding reference value, when the size of nuclesomal clutches, the nucleosomal density or the number of nucleosomes per nucleosomal decreases by way of illustrative, non-limitative example, at least 5%, 10%, 25%, 50%, 75%, or even 100%.

According to the invention, if the cell comprises smaller clutches, less densely compacted nucleosomes or less nucleosomes per clutches compared to the corresponding reference value is indicative that said cell is in an open chromatin state.

According to the invention if the cell comprises bigger clutches, more densely compacted nucleosomes or more nucleosomes per clutches compared to the corresponding reference value is indicative that said cell is in a closed chromatin state In another preferred embodiment, the method for detecting the chromatin state of a cell further comprises detecting the RNA polymerase II association to the nucleosome.

According to this aspect of the invention, if the RNA polymerase II is more associated to the nucleosome is indicative that said cell is in an open chromatin state.

"RNA polymerase II", as used herein, relates to an enzyme that catalyzes the transcription of DNA to synthesize precursors of mRNA and most snRNA and microRNA.

In a preferred embodiment, the RNA pol II subunit B1 is detected. The sequence of RNA pol II subunit B1 in humans corresponds to the sequence P24928 in the Uniprot database 3 Sep. 2014.

In another aspect, the invention further comprises detecting the linker histone H1.

"Histone H1", as used herein relates to a protein involved with the packing of the "beads on a string" sub-structures into a high order structure. The sequence of RNA H1 in humans corresponds to the sequence Q02539 in the Uniprot database 3 Sep. 2014.

According to this aspect of the invention, if the histone H1 is more associated to the nucleosome is indicative that said cell is in a closed chromatin state.

The association of RNA polymerase II or H1 to the nucleosome can be detected by any method known in the art. In a preferred embodiment, the association is detected by multicolor super resolution imaging as described in Bates et al., 2007.

Method for Isolating a Cell in an Open or Closed Chromatin State

In another aspect, the invention relates to a method for isolating a cell in an open chromatin state comprising
  a) detecting the chromatin state of a cell by a method according to the invention, and
  b) isolating a cell having smaller clutches, less densely compacted nucleosomes or less nucleosomes per clutches.

In a preferred embodiment the cell in an open chromatin state is selected from the group consisting of transcriptionally active cells, pluripotent cells, cancer cells, drug perturbed cells and reprogrammed cells. In a more preferred embodiment, the cell in an open chromatin state is a pluripotent cell. In another aspect, the invention relates to a method for isolating a cell in a closed chromatin state comprising
  a) detecting the chromatin state of the cell by a method according to the method of the invention, and
  b) isolating a cell having bigger clutches, more densely compacted nucleosomes or more nucleosomes per clutches.

All the terms and embodiments previously described are equally applicable to this aspect of the invention.

Kit of the Invention

In another aspect, the invention relates to a kit comprising a first antibody capable of specifically binding to a histone protein and a photoswitchable fluorophore linked-secondary antibody.

In the context of the present invention, "kit" is understood as a product containing the different reagents necessary for carrying out the methods of the invention packed so as to allow their transport and storage. Additionally, the kits of the invention can contain instructions for the simultaneous, sequential or separate use of the different components which are in the kit. Said instructions can be in the form of printed material or in the form of an electronic support capable of storing instructions susceptible of being read or understood, such as, for example, electronic storage media (e.g. magnetic disks, tapes), or optical media (e.g. CD-ROM, DVD), or audio materials. Additionally or alternatively, the media can contain internet addresses that provide said instruction.

In a preferred embodiment, the first antibody capable of specifically binding to a histone protein and a photoswitchable fluorophore linked-secondary antibody comprise at least 10%, at least 20%, at least 30%, at least 40%, at least 50%, at least 60%, at least 70%, at least 80%, at least 90% or at least 100% of the total amount of reagents forming the kit.

In a preferred embodiment, the histone protein is a core histone protein, more preferably histone H2B.

All the terms and embodiments previously described are equally applicable to this aspect of the invention.

Use of the Kit

In another aspect, the invention relates to the use of the kit according to the invention for detecting the chromatin state of a cell and isolating a cell in an open chromatin state or in a closed chromatin state.

In a preferred embodiment, the detection of the chromatin state of a cell and the isolation of a cell in an open chromatin state or in a closed chromatin state is performed by a method of the invention.

All the terms and embodiments previously described are equally applicable to this aspect of the invention.

Device

According to another aspect of the invention, the method of the first and second aspect of the invention may be carried out by means of a device adapted to detect the chromatin state of a cell comprising:
  a source of optical radiation adapted to emit light at a wavelength over an interrogation area adapted to receive a biological sample,
  an optical sensor sensible to a second wavelength $\lambda_2$ adapted to measure the optical radiation at $\lambda_2$,
  a control unit connected to the optical sensor and to the source of optical radiation wherein said control unit is adapted to carry out the method according to the invention.

The source of the optical radiation may be in the form of a laser source. The interrogation area is the area where the sample is located and it is the area over which the optical sensor is aiming so that the image taken by the optical sensor is the focused over the sample. In particular, the optical sensor is sensible to the second wavelength $\lambda_2$, that is, the wavelength of the radiation emitted by the photoswitchable fluorophores linked to the antibody:histone complex determining its location.

The control unit is configured to have the control over the source of the optical radiation and the optical sensor to allow recording images of samples when the photoswitchable fluorophores are excited.

In an embodiment wherein the device further comprises a source of optical radiation adapted to emit light at a wavelength $\lambda_3$ over an interrogation area adapted to receive a biological sample, the control unit is further adapted to carry out the method of the invention.

In an embodiment, the control unit is a programmable unit and is adapted to execute a computer program. According to a further embodiment, the control unit is an ASIC unit being programmed to carry out the control over the source of the optical radiation and the optical sensor to allow recording images of samples when the photoswitchable fluorophores are excited.

In a further embodiment, the control unit is adapted to carry out a post-processing of the image for the assessment of parameters over a sample. In a preferred example, the control unit is configured to carry out steps first, second, third and fourth for the calculation of position of clutches.

It is part of the invention a computer program configured to carry out any of the disclosed methods for processing images obtaining information of clutches and the spatial distribution.

The invention will be described by way of the following examples which are to be considered as merely illustrative and not limitative of the scope of the invention.

Material and Methods

Cells.

Human fibroblasts (hFb) (BJ, Skin Fibroblast, American Type Culture Collection, ATCC® CRL-2522™) were cultured in DMEM supplemented with 10% FBS, 1× Non-essential AA, 1× GlutaMax and 1× penicillin/streptomycin. Human fibroblasts were treated with 300 nM of TSA (TricostatinA, Sigma-Aldrich) solution (TSA-hFbs) in complete growth medium for 24 hours before imaging experiments. Human fibroblasts expressing the Histone H2B-SNAP fusion protein were obtained after drug selection of nucleofected cells with the pSNAP-H2B Plasmid (N91795, New England BioLabs) using the Amaxa Human Dermal Fibroblast Nucleofector Kit (Lonza, VPD-1001).

mESCs and mESCs$^{Tcf3-/-}$ were previously described (Merrill et al., 2004). mESCs$^{H1tKO}$ were gift from Arthur I. Skoultchi (Fan et al., 2005) mESCs were cultured on gelatin in sLif medium composed by KO DMEM supplemented with 15% FBS (Hyclone), 1× Non-Essential Amino acid, 1× GlutaMax (Invitrogen), 1× penicillin/streptomycin, 1×2-mercaptoethanol and 1,000 U/mL LIF ESGRO (Chemicon). mESCs were cultured also in 2iLif medium composed by N2B27 medium supplemented with 3 µM CHIR99021, 1 µM PD0325901, 1,000 U/mL LIF and 1× penicillin/streptomycin for eight passages before imaging experiments.

mNPCs were generated by culturing mESCs as cell aggregates with 5 µM retinoic acid (RA) as previously described (Bibel et al., 2007). Neuronal progenitors cells were fixed 2 days after plating dissociated cellular aggregates.

Heterokaryons were generated fusing E14 mESCs with Human Fibroblasts (BJ) (1:1 ratio) using polyethylene glycol ((w/v) PEG 50%) as previously described (Pereira et al., 2008). Mouse and human specific surface markers were used to label the cells to FACS-sort heterokaryons using a BD FACSAna Cell sorter. Finally the sorted heterokaryons were plated on gelatin coated 8-well Lab-tek 1 coverglass chamber (Nunc) and cultured in the sLif Medium. Attached heterokaryons were fixed 7 hours and 24 hours after fusion with Methanol-Ethanol solution (50:50) for 6 minutes at −20° C. 1:200 Lamin A/C antibody (VPL550, Vector Laboratories) incubation was done at room temperature for 2 hours, followed by Alexa Fluor-488 (Invitrogen) secondary antibody incubation for 40 min at room temperature. Histone H2B labeling for STORM Imaging was done as explained in details in the 'Immuno-staining for STORM' section.

In-Vitro Polynucleosome Arrays.

The regular 12-mer and 24-mer DNA templates (gift from S. Grigoryev, (Grigoryev et al., 2009)) were isolated from *Escherichia Coli* and reconstituted with native histone octamers from HeLa cells using the 'In vitro Chromatin Assembly Kit' (CA-vitro-003, DIAGENODE). Chromatin was purified over a column of 4% agarose beads (cat #: A-1040-M, ABT, Agarose Bead Technologies) in a 0.5×20 cm Econo-Column (BioRad) and immediately used for experiments. To induce high compact folding before STORM imaging, the purified polynucleosomes were spotted on a coverglass and incubated over night at 4° C. in presence of 1 mM MgCl2 and 150 mM NaCl, then fixed with PFA 4% solution for 10 min at 4° C.

Mononucleosomes were reconstituted as described before (Workman and Kingston, 1992). Briefly, naked 200 bp DNA was mixed with HeLa octamers in a 1:1 w/w ratio in a reconstitution mix with 10 mM Tris-HCl, pH 8, 20 mM EDTA, 2M NaCl, 10 mM DTT, 2 mM 2-mercaptoethanol, 15 ng/µl BSA and left in mini dialysis chamber in a floater for dialysis in a high salt concentrated buffer for 2 h at 4° C. Then the samples were dialyzed over 20 h at 4° C. continuously diluting the concentration of NaCl from 2M to 0M. Mononucleosomes were collected from the mini dialysis chamber and centrifuged. Then they were spotted on a coverglass and left at 4° C. overnight and finally fixed in PFA 4% for 10 minutes at 4° C. HeLa's octamers were spotted on a coverglass and fixed in the same way after overnight incubation at 4° C. without addition of salts.

12-polynucleosome arrays were prepared for EM according to standard protocols (CA-vitro-003, DIAGENODE). Purified and undiluted samples were applied to air glow discharged continuous carbon (hydrophilic-negatively charged surface), contrasted with Uranyl Formate and examined in a Philips Biotwin microscope at 120 kV. Images were recorded on a KeenView CCD camera (SIS Olympus) (Electron Microscopy Core Facility of European Molecular Biology Laboratory, EMBL Heidelberg).

Human Induced Pluripotent Stem Cells Generation and Characterization.

Integration-free hiPSCs were generated as described previously (Okita et al., 2011). Briefly a combination of episomal vectors encoding for OCT3/4-shp53, SOX2, KLF4 and L-MYC (Addgene, #27077, #27078, #27080) was nucleofected in human skin. Fibroblast cells (BJ, American Type Culture Collection, ATCC® CRL-2522™) using the Amaxa Human Dermal Fibroblast Nucleofector Kit (Lonza, VPD-1001). Normal fibroblast medium (DMEM supplemented with 10% FBS, 1× GlutaMax and 1× penicillin/streptomycin) was changed every day. On day 7, the nucleofected fibroblasts were reseeded onto a monolayer of feeders cells and on day 8 the normal medium was changed to hiPSC medium (DMEM/F12, 20% KO-SR, 1× Minimum Non-Essential Amino acid, 1× GlutaMax (Invitrogen), 1× penicillin/streptomycin, 1000×2-Mercaptoethanol, supplemented with 10 ng/mL fresh basic FGF just before feeding the cells). Medium was changed every day the first week and then every 2 days. hiPSC colonies appeared ~20 days after nucleofection. 20 clones were picked and plated on human feeders adding ROCK inhibitor (Y27632) at 10 µM to the medium. After some passages cells were collected using trypsin (0.05%) and plated on matrigel coated plates. 5 different clones (#6, #8, #13, #16 and #20) were finally cultured and characterized.

hiPSC clones were plated on feeders and cultured in hiPSC medium. hiPSCs plated on matrigel were cultured with the MEF-conditioned hiPSC medium.

Alkaline Phosphatase.

The staining was carried out on cells fixed in 10% Neutral Formalin Buffer for 15 min at 4° C., and washed three times with distilled water. The samples were then incubated for 45 min at room temperature in 2 ml of the staining solution prepared as it follows: 0.005 g Naphthol AS MX-PO4 (Sigma, N5000), 0.03 g Red Violet LB salt (Sigma, F1625), 200 ml N,N-Dimethylformamide (DMF, Fischer Scientific, D1191), 25 ml of Tris-HCl (MW=157.6, pH 8.3, 0.2M), and 25 ml of distilled water. The alkaline-phosphatase-positive cells showed a red color and were visible under phase-contrast microscopy.

Immunostaining of Stem Cell Markers.

The staining was carried out on cells fixed with 4% PFA for 15 min at room temperature and permeabilized with 0.1% Triton X-100 (Sigma) in PBS for 10 min. Samples were incubated in blocking buffer containing 10% BSA (Sigma) in PBS for 1 h and then where left overnight at 4° C. with primary antibodies in solution with blocking buffer.

Primary antibodies used were: mouse monoclonal anti-Human SSEA-4 clone MC-813-70 (STEMCELL technologies) diluted 1:50; mouse monoclonal anti-Human TRA1-60 clone TRA1-60R (STEMCELL technologies) diluted 1:50, mouse monoclonal anti-Oct3/4 (Santa Cruz Biotechnologies, sc-5279) diluted 1:100, rabbit polyclonal anti-Sox2 (SIGMA, s9072) diluted 1:200; rabbit polyclonal anti-Nanog (Abcam, ab21624) diluted 1:100. For each primary antibody a respective secondary antibodies conjugated to Alexa Fluor (Invitrogen), was used for 40 min at room temperature diluted 1:1000 in blocking buffer. The cells were then counterstained with DAPI (Vector Laboratories).

Embryoid Bodies (EBs) Formation.

The cells were harvested by trypsinisation and seeded in 96 well plates with V-bottom (Corning Costar) in hiPSC medium supplemented with 10 ng/ml bFGF and 10 µM ROCK inhibitor (Y27632). 48 h later the EBs were removed from the V-bottom well plates and transferred to 10 cm2 low attachment dishes in hiPSC medium. After 24 h formed EBs were divided in three parts for in vitro differentiation to meso-endo-ecto-lineages.

For differentiation to endoderm and mesoderm, EBs were propagated for 3 more days in suspension with EB medium (KO DMEM, 10% FBS (Hyclone), 1× GlutaMax (Invitrogen), 1× penicillin/streptomycin) before being plated on gelatine coated plates in EB medium. The medium was changed every 2-3 days until 15 days when samples were fixed and processed for immuno-fluorescence staining. For mesoderm differentiation, the medium was supplied with 0.5 mM ascorbic acid. For immuno-staining, rabbit polyclonal anti-Alpha Actin-Smooth Muscle (ThermoScientific, # RB-9010), 1:100 dilution and rabbit polyclonal Anti-FOXA2 antibody (Abcam, ab40874), 1:500 dilution were used.

For differentiation to ectoderm, the EBs were propagated for 3 additional days in suspension with N2B27 media (50% Neurobasal medium, 50% DMEM/F12 media, 1× GlutaMax (Invitrogen), 1× penicillin/streptomycin) supplemented with 10 ng/mL bFGF, 20 ng/mL EGF and 1,000 U/mL LIF and then for 4 more days with the addition of 1 µM RA to the medium. Then EBs were collected, washed and dissociated by incubating with trypsin (0.25) for 10 min at room temperature, pipetting up and down. Cells were then collected and plated into matrigel-coated plates in N2B27 supplemented with 10 ng/mL bFGF and 20 ng/mL EGF. 24 h later the medium was changed to N2B27 alone and cells were maintained in culture for 20 days, until neuronal connection was seen in the dish. Cells were fixed and stained as explained in previous sections with mouse monoclonal anti-beta III Tubulin, TU-20 (Abcam, ab7751), 1:500 dilution.

Teratoma Production.

Cells were collected, resuspended in matrigel and intratesticular injected in SCID mice. After 7 weeks, formed teratomas were surgically dissected, fixed, embedded, sectioned and stained with hematoxylin and eosin.

TaqMan hPSC Scorecard Panel.

hiPSCs, previously grown for one passage on matrigel without feeders, were collected and RNA extracted with the RNeasy Mini Kit (Quiagen), according to manufacturer instructions. Total RNA was treated with DNase (Quiagen) to prevent DNA Contamination. RNA integrity was controlled by bioanalyzer instrument. High Capacity cDNA Reverse Transcription (Invitrogen) was used to prepare cDNA according to TaqMan hPSC Scorecard Panel Workflow. qRT-PCR using the TaqMan hPSC Scorecard Panel was prepared according to manufacturer instruction and run in Viia 7 Real-Time PCR System. Raw Data were analyzed using the web-based hPSC Scorecard™ Analysis Softwarev1.2, available at lifetechnologies.com/scorecardsoftware.

Immuno-Staining for STORM.

For the imaging experiments, cells were plated on 8-well Lab-tek 1 coverglass chamber (Nunc) at a seeding density of 20,000-50,000 cells per well, fixed and permeabilized with Methanol-Ethanol (1:1) solution at −20° C. for 6 min or fixed with PFA 4% in PBS for 10 min and then permeabilized with 0.1% v/v Triton X-100 (SIGMA) in PBS for 10 min at room temperature. As the distribution of H2B was independent of the fixation and permeabilization protocols, Methanol-Ethanol (1:1) was preferred to minimize the handling of the sample. After 1 h incubation at room temperature with blocking buffer containing 10% (wt/vol) BSA (Sigma) in PBS, samples were incubated overnight with the primary antibody diluted 1:50 in blocking buffer and then for 40 min with the appropriate dilution of dye-labeled secondary antibodies. Repeated washing were done at every step. Primary antibodies used for immunostaining experiments were: rabbit polyclonal anti-H2B (Abcam, abcam 1790); mouse monoclonal anti-Histone H1 Antibody, clone AE-4 (Merk Millipore, 05-457); rabbit polyclonal anti-SNAP-H2B (New England Biolabs, P9310S); mouse monoclonal anti-Histone H2B, clone 5HH2-2A8 (Merk Millipore, 05-1352); rabbit polyclonal anti-Acetyl-histone H3 (Merk Millipore, 06-599); mouse monoclonal anti-RNA Polymerase II, clone H5-phosphoserine 2 version of pol II (Covance, MMS-129R); mouse monoclonal anti-RNA Polymerase II, clone H14-phosphoserine 5 version of pol II (Covance, MMS-134R); goat anti-GFP-Alexa Fluor 647 nanobody (gift from Jonas Ries), 1:1000 dilution.

Secondary antibodies used were donkey-anti mouse and donkey-anti rabbit. Secondary antibodies were all from Jackson ImmunoResearch. For STORM imaging, the secondary antibodies were labeled in-house with different combinations of pairs of activator/reporter dyes, as previously described (Bates et al., 2007). Briefly, the dyes were purchased as NHS ester derivatives: Alexa Fluor 405 Carboxylic Acid Succinimidyl Ester (Invitrogen), Cy3 mono-Reactive Dye Pack (GE HealthCare), and Alexa Fluor 647.

Carboxylic Acid succinimidyl Ester (Invitrogen). Antibody labeling reactions were performed by incubating for 40 min at room temperature a mixture containing the secondary antibody, NaHCO3, and the appropriate pair of activator/reporter dyes diluted in DMSO. Purification of labeled antibodies was performed using NAPS Columns (GE HealthCare). The dye to antibody ratio was quantified using Nanodrop and only antibodies with a composition of 3-4 Alexa Fluor 405 and 0.9-1.2 Alexa Fluor 647 per antibody were used for imaging.

For all H2B quantification experiments, primary rabbit polyclonal anti-H2B (ab1790) and the secondary donkey anti-rabbit labeled with Alexa Fluor 405-Alexa Fluor 647 (Invitrogen) pair dyes were used after in vitro characterization using mononucleosome, 12- and 24-nucleosome array labeling.

hiPSCs grown on feeder layers were co-stained for OCt3/4 (sc-5279) and H2B (ab1790), only the cells positive for the pluripotency marker were then STORM imaged for H2B.

Storm Imaging.

STORM imaging was carried out with a commercial STORM microscope system from Nikon Instruments (NSTORM). Laser light at 647 nm was used for exciting Alexa Fluor 647 (Invitrogen) and switching it to the dark state, and laser light at 405 nm was used for reactivating the Alexa Fluor 647 (Invitrogen) fluorescence via an activator dye (Alexa Fluor 405)—facilitated manner. An imaging cycle was used in which one frame belonging to the activating light pulse (405 nm) was alternated with three frames belonging to the imaging light pulse (647 nm). Dual color imaging was performed with two sets of secondary antibodies labeled with the same reporter dye (Alexa Fluor 647) but two different activator dyes (Alexa Fluor 405 and Cy3) (Bates et al., 2007). In addition to the 405 nm laserlight, an additional imaging cycle with 561 nm laser light as the activating light pulse was used for reactivating Alexa Fluor 647 linked to the second activator dye (Cy3). The emitted light from Alexa Fluor 647 was collected by an oil immersion 100× objective with 1.49 NA, filtered by an emission filter (ET705/72m) and imaged onto an electron multiplying charge coupled device (EMCCD) (Andor Technology) camera at a frame rate of 15 ms per frame. For all single color and in vitro H2B imaging experiments, identical 'excitation—switching off—reactivation' scheme was used by gradually increasing the 405 nm laser power in a sigmoidal manner starting with 0.5 µW at frame 800 and ending with 2000 µW at frame 44800 according to Table I. Up to frame 800, the 405 nm laser power was set to zero. When the final power of 2000 µW was reached, this power was kept until the fluorophores were exhaustively imaged and photobleached. Imaging was done using a previously described imaging buffer [Cysteamine MEA (SigmaAldrich, #30070-50G), Glox Solution: 0.5 mgmL$^{-1}$ glucose oxidase, 40 mgmL$^{-1}$ catalase (all Sigma), 10% Glucose in PBS](Bates et al., 2007).

STORM Data Analysis.

STORM images were analyzed and rendered as previously described (Bates et al., 2007; Huang et al., 2008a; Huang et al., 2008b), using custom-written software (Insight3, kindly provided by Bo Huang, University of California, San Francisco). Briefly, peaks in single-molecule images were identified based on a threshold and fit to a simple Gaussian to determine the x and y positions. The final images were rendered by representing each x-y position (localization) as a Gaussian with a width that corresponds to the determined localization precision (9 nm). Sample drift during acquisition was calculated and subtracted by reconstructing STORM images from subsets of frames (typically 500-1000 frames, for which drift was assumed to be small) and correlating these images to a reference frame (typically one that is reconstructed at the initial time segment). For multicolor images, each peak was color coded based on whether the emission was recorded immediately after 405 nm or 532 nm activation cycle. The peaks coming from a frame not belonging to the one right after an activation frame were coded as "non-specific". A crosstalk algorithm as described previously was applied to correct for non-specific activations by the imaging laser (Dani et al., 2010). Briefly, the number of "apparent specific" activations were calculated from the frame immediately following the activation pulse and the number of "non-specific" activations from subsequent imaging frames in the imaging cycle. Assuming that the probability of "non-specific" activations is constant across all frames, we could then determine the number of "actual specific" activations by subtracting the "non-specific activation" number from the "apparent specific" activation number. We then used these numbers to statistically subtract crosstalk due to "non-specific" activations in an unbiased way as previously described (Dani et al., 2010).

Image Analysis and Cluster Quantification.

STORM data consisting in (x,y) localization lists were used to construct discrete localization images, such that each pixel has a value equal to the number of localizations falling within the pixel area (pixel size=10 nm). From the localization images, density maps were obtained by 2-dimensional convolution with a square kernel (5×5 pixels$^2$). A constant threshold was used to digitize the density maps into binary images, such that pixels have a value of 1 where the density is larger than the threshold value and a value of 0 elsewhere. For the determination of the threshold value, unlabeled samples were imaged. The images were analyzed as described, and digitized with increasing threshold values. For each threshold value, the ratio of nonzero to zero pixels was calculated. The threshold value (0.002 nm$^{-2}$) giving a ratio $<2\times10^{-4}$ was used for image analysis. Localizations falling on zero-valued pixels of the binary images (low-density areas) were discarded from further analysis. For our threshold setting, the number of discarded localizations typically corresponded to <5% of the total number of localization within a nuclear region.

Connected components of the binary image, composed by adjacent non-zero pixels (4-connected neighborhood), were sequentially singled out and analyzed. Localization coordinates within each connected component were grouped by means of a distance-based clustering algorithm. Initialization values for the number of clusters and the relative centroid coordinates were obtained from local maxima of the density map within the connected region, calculated by means of a peak finding routine. Localizations were associated to clusters based on their proximity to cluster centroids. New cluster centroid coordinates were iteratively calculated as the average of localization coordinates belonging to the same cluster. The procedure was iterated until convergence of the sum of the squared distances between localizations and the associated cluster and provided cluster centroid positions and number of localizations per cluster. Cluster sizes were calculated as the standard deviation of localization coordinates from the relative cluster centroid.

In order to further check the effect of the threshold on the quantification, a subset of data (hFbs, TSA-hFbs, mononucleosomes, 12- and 24-nucleosome array) was analyzed by applying different threshold values, ranging from $8.10^{-4}$ to 0.004 nm$^2$. All the investigated data showed similar linear dependence of the median number of localizations per cluster versus the threshold value.

Analyses were performed by means of custom code written in Matlab.

Simulations of Synthetic Images.

Three-dimensional nucleosomes sequences were simulated assuming nucleosomes as impenetrable spheres (r=10 nm) arranged in space according to a Gaussian chain model. Inter-nucleosomes end-to-end distances were calculated by conversion of DNA linker lengths according to worm like chain (WLC) model for a polymer with a persistence length of 150 bp.

It has been assumed that at full DNA occupancy (75% of DNA length covered by nucleosomes) nucleosomes have 146 bp DNA wrapped around them and are uniformly spaced by linker DNA fragments of 50 bp (Kornberg and Lorch, 1999).

For comparison with the experimental data, distributions of linker DNA lengths were modified on the basis of two different models. In the first model (NR-model), we considered the possibility that nucleosomes can be randomly removed with a finite probability p. The removal of a nucleosome results in increase in the DNA linker length between neighboring nucleosomes, caused by DNA unwrapping (146 bp). For this model, the DNA occupancy ($OCC_{DNA}$) depends on the nucleosome removal percentage p as:

$$OCC_{DNA} = 100\% - \left[p + (100\% - p)\frac{50 \text{ bp}}{(50 + 146) \text{ bp}}\right]. \quad \text{Equation 1}$$

In the linker length (LL) model, we assume that nucleosomes are spaced by linker-DNA lengths distributed according to a normal distribution with average length $l_{average}$, so that the DNA occupancy is a function of $l_{average}$:

$$OCC_{DNA} = \frac{l \text{ bp}}{(l + 146) \text{ bp}}. \quad \text{Equation 2}$$

Simulations were carried out for several nucleosome removal percentages (from 0 to 95%) and average linker length $l_{average}$ (from 50 bp to 3000 bp). For each parameter value, thousands of simulation were generated and analyzed.

In order to obtain synthetic STORM images of nucleosomes configuration, for each simulated nucleosome a number of localizations was randomly drawn from the distribution obtained from STORM images of mononucleosomes in vitro. To take into account the different efficiency in detecting localizations at various distances from the focal plane (z axis), the number of localizations was scaled with a z-dependent factor obtained by an independent calibration. This calibration consisted of repeatedly imaging the same sample at defined distances from the focal plane. The sample was moved by means of a piezoelectric stage. Quantification of the number of localizations versus the sample distance provided the z-dependent correction factor. Localizations were then randomly placed around the nucleosome centroid position according to a 2-d Gaussian distribution with standard deviation equal to the one obtained from STORM images of mononucleosomes in vitro.

The localization coordinates were then analyzed in the same way as the regular STORM images and the number of localization per cluster, cluster area and nearest neighbor distance were quantified.

Example 1

Figure 7:
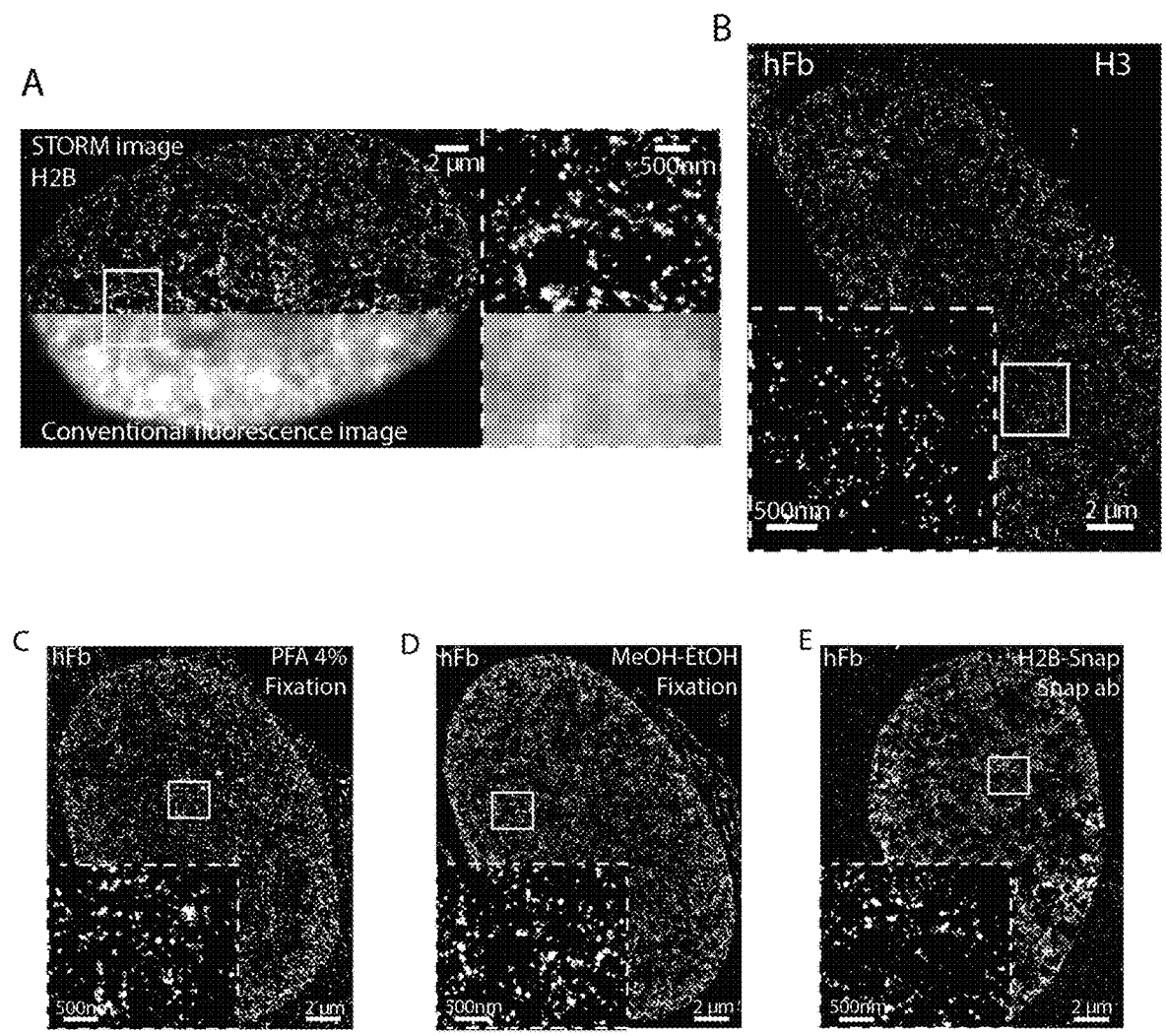
FIG. 7: Super-resolution imaging of different core histone proteins under various fixation and labeling conditions and H3 acetylation. Related to FIG. 1. (A) Comparison of super-resolution (STORM) image of H2B (upper portion) to conventional fluorescence microscopy image of H2B labeled with a primary anti-H2B antibody and Alexa Fluor 647-conjugated secondary antibody (lower portion, grey). The conventional fluorescence image was recorded with 647 nm laser at low enough laser power such that the Alexa Fluor 647 fluorophore did not switch off to the dark state. Higher zooms of the region inside the white square are shown to the right. (B) Super-resolution image of core histone protein H3. Higher zoom of the region inside the white square is shown as an inset. (C-D) Super-resolution images of H2B after fixation with 4% PFA (C), or Methanol-Ethanol (MeOH-EtOH) (D). Higher zooms of the regions inside the red squares are shown as an inset. (E) Super-resolution image of H2B in cells stably expressing H2B fused to SNAP-tag (H2B-SNAP). H2B was indirectly labeled using an anti-SNAP tag antibody. Higher zoom of the region inside the white square is shown as an inset. (F-M) Control experiment showing the labeling efficiency of H2B antibody in comparison to the GFP-nanobody. Conventional fluorescence images (grey) of GFP in nuclei transiently expressing H2B-GFP are shown for cases in which GFP-expression was low (F and J) and cases in which GFP-expression was high (H and L). These nuclei were labeled with either an antibody against H2B (G and I) or a nanobody against GFP (K and M). Corresponding super-resolution images obtained from the GFP-nanobody and H2B antibody labeling are shown next to each nucleus together with higher zooms of the regions inside the white rectangles. (N) H3 acetylation in human fibroblast cells before (hFb, left) and after treatment with trichostatin A (TSA-hFb, right). Higher zooms of the regions inside the white squares are shown as insets. (O) STORM density image showing all the localizations detected (left) and the localizations that are filtered out due to threshold (right). Low (dark grey) and high (light grey) density regions are shown according to the grey scale bar (bottom).
Figure 7:
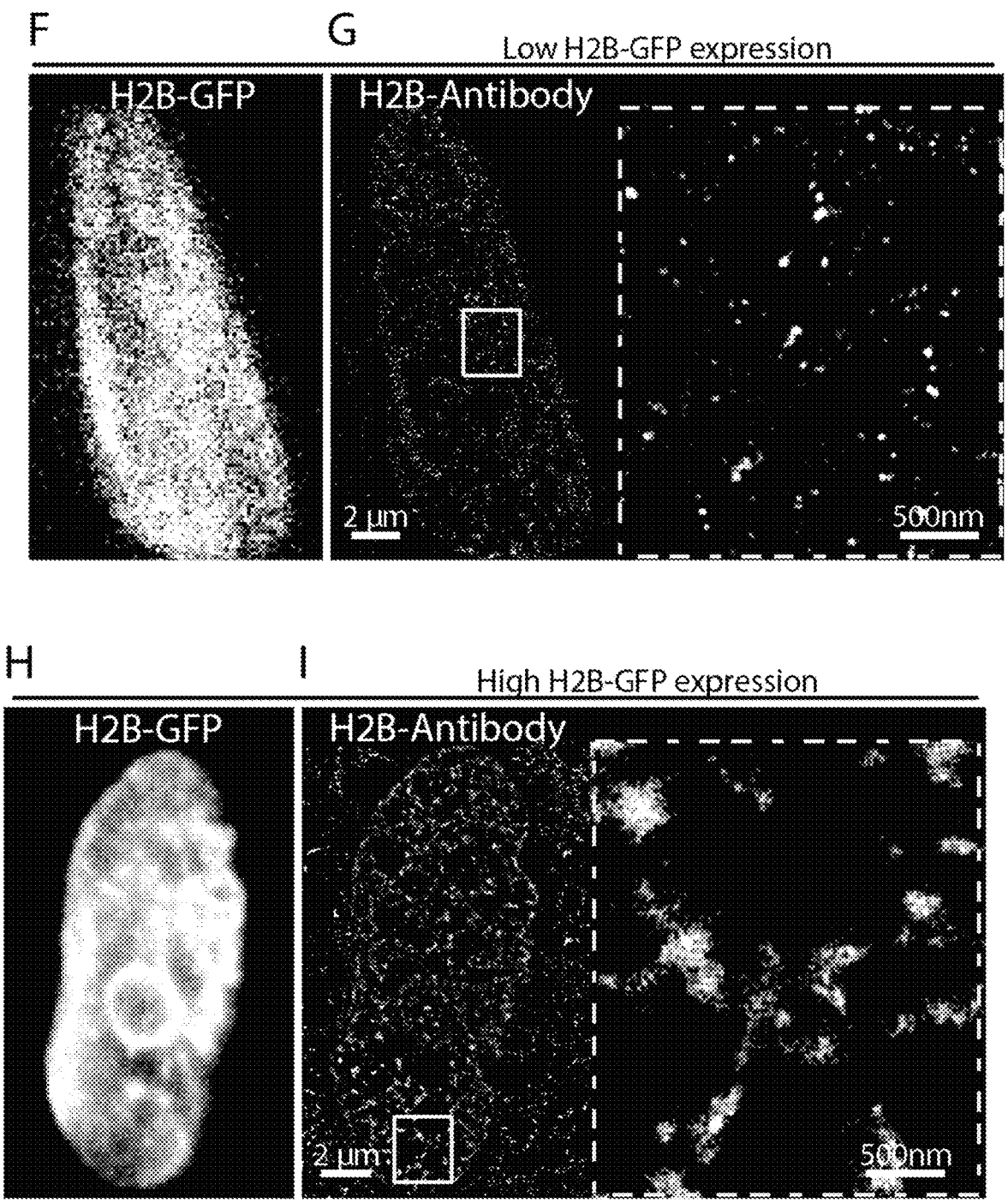
Figure 7:
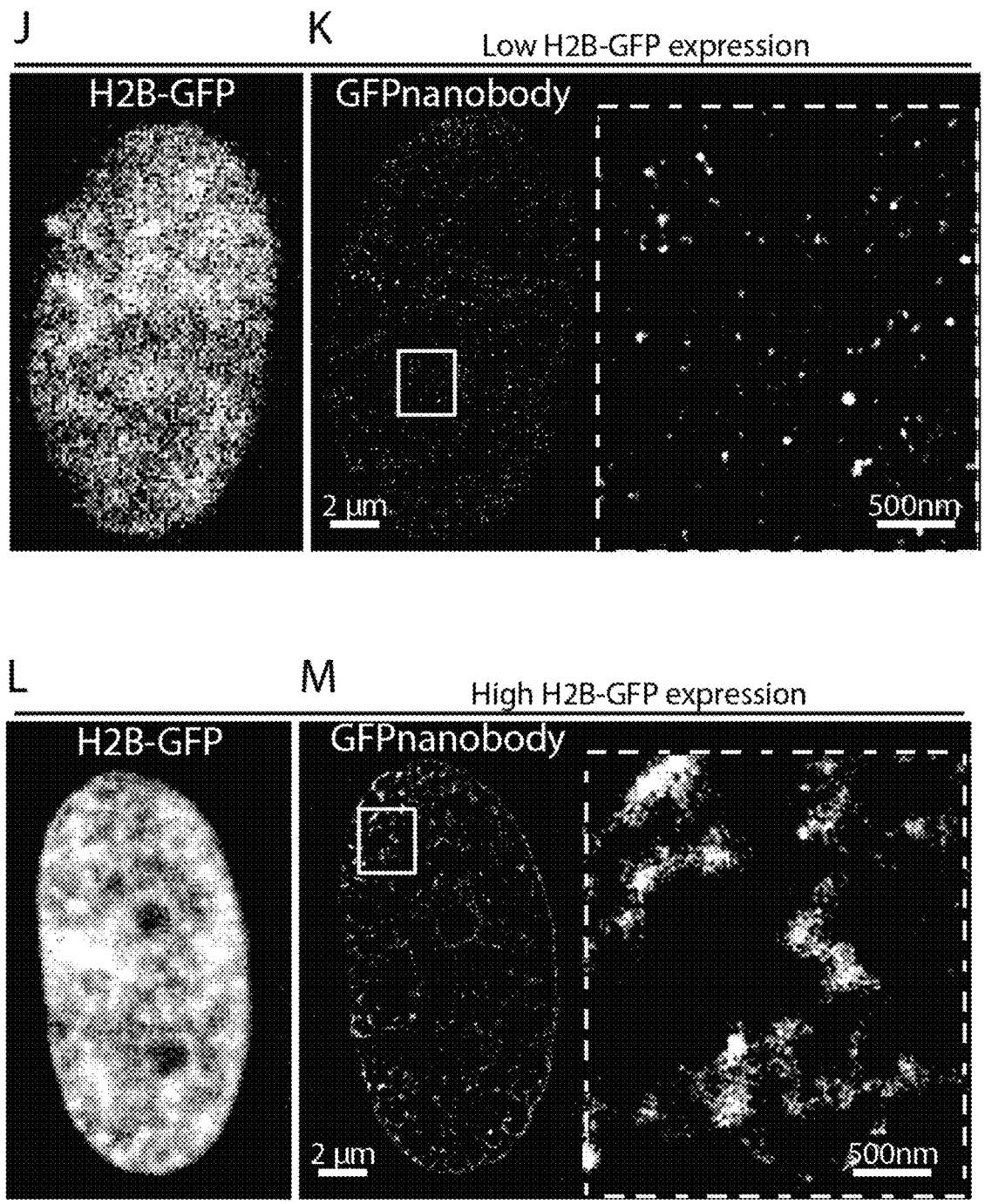
Figure 7:
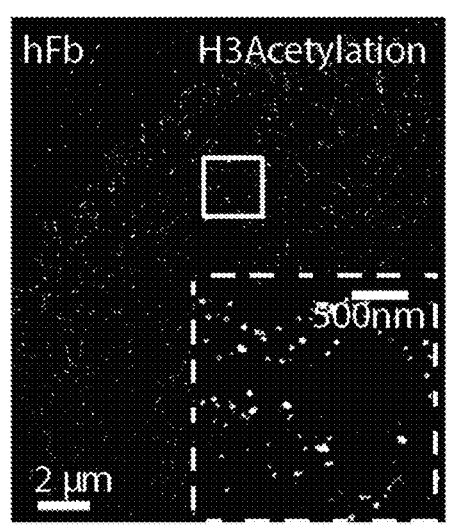
Figure 7:
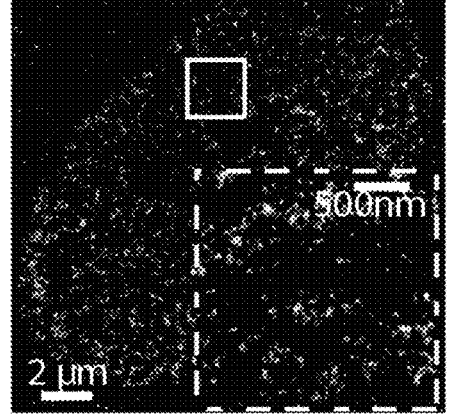
Figure 7:
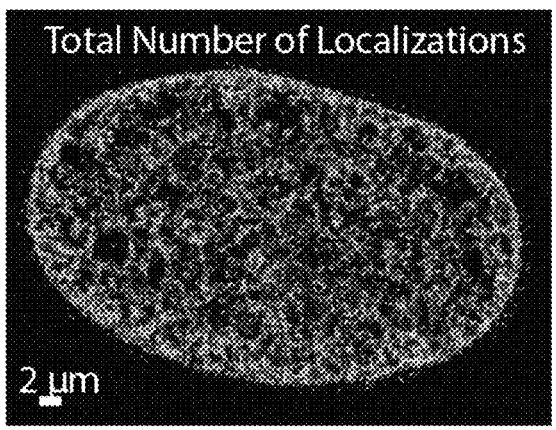
Figure 7:
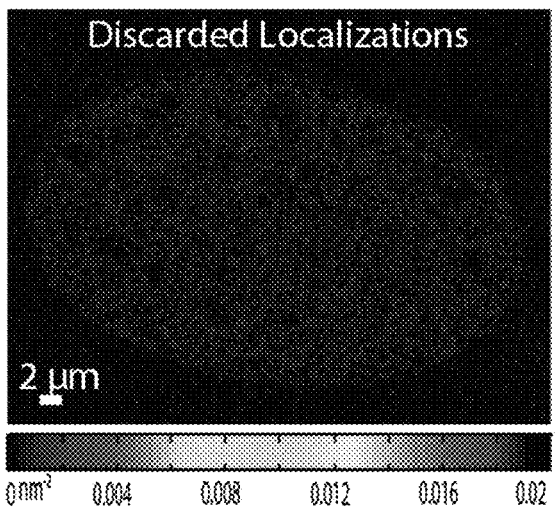

Nucleosomes in Interphase Nuclei of Human Somatic Cells are Organized in Discrete Nanodomains To reveal the organization of chromatin at nanoscale resolution, the inventors recorded STORM images of the core histone protein H2B in interphase human fibroblast nuclei (hFb). An antibody that recognizes native H2B was used. STORM images revealed a striking organization of H2B inside the nucleus (FIG. 1A, left), which was not evident with conventional fluorescence microscopy (FIG. 7A). H2B appeared clustered in discrete and spatially separated nanodomains (FIG. 1A, right zooms). The H2B nanodomain density (number of nanodomains per unit area) was ~25% higher in the nuclear periphery, where the heterochromatin is thought to be located, compared to the nuclear interior. Since H2B is a core histone of the nucleosome octamer, its localization should reflect the arrangement of nucleosomes within the chromatin fiber. In accordance with this idea, another core histone protein of the nucleosome octamer, H3, was found to be similarly clustered in discrete nanodomains (FIG. 7B).

Figure 12:
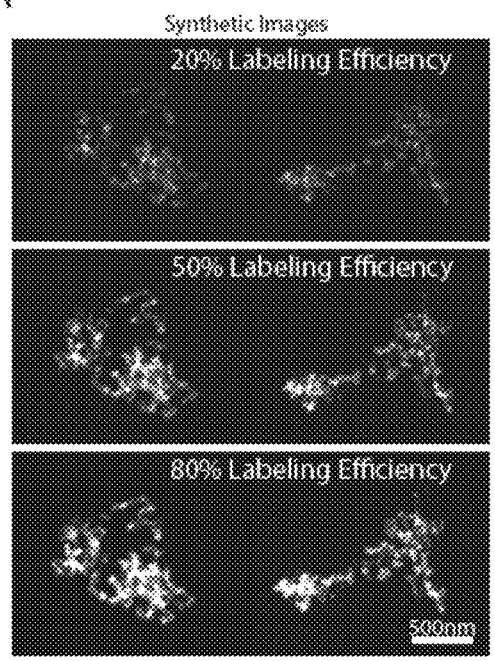
FIG. 12: Computer simulations of H2B labeling efficiency. Related to FIG. 6. (A) Example synthetic super-resolution images obtained from computer simulations of 20%, 50% and 80% H2B labeling efficiency. 100% labeling efficiency corresponds to an average of 1.6 antibodies per nucleosome as determined from in vitro images of fluorophore-labeled secondary antibodies and mononucleosomes. (B) Comparison of simulation results (black circles and black line) to experimental data for hFb (horizontal dark grey line) and hFb-TSA (horizontal lighter grey line) at different levels of antibody labeling efficiency (x-axis). The comparison is made for the number of localizations per clutch (upper), nearest neighbor distances of clutches (middle) and clutch area (lower). The vertical dark greylines show the antibody labeling efficiency values for which the simulation results intersect the experimental data for the hFb. Similarly, the vertical light grey lines show the antibody labeling efficiency values for which the simulation results intersect the experimental data for the TSA-hFb. (C-E) Comparison of the distributions for the number of localizations per clutch (C), clutch nearest neighbour distances (D) and clutch areas (E) between experimental data and occupancy simulations (57% occupancy for hFb and 45% occupancy for TSA-hFb). The distributions obtained from the experimental data are shown as darker greylines for hFb and red lines for TSA-hFb in all cases. The distributions obtained from the simulations are shown as the lighter grey lines. Statistical comparisons of experimental and simulated distributions provided a r2 of 0.95 and 0.95 (number of localizations, hFb and TSA-hFb respectively), 0.97 and 0.98 (clutch nearest neighbour distances, hFb and TSA-hFb respectively) and 0.92 and 0.97 (clutch areas, hFb and TSA-hFb, respectively).
Figure 12:
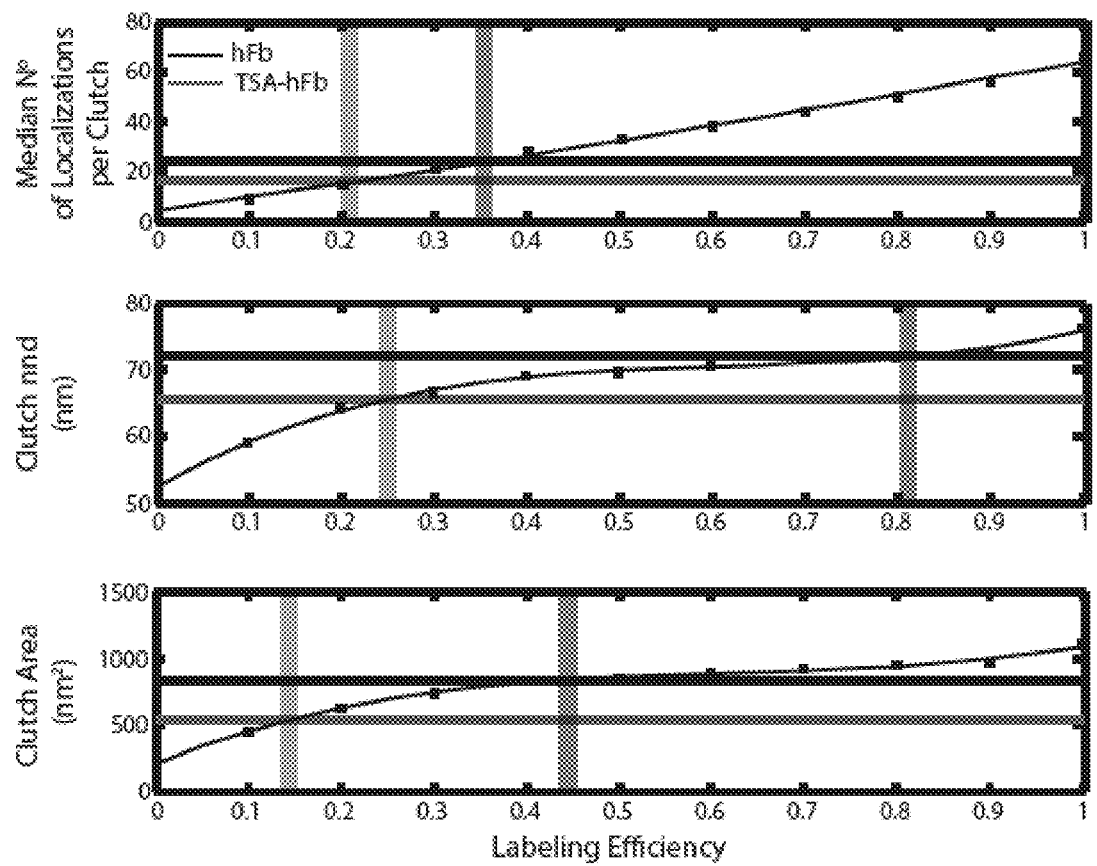
Figure 12:
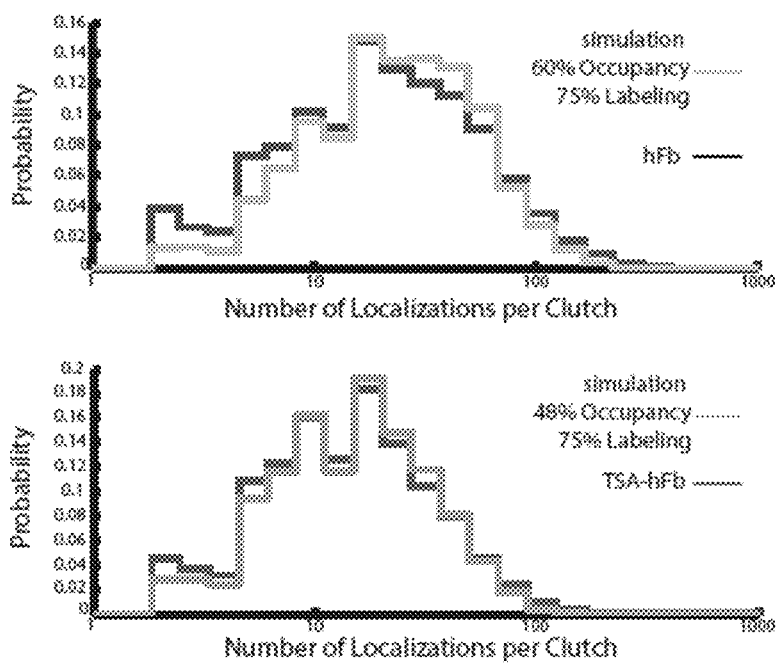
Figure 12:
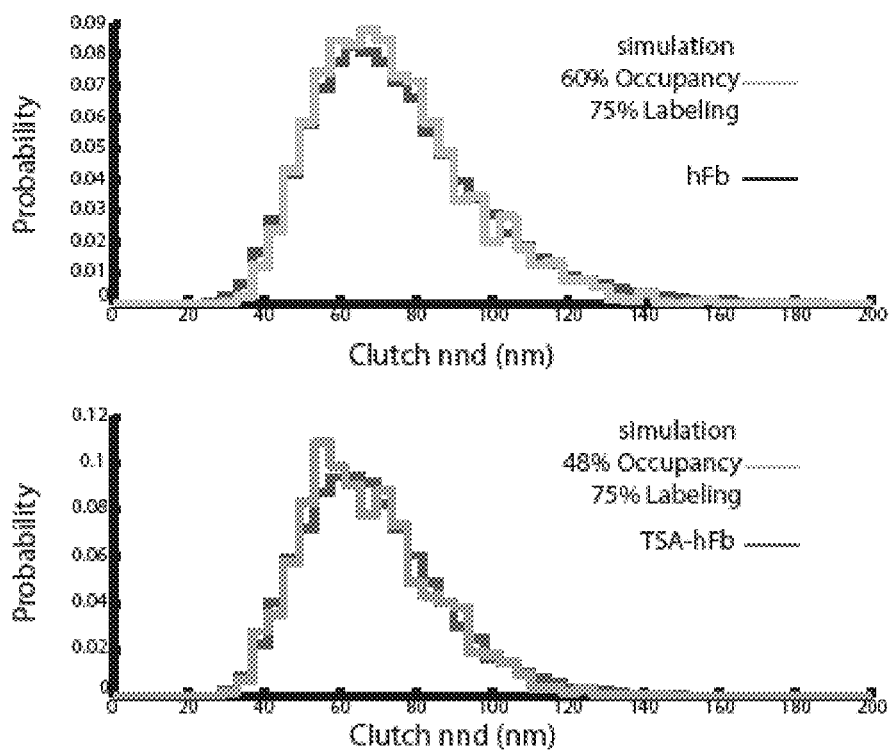
Figure 12:
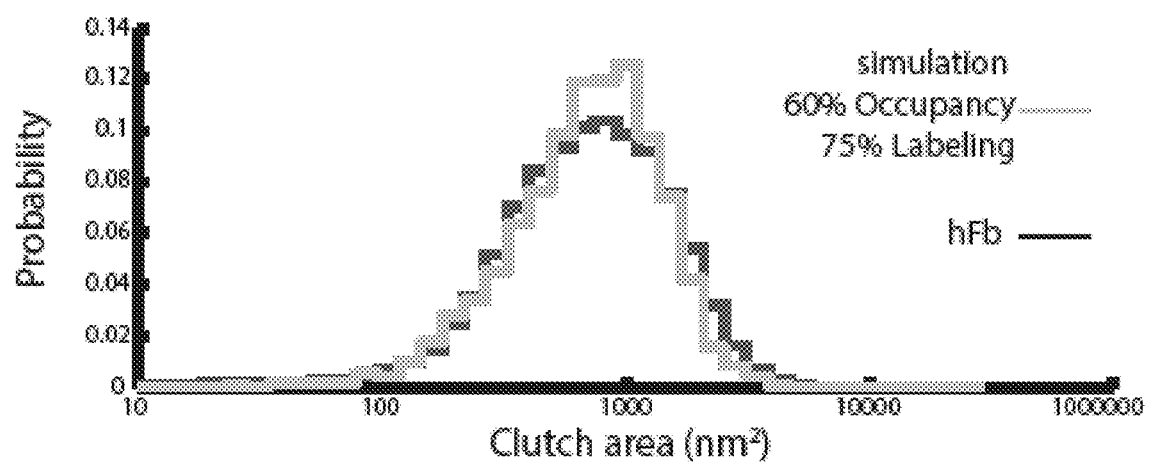
Figure 12:
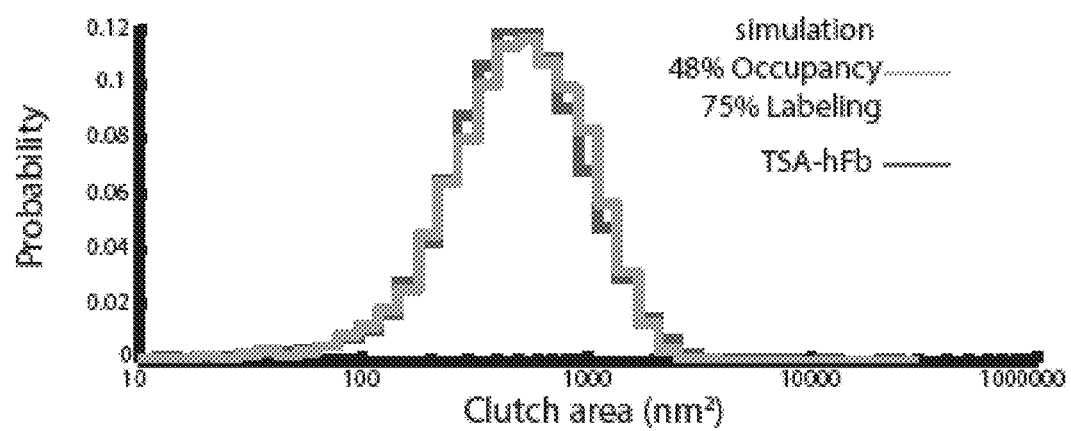

To rule out the possibility that the observed clustered distribution of H2B was due to sample preparation or labeling methods used, the inventors performed a series of control experiments. First, they showed that the clustered distribution of H2B was independent of the fixation and permeabilization protocols used (FIGS. 7C and 7D). Second, STORM images contained discrete nanodomains when H2B was indirectly labeled using an antibody against SNAP tag in cells stably expressing H2B-SNAP (FIG. 7E). Third, to rule out potential artifacts in H2B STORM images associated with the large size of the antibody probe, hFbs were transfected with a plasmid carrying H2B-GFP. hFbs showed varying levels of GFP-H2B expression as could be observed from the intensity of the GFP signal in the nucleus (FIG. 7F, H, J, L). Transfected cells were immunostained with either an anti-H2B antibody or an anti-GFP nanobody, which has a smaller size (nanobodies are 13 kDa as opposed to ~150 kDa size of the antibodies). Along with STORM images of H2B, conventional fluorescence images of GFP were recorded in these cells to assess the level of H2B-GFP expression. STORM images of low-GFP expressing cells (FIG. 7F and J) immunostained with either antibodies (FIG. 7G) or nanobodies (FIG. 7K) contained discrete nanodomains. When GFP expression level was high (FIG. 7H and L), STORM images contained much more H2B localizations (>5-fold increase) leading to a more homogenous appearance of H2B inside the nucleus with no evident organization in nanodomains, both for cells that were immunostained with antibodies and nanobodies (FIG. 7I and M). Taken together, these controls indicate that the size of the H2B-antibody does not significantly affect the detected labeling density. Finally, labeling efficiency defects were also ruled out by computer simulations of nucleosome arrangements (FIGS. 12A and 12B).

They next aimed to analyze the nucleosome organization in cells undergoing massive epigenome modifications and chromatin rearrangements. Thus, hFbs were treated with Trichostatin A (TSA) (TSA-hFb), a potent inhibitor of histone deacetylase enzyme, which is known to lead to genome-wide decondensation of chromatin inside the nucleus through accumulation of acetylation groups on histone tails (Toth et al., 2004). As expected, there was a large increase in H3 acetylation after TSA treatment (FIG. 7N). In STORM images, TSA treatment resulted in visually evident changes in the nuclear distribution of H2B nanodomains (FIG. 1A, right). The nanodomains appeared dimmer and hence contained less localizations. Furthermore, these dimmer nanodomains were also more dispersed within the nucleus (FIG. 1A, right zooms). The H2B nanodomain density was enhanced by ~10% in the nuclear periphery of TSA-hFbs compared to the nuclear interior, although it was less dense than the nuclear periphery of untreated hFbs. Finally, not only the acetylated H3 levels were increased in TSA-hFbs but also the distribution of acetylated H3 was highly dispersed in the nuclei, mirroring the spatial redistribution observed for the H2B nanodomains after TSA treatment (FIG. 7N). These changes overall indicated that nucleosomes undergo spatial rearrangement in hFb nuclei upon chromatin decondensation.

Figure 10:
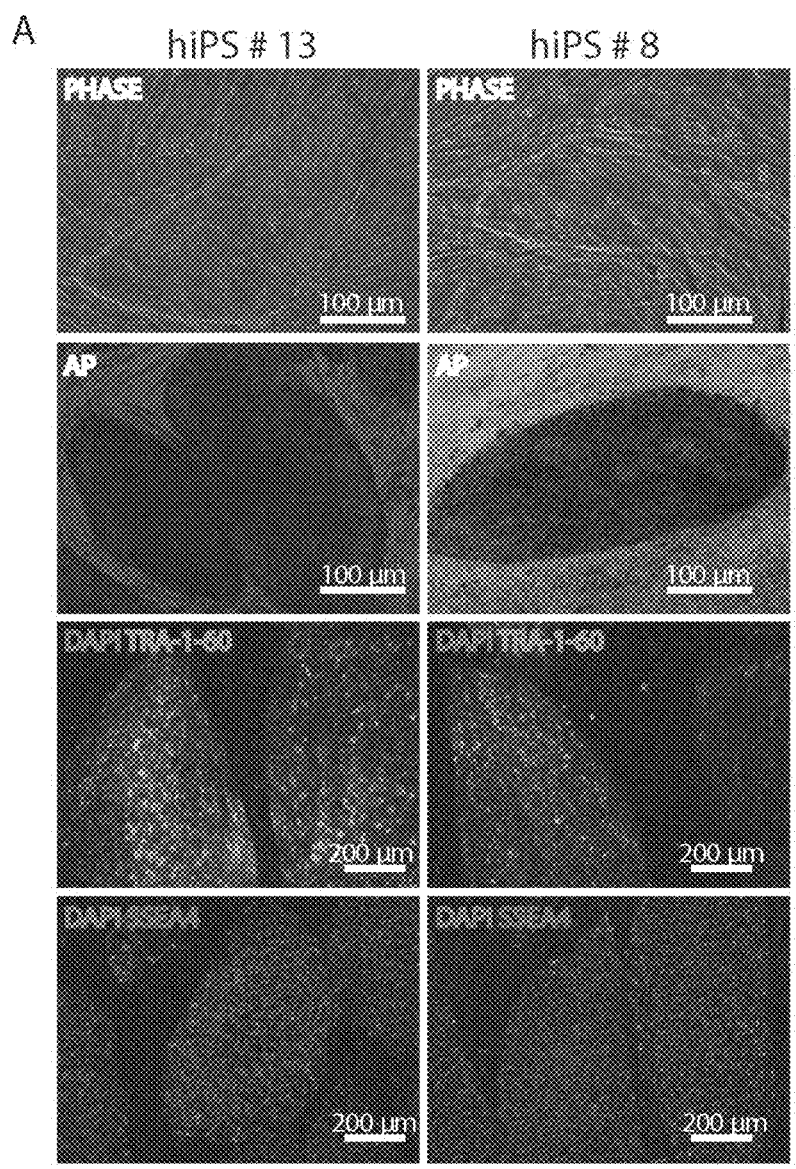
FIG. 10: Classical characterization of the human induced pluripotent stem cell (hiPSC) clone 8 and 13. Related to FIG. 4. (A-B) hiPSCs #8 and #13 were visualized by phase contrast, were stained for the expression of the stem cell marker alkaline phosphatase (AP) (A) and were visualized by conventional fluorescence microscopy after staining with antibodies against the stem cell markers TRA 1-60, SSEA4 (A), Oct4, Sox2 and Nanog (B). Conventional fluorescence microscopy using an anti-Oct4 antibody was carried out in single cells. Mean intensity of Oct4 signal in hiPSCs #8 is 144±1 (Mean intensity±SEM) and in #13 is 2063±7 (Mean intensity±SEM). Nuclei were stained with DAPI. (C) Embryoid bodies (upper panels) were formed from hiPSCs #8 and #13 and induced to differentiate in the three germ layers. Immunostaining using anti-Foxa2 (endoderm), anti-α-Sma (mesoderm) and anti-β-Tubulin III (ectoderm) were carried out 15 days after differentiation. (D) 7-weeks teratomas formed from hiPSCs #8 and #13 were weighted, sectioned and stained with hematoxylin and eosin to identify tissues derived from the three different germ layers. (E) Box plot showing the pluripotency score according to the gene card technology of all the hiPSC clones (#8 dark grey, #16 middle grey, #20 light grey black nm, #6 black and #13 light grey, no nm) analyzed. Box indicates lower (25%) and upper (75%) percentile range, the line represents the median pluripotency score and the whiskers represent minimum and maximum pluriotency scores resulting from the quantification of 67 different cells.
Figure 10:
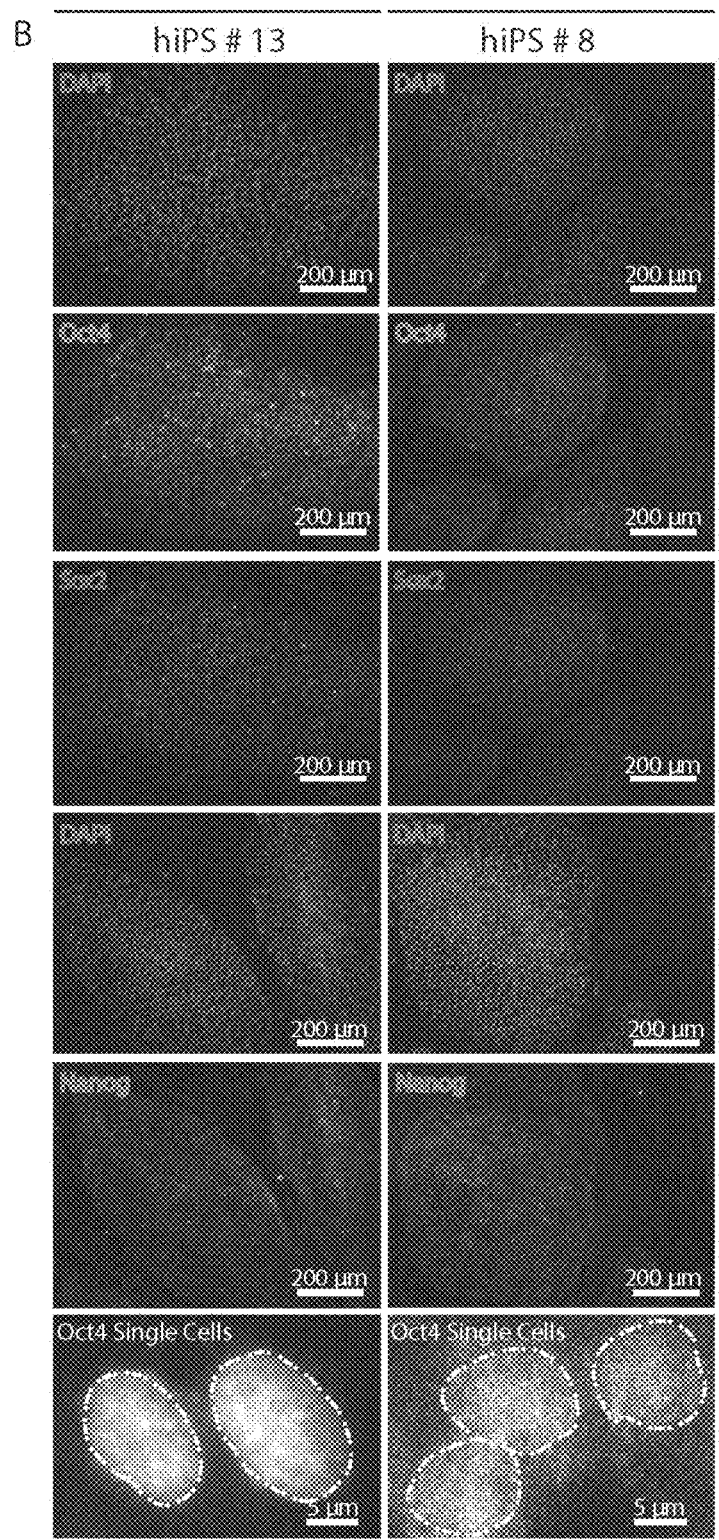
Figure 10:
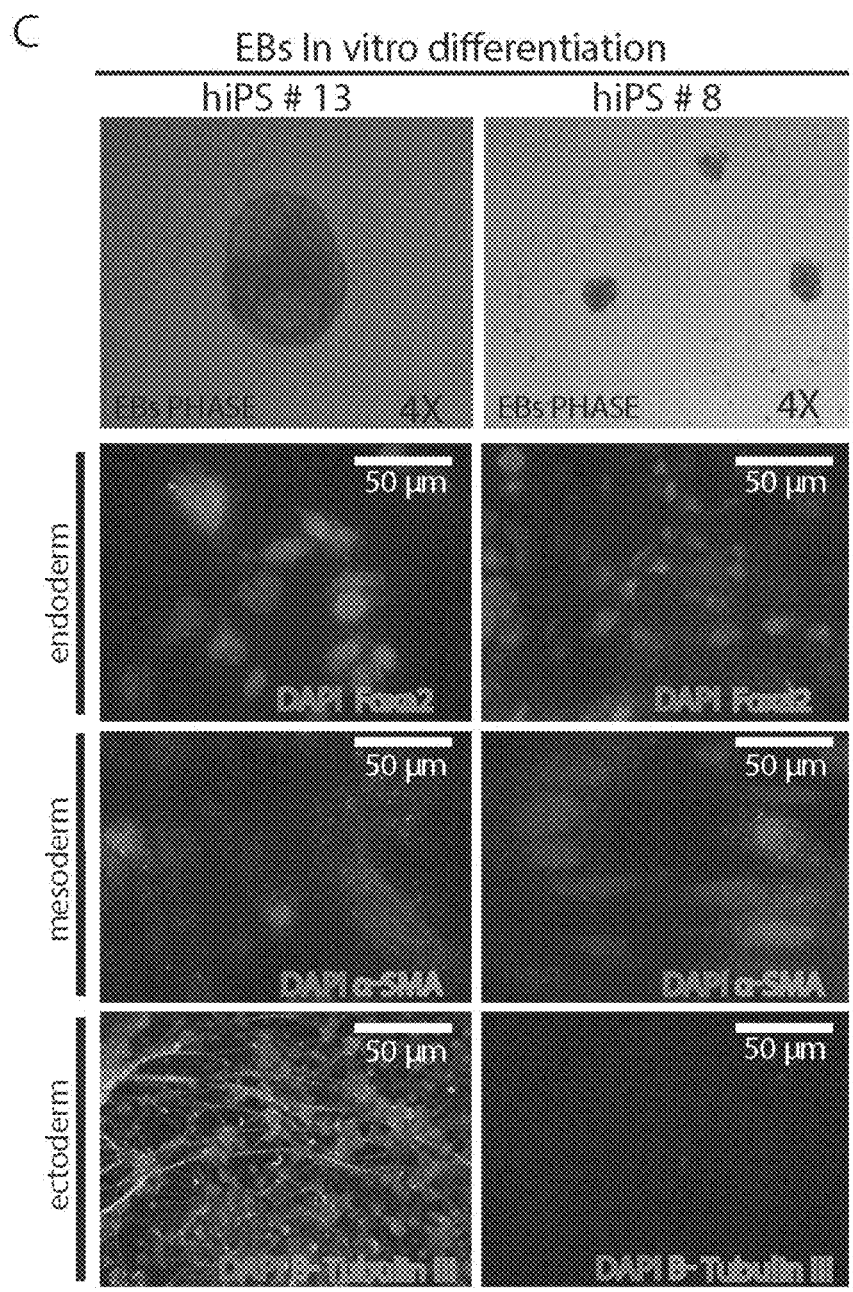
Figure 10:
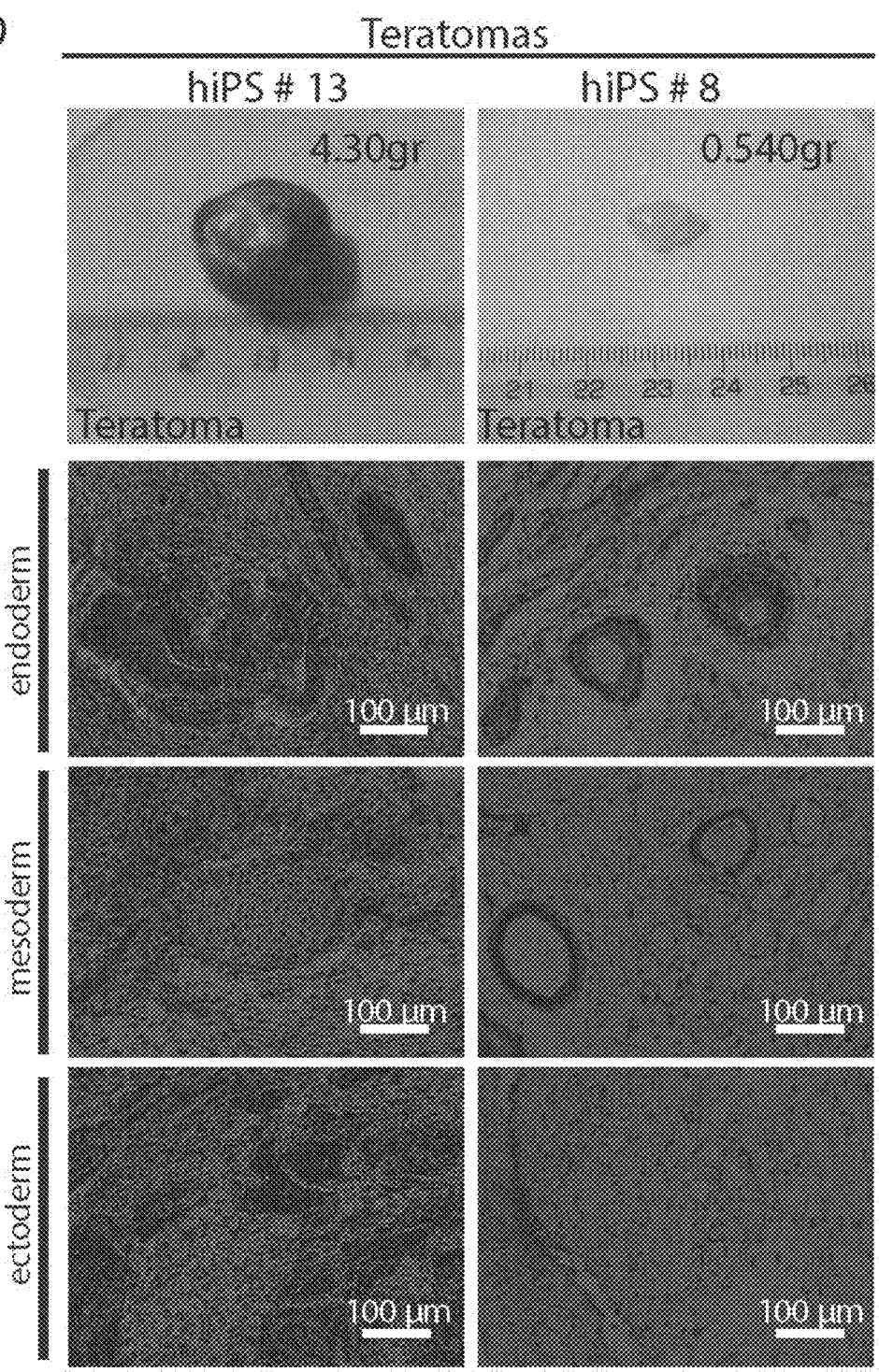
Figure 10:
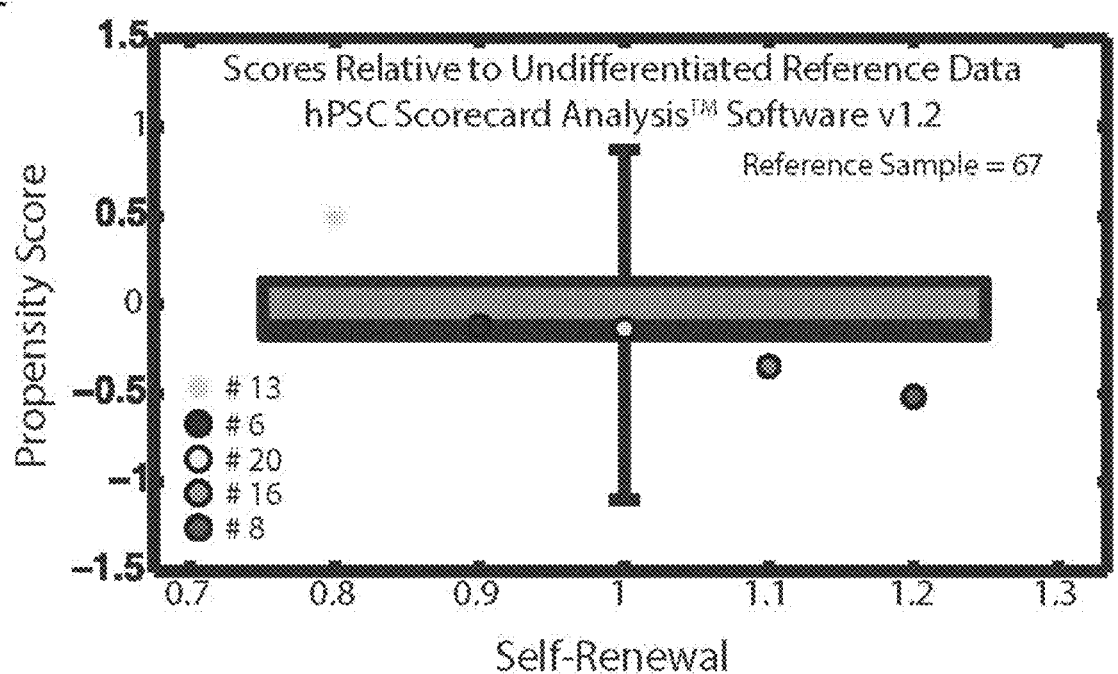

To gain quantitative insight into the H2B nanodomains, the inventors next developed a cluster identification algorithm to group the detected localizations in STORM images into nanodomains (FIG. 1B). Briefly, images were converted into a density map and a threshold was set to filter out low-density regions containing isolated localizations that were likely due to background and noise. They applied a stringent threshold setting and only <5% of the total number of localizations within a given nuclear area was discarded (FIG. 10). The remaining localizations were converted into a binary image and all the regions that contained localizations in this binary image were retained for further analysis. Within these regions a maximum likelihood algorithm was used to group the localizations together based on their spatial proximity. The number of localizations per nanodomain, nanodomain area and the nearest neighbor distances (nnd) between nanodomains were then quantified (FIG. 1C). The quantitative analysis revealed that the distributions of the number of localizations per nanodomain, nanodomain areas and nanodomain nnds were shifted to lower values in TSA-hFbs compared to hFbs (FIG. 1C). In control experiments, nanodomain areas of hFbs were similar when H2B was labeled with an antibody (Mean Area±SEM=831±66 nm2) or GFP-nanobody (Mean Area±SEM=663±23 nm2) (p=0.1347) in hFbs transfected with H2B-GFP, indicating that the large size of the antibody did not significantly affect the spatial resolution of H2B STORM images. Overall, these quantitative results confirmed that H2B nanodomains, and hence nucleosomes showed statistically significant spatial re-organization ($p<10^{-3}$) after TSA treatment and chromatin decondensation.

Example 2

Figure 2:
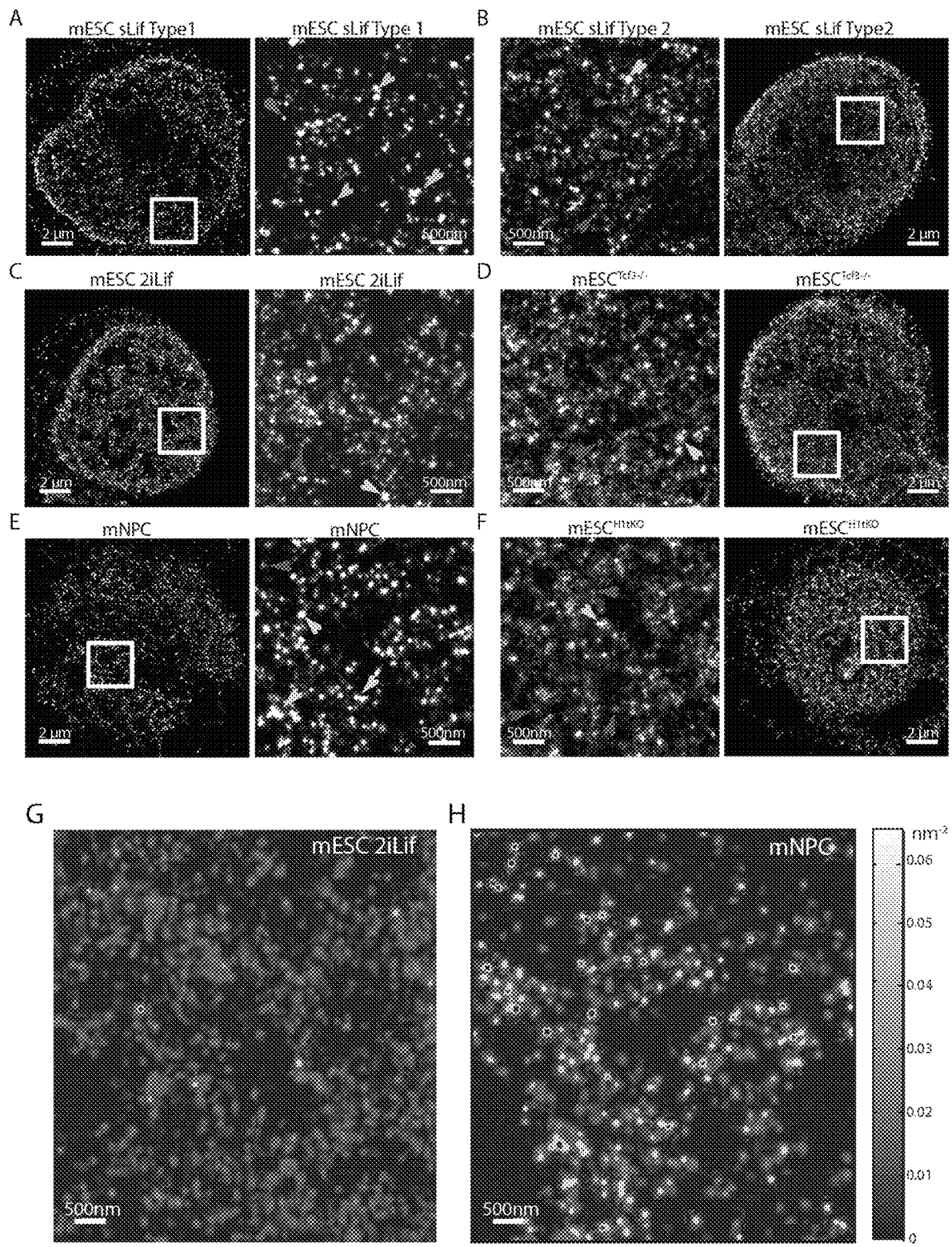
FIG. 2: Nucleosomes are arranged in discrete nanodomains in interphase nuclei of mouse embryonic stem cells. (A-F) Super-resolution images of H2B in (A) the less pluripotent (Type 1) group of mouse embryonic stem cells (mESCs) cultured in serum plus Lif (sLif) medium, (B) the more pluripotent (Type 2) group of mESCs cultured in sLif medium, (C) mESCs cultured in 2iLif medium, (D) neuronal precursor cells (mNPC) obtained after differentiation of mESCs, (E) mutant mESCs lacking Tcf3 (mESC$^{Tcf3-/-}$) and (F) mutant mESCs that are triple H1 knockout (mESC$^{H1tKO}$). Next to each cell type, higher zooms of the regions inside the white squares are shown. Light grey arrowheads point to bright nanodomains comprising a large number of localizations whereas dark grey arrowheads point to dimmer nanodomains comprising a small number of localizations. (G-H) Density image showing the differences in nanodomain organization of mESCs cultured in 2iLif medium (G) and mNPCs (H) Regions of high (light grey) and low (dark grey) H2B density are shown according grey scale bar. (I) Distribution of the number of H2B localizations per nanodomain and nanodomain nnds in mNPCs (dark grey) and mESCs cultured in 2iLif medium (light grey). Statistical significance is shown as ***($p<10^{-3}$). See also FIG. 8.
Figure 2:
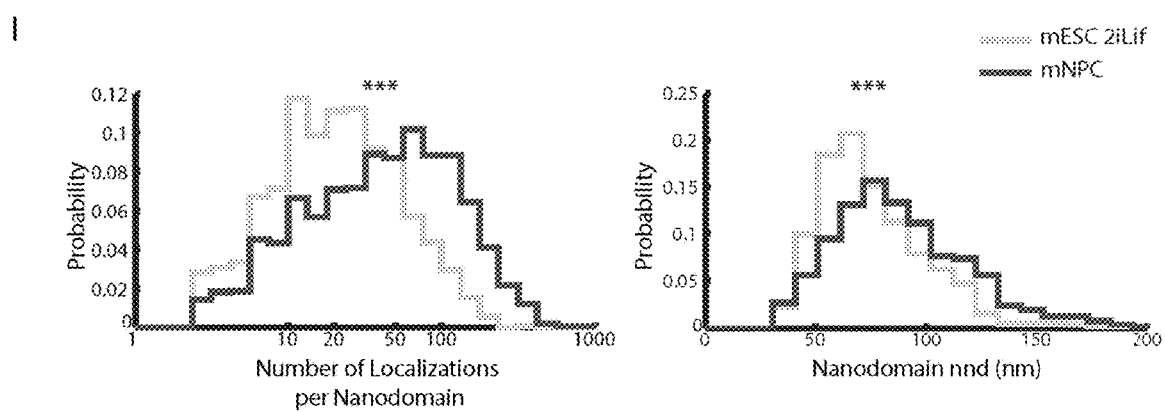

Nucleosomes in Interphase Nuclei of Mouse Embryonic Stem Cells Form Discrete Nanodomains, Whose Organization Correlates with Ground State Pluripotency To assess the H2B organization of pluripotent stem cells, the inventors next imaged mouse embryonic stem cells (mESC) with STORM. mESCs were initially cultured in a medium containing serum and the Leukemia inhibitory factor (sLif) and H2B was labeled by immunofluorescence and imaged with STORM as before. STORM images of these mESCs showed two different categories of nuclei. The first category, Type 1, displayed nanodomains that appeared bright (i.e. contained a large number of localizations) similar to hFbs (FIG. 2A, light grey arrowheads). The second category, Type 2, on the other hand, displayed an increased amount of dimmer nanodomains (i.e. containing a small number of localizations) and the nanodomains were more dispersed within the nucleus, similar to TSA-hFbs (FIG. 2B, dark grey arrowheads). It has been reported that mESCs cultured in sLif medium are heterogeneous and some cells are primed to differentiation (Marks et al., 2012). The inventors thus hypothesized that the differences in Type 1 and Type 2 mESCs could be due to different levels of pluripotency. To test this hypothesis, Nanog, a pluripotency marker, was imaged with conventional fluorescence microscopy and STORM images of H2B were recorded. As can be deduced from the density images (FIG. 8A), cells belonging to Type 1 expressed low levels of Nanog whereas those belonging to Type 2 expressed high levels of Nanog. These results are consistent with the interpretation that differences in H2B nanodomain organization of mESCs are correlated with differences in pluripotency. To further validate this observation, mESCs were next cultured in a medium containing 2i and Lif. The 2iLif medium contains inhibitors for the mitogen-activated protein kinase signaling and glycogen synthase kinase-3, which allow mESCs to be propagated in their ground-state of pluripotency. Nanodomains of mESCs cultured in the 2iLif medium were mostly dim and resembled the nanodomain organization of more pluripotent Type 2 mESCs, further confirming the correlation between pluripotency and H2B nanodomain organization (FIGS. 2C and 2G). In contrast, when mESCs were differentiated into neural precursor cells (mNPCs) the H2B nanodomains became brighter, resembling the somatic phenotype of hFbs (FIGS. 2D and 2H).

Figure 8:
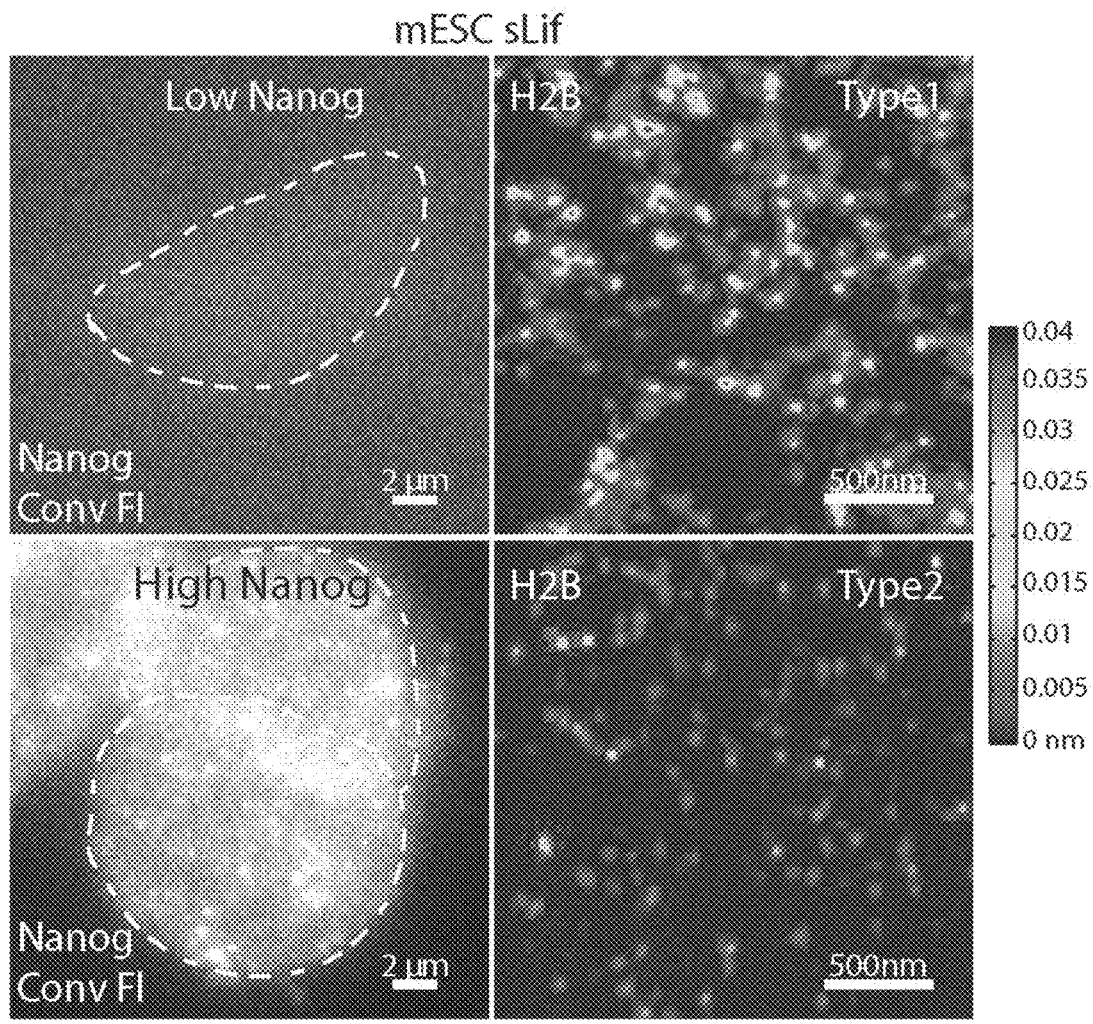
FIG. 8: Super-resolution imaging of H2B in mouse embryonic stem cells (mESCs) cultured in serum and Lif (sLif) expressing different levels of Nanog, and H3 acetylation in mESCs. Related to FIG. 2. (A) Conventional fluorescence (Cony Fl) image of Nanog (grey) labeled with a primary anti-Nanog antibody and Cy3-conjugated secondary antibody. Density images show high (light grey) and low (dark grey-black) H2B density regions in H2B super-resolution images of Type 1 (upper) and Type 2 (lower) mESCs cultured in sLif according to the grey scale bar. (B-F) Super-resolution images of H3 acetylation in mESC$^{Tcf3-/-}$ (B), mESCs cultured in sLif, Type 1 (C), mESCs cultured in 2iLif, (D), mESCs cultured in sLif, Type 2 (E), and mouse neuronal precursor cells (mNPC) (F).
Figure 8:
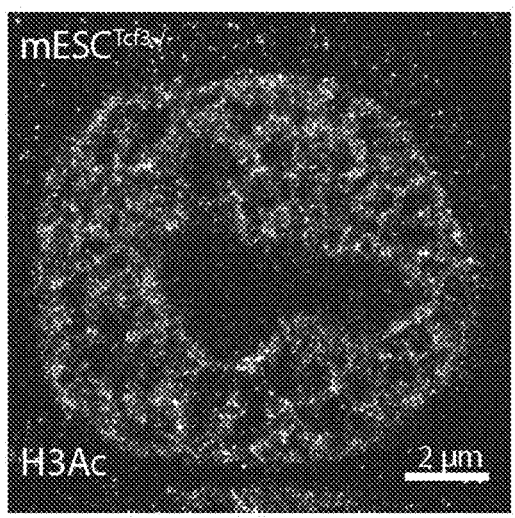
Figure 8:
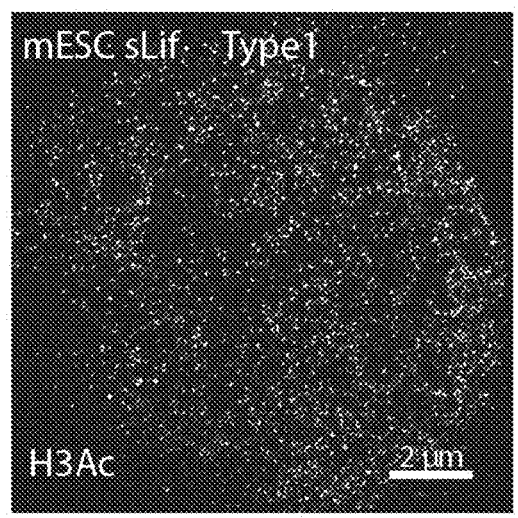
Figure 8:
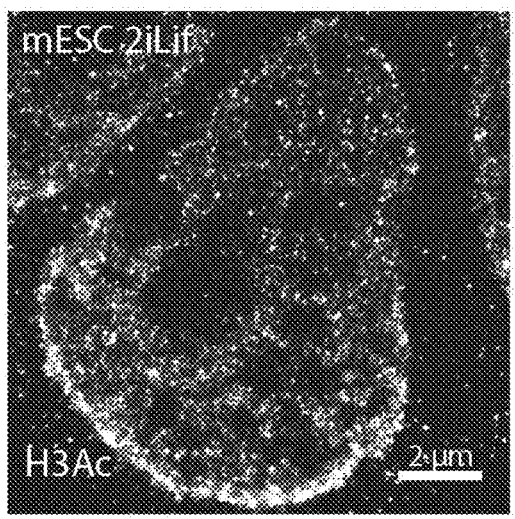
Figure 8:
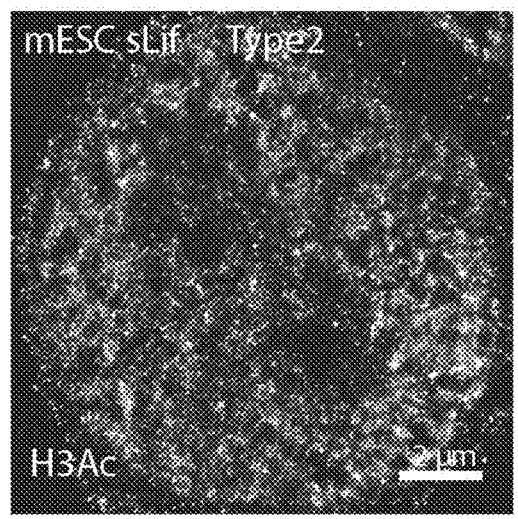
Figure 8:
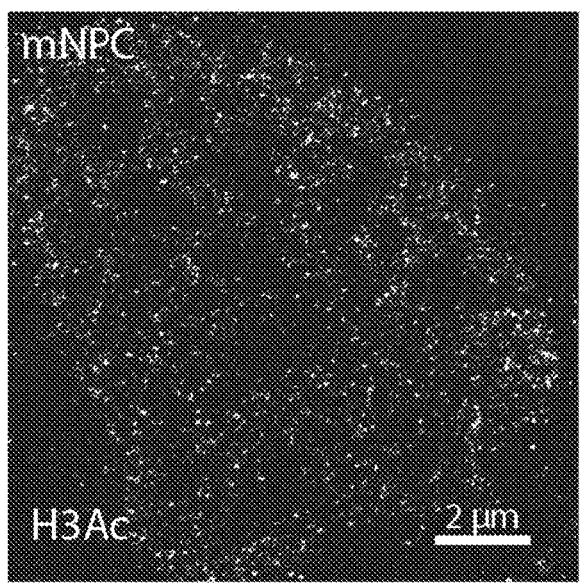

The activation of Wnt/β-catenin signaling pathway controls mESC pluripotency and self-renewal (Kuhl and Kuhl, 2013). Tcf3 acts as a key effector of this pathway by repressing Wnt target genes. Its deletion in mESCs maintains the ground state of pluripotency. H2B nanodomains in the STORM images of mESCs in which Tcf3 was knocked-out (mESCs$^{Tcf3-/-}$) resembled those found in naïve pluripotent mESCs (Type 2 and 2iLif) (FIG. 2E). In ESCs$^{Tcf3-/-}$ large epigenome modifications were previously seen as well as the increase of H3 acetylation (Lluis et al., 2011). Accordingly, there was increased level of acetylation in these cells (FIG. 8B) with respect to Type 1 mESCs cultured in sLif (FIG. 8C). Interestingly, the more pluripotent mESCs cultured in 2iLif (FIG. 8D) as well as the group of more pluripotent Type 2 mESCs cultured in sLif (FIG. 8E) also contained higher levels of H3 acetylation, while mNPCs showed a lower level of H3 acetylation (FIG. 8F). Of note, the spatial distribution of H3 acetylation resembled H2B nanodomain organization. Taken together, these results indicated that the ground state of pluripotency in mESCs was associated with increased acetylation and dimmer H2B nanodomains, which were more dispersed inside the nuclear space.

H1 is the linker histone that binds to the entry and exit sites of DNA that is wrapped around the histone octamer, keeping the nucleosome in place and leading to higher order compaction of the chromatin structure; (Woodcock et al., 2006). Therefore, H1 is thought to play an important role in chromatin organization. For example, mESCs that lack three H1 isoforms were shown to have chromatin structural changes such as reduced local chromatin compaction (Fan et al., 2005). To test whether the nanodomain organization of mESCs depended on H1, they imaged mutant mESCs carrying a deletion of three H1 isoforms (mESC$^{H1tKO}$). STORM imaging of H2B in these cells showed a large amount of dim nanodomains (FIG. 2F) having a similar organization to those observed in mESCs cultured in 2iLif and in mESCs$^{Tcf3-/-}$.

Figure 3:
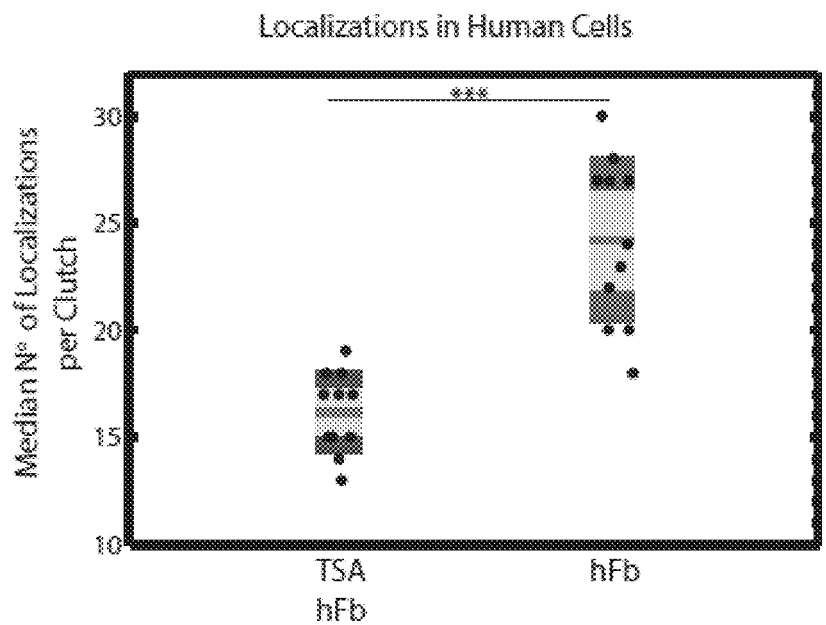
FIG. 3: The number of nucleosomes inside clutches correlates with cellular phenotype. Box plots showing the median number of H2B localizations per clutch in hFbs, TSA-hFbs (A); and in different mESCs and in mNPCs (B). (C) Calibration curve to convert from the median number of H2B localizations to the median number of nucleosomes per clutch. The median number of localizations per mononucleosome (hollow ring), 12—(medium grey) and 24-nucleosome array (black circle) assembled in vitro were used to generate the calibration curve. Light grey is data from a 4500 base pair (bp) plasmid assembled into nucleosome-arrays with an expected number of ~20 nucleosomes per array. Dark grey ring circle is data from fluorophore-labeled secondary antibody alone. The median number of localizations per 4500 bp plasmid and per secondary antibody was interpolated from the calibration curve to obtain the median number of nucleosomes. Inset shows the first part of the curve containing the secondary antibody and the mononucleosomes. Error bars correspond to standard deviations. (D) Box plots showing the median number of nucleosomes per clutch in hFbs, TSA-hFbs, in the different types of mESCs and in mNPCs. The dotted line corresponds to one nucleosome and the dashed line at 5 nucleosomes separates the more pluripotent cell types from those that are less pluripotent. (E-F) Box plots showing the median density of nucleosomes per clutch in hFbs, TSA-hFbs (E) in the different types of mESCs and mNPCs (F). For (A, B, D-F) each black dot shows the median number of nucleosomes obtained per individual nucleus. The dark grey is the median for the entire population of nuclei analyzed for that cell type. The light grey region corresponds to the standard error and the dark grey region to the standard deviation. Statistical significance between the different cell types was determined using one-way Anova. The stars indicate p-values according to *($p<0.05$), ($p<0.01$) and *($p<0.001$). See also FIG. 9.
Figure 3:
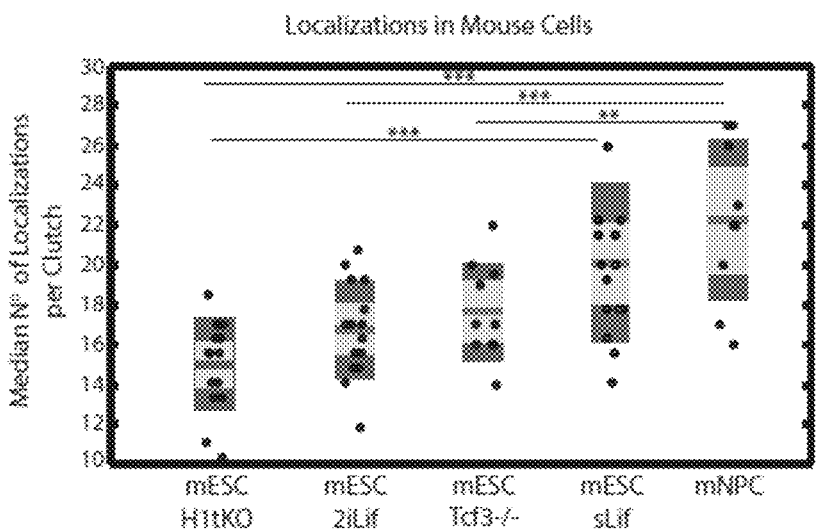
Figure 3:
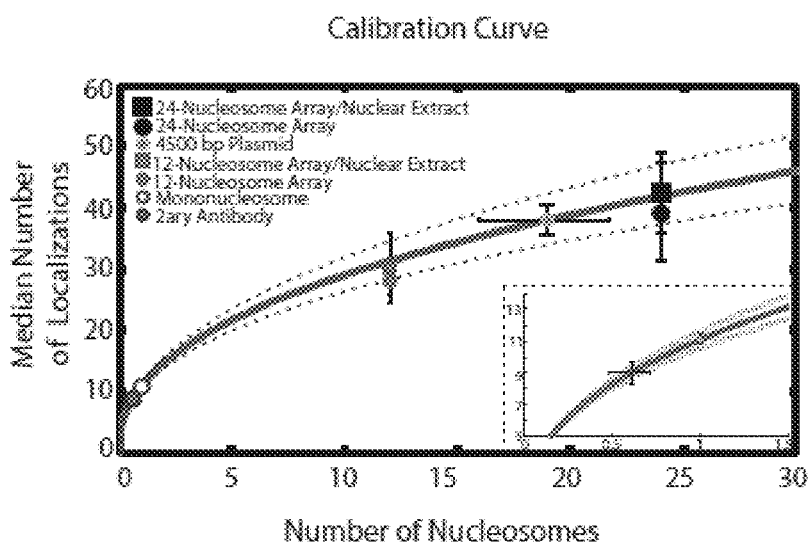
Figure 3:
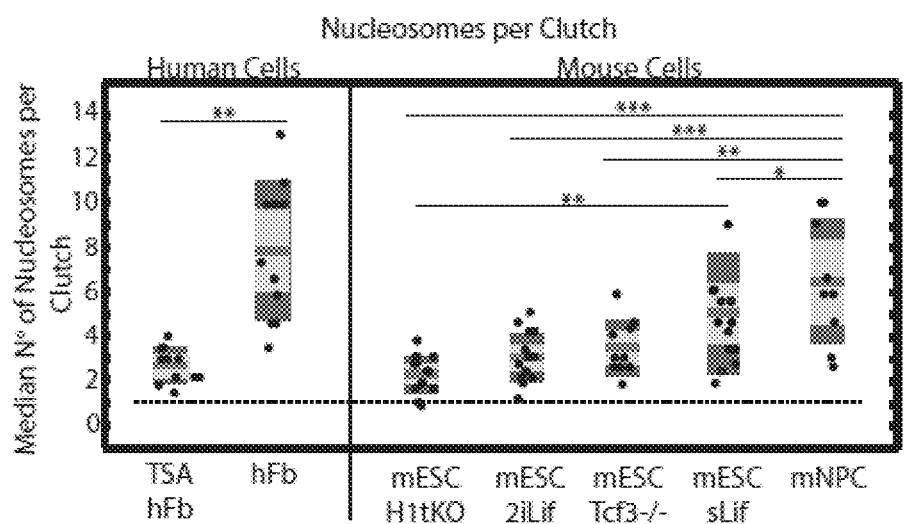
Figure 3:
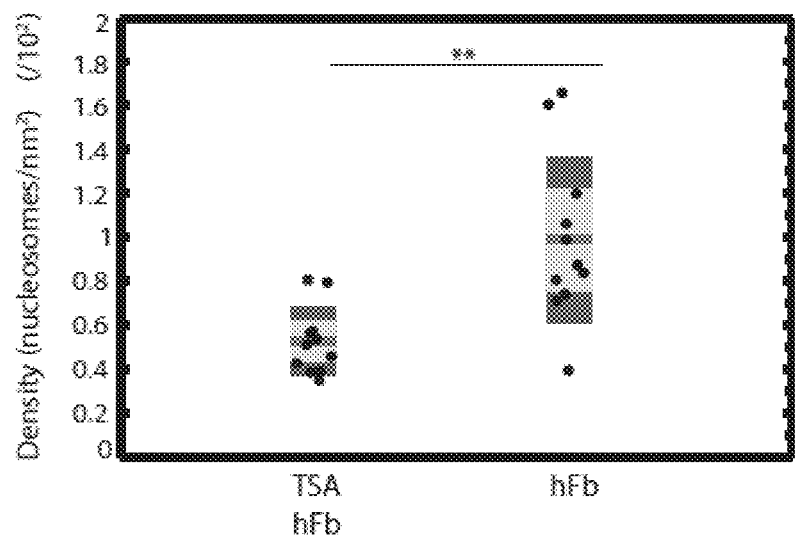
Figure 3:
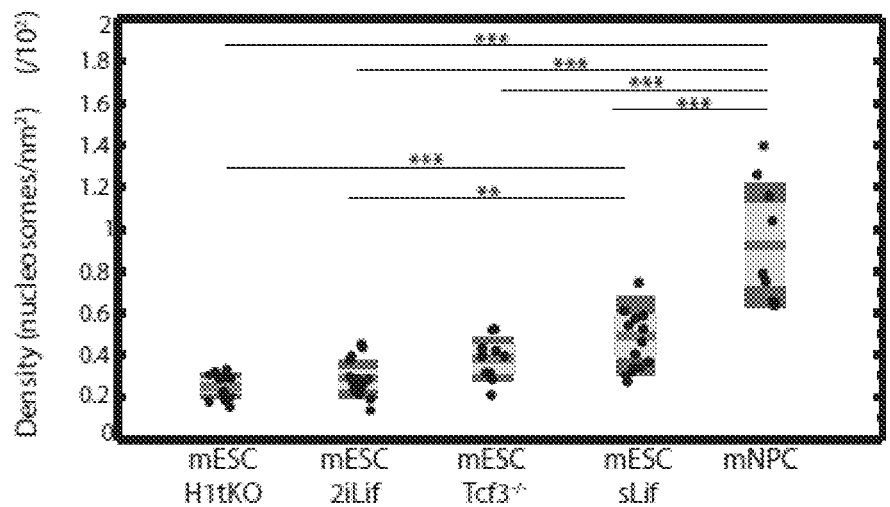

Quantification of the differences in nanodomain features among the various mESCs also confirmed that the number of localizations per nanodomain and nanodomain nnds were lower in ground-state mESCs with respect to somatic mNPCs (FIG. 2I) (see also FIG. 3 and associated text below for further quantitative analysis).

Example 3

Nanodomains Contain a Discrete Number of Nucleosomes and the Nucleosome Number Correlates with Cell Pluripotency The inventors next aimed to further quantify the changes they observed in the number of localizations (and hence brightness) of nanodomains in terms of the number of nucleosomes. There is not a one-to-one relationship between the number of localizations in STORM images and the number of nucleosomes mainly for two reasons: i) the antibody epitope labeling efficiency may not be 100%, ii) each fluorophore can undergo multiple photoswitching events, resulting in multiple localizations arising from a single fluorophore. However, the epitope labeling efficiency of the H2B antibody should be comparable across the human cells (hFbs, TSA-hFbs) and likewise across the different mESCs analyzed. In addition, the antibodies used were always labeled with a similar dye composition (Extended Experimental Procedures) and each cell was imaged in the same way (Table I) to obtain comparable number of localizations per antibody. Therefore, the number of nucleosomes should scale with the number of localizations. A similar approach has previously been used to quantify the receptor heterogeneity of synapses in brain slices (Dani et al., 2010).

TABLE I 405 nm laser power scheme used to activate fluorophores during STORM imaging

| 405 nm Laser Power (µW) | Frame Number |
|---|---|
| 0.5 | 800 |
| 3 | 7200 |
| 7 | 8000 |
| 22 | 10000 |
| 45 | 15200 |
| 78 | 20000 |
| 127 | 24000 |
| 200 | 28000 |
| 290 | 32000 |
| 500 | 36000 |
| 1000 | 40000 |
| 1630 | 42800 |
| 2000 | 44800 |

Nanodomains in any given nucleus contained a large distribution of localizations spanning two orders of magnitude (~3 to 300) (FIGS. 1C and 2I), indicating that these nanodomains comprised heterogeneous groups with varying numbers of nucleosomes. The inventors will refer to these heterogeneous nucleosome groups as "nucleosome clutches" in analogy to "egg clutches" and they will use the term "clutch size" interchangeably with the number of nucleosomes per clutch. Despite this heterogeneity, the median number of localizations per clutch in individual cells correlated strongly with cell type and showed statistically significant differences between hFbs and TSA-hFbs as well as among the different mESCs (FIG. 3A and B). Control experiments showed that the median number of localizations per clutch in hFbs was very similar when H3 was labeled (Nlocalizations=24±2) instead of H2B (Nlocalizations=24±4) and under different fixation and permeabilization conditions (Nlocalizations=24±4 for Ethanol/Methanol fixation, Nlocalizations=26±3 for PFA fixation), excluding potential sample labeling artifacts and further validating our approach. Overall, the differences in the median numbers of localizations indicate that nucleosomes assembled into larger clutches in hFbs compared to TSA-hFbs (FIG. 3A). Similarly, nucleosomes formed larger clutches in differentiated mNPCs and less pluripotent mESCs (mESC cultured in sLif) compared to the more pluripotent mESCs (mESC cultured in 2iLif and mESC$^{Tcf3-/-}$) and mESC$^{H1tKO}$ (FIG. 3B).

Figure 9:
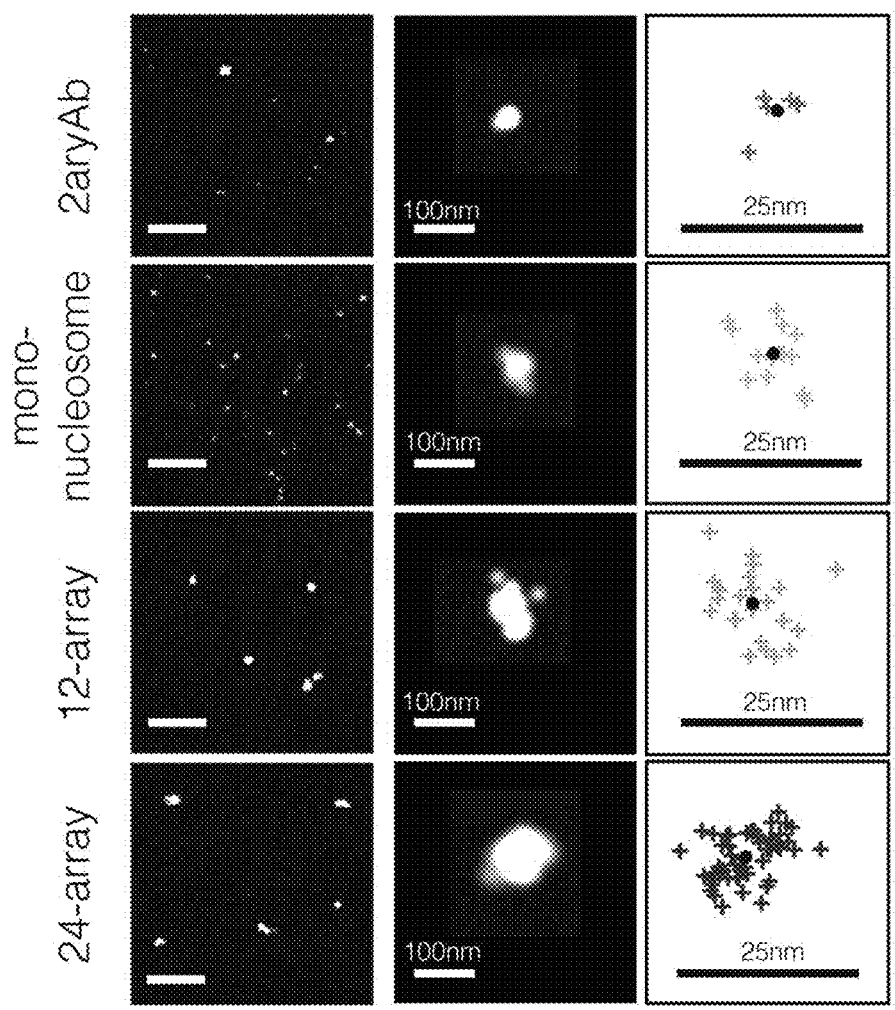
FIG. 9: In vitro experiments for the calibration curve. Related to FIG. 3. (A) Super-resolution images of fluorophore-labeled secondary antibodies (2ary Ab), mononucleosomes, 12- and 24-nucleosome arrays (left and middle) and examples of identified nanodomains in these images represented as crosses different shades of grey (right). (B) Plot showing the cumulative distribution of the number of localizations per fluorophore-labeled secondary antibody (light grey line), mononucleosome (middle grey line), 12—(dark grey line) and 24-nucleosome array (black line). The median numbers of localizations from these distributions (dashed lines) were used in the calibration curve to convert from the number of H2B localizations to the number of nucleosomes. (C) Example electron microscopy images obtained from the assembled 12-nucleosome array.
Figure 9:
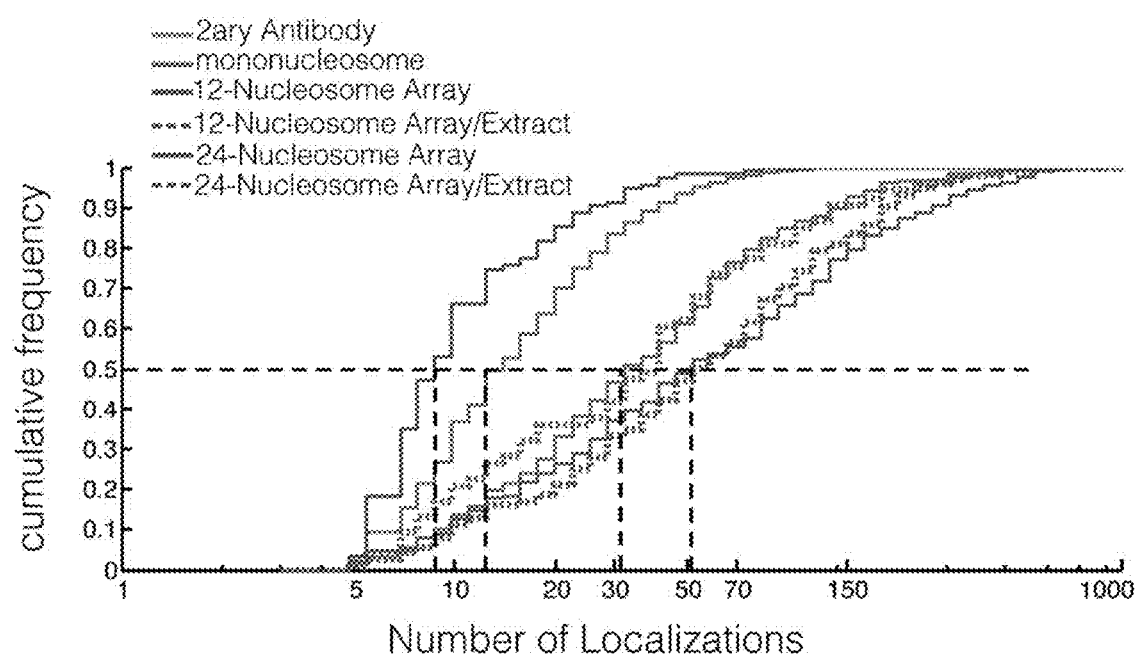
Figure 9:
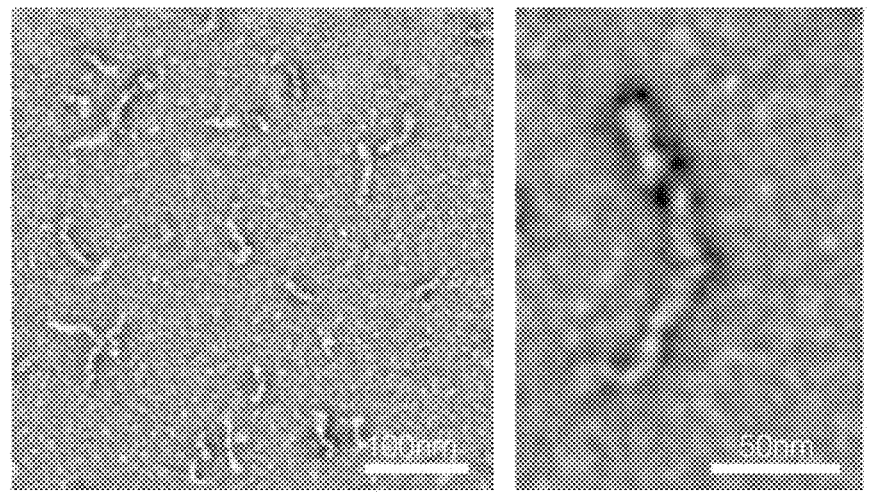

In order to relate the median number of localizations to the median number of nucleosomes while taking into account the limitations mentioned above, the inventors generated an in vitro calibration curve. To this end, single nucleosomes were assembled, spotted on coverglass in vitro, labeled using the same cell immunostaining protocol and STORM images were obtained using identical imaging conditions (Table I). As expected, the mononucleosome images resembled small clusters of localizations (FIG. 9A). The distribution of the number of localizations per mononucleosome was quantified as before (FIG. 9B). Next, polynucleosome arrays were assembled, spotted on glass under high salt conditions to induce compaction, immunostained and imaged. The plasmids used had a length and a specific DNA content allowing the assembly of exactly 12- and 24-nucleosomes (Grigoryev et al., 2009). Electron microscopy images of the in vitro assembled polynucleosome arrays showed that these structures had expected sizes for the number of nucleosomes that were in the arrays (FIG. 9C). STORM images of the polynucleosome arrays also resembled small clusters (FIG. 9A) and the distribution of the number of localizations per polynucleosome array was quantified as before (FIG. 9B). The median number of localizations in the mono-, 12- and 24-nucleosome data was used to generate the calibration curve (FIG. 3C).

The calibration curve was first validated by imaging nucleosomes assembled with circular DNA in vitro. The plasmid used had a DNA length allowing the assembly of ~20 nucleosomes. The polynucleosomes assembled with this plasmid were immunostained, imaged and the number of localizations per polynucleosome was quantified. The median number of localizations obtained was then interpolated from the calibration curve into the median number of nucleosomes and corresponded to 19.5±2.0 nucleosomes, confirming that the calibration curve was indeed accurate (FIG. 3C). Furthermore, to get an estimate of the number of antibodies present on each mononucleosome, single fluorophore-labeled secondary antibodies were immobilized on coverglass, imaged with STORM (FIG. 9A) and the number of localizations per antibody was quantified as before (FIG. 9B). The median number of localizations per antibody was 9, which is in agreement with previously measured photoswitching kinetics of the Alexa647 fluorophore (Nieuwenhuizen et al., 2013). This median number corresponded to 0.6 nucleosomes in the calibration curve (FIG. 3C, inset). Therefore, they calculated that on average 1.6 antibodies (1/0.6) were present on one mononucleosome.

The inventors next proceeded to convert the median number of localizations obtained from the in vivo STORM images (FIGS. 3A and 3B) to the median number of nucleosomes per clutch in the different cell types (FIG. 3D). It is possible that antibody epitope binding efficiency might be different between in vivo and in vitro conditions. In particular, due to nuclear crowding, antibody epitope binding efficiency might be lower in vivo than it is in vitro, which would lead to an underestimation of the number of nucleosomes per clutch. Nevertheless, this underestimation will not impact our conclusions regarding the relative relationship among the different cell types.

The median number of localizations in hFbs corresponded to a median number of ~8 nucleosomes per clutch whereas this number decreased to ~2 nucleosomes after TSA treatment (FIG. 3D, left). The mESCs cultured in sLif medium contained a median number of ~5 nucleosomes per clutch (FIG. 3D, right). These cells comprised a rather heterogeneous population consisting of cells with a median of ≥5 nucleosomes and cells with a median of <5 nucleosomes per clutch. The cells that contained ≥5 nucleosomes per clutch were the same population as the Type 1 mESCs. The median number of nucleosomes per clutch increased to ~6 in mNPCs (FIG. 3D, right). The mESCs cultured in 2iLif and mESC$^{Tcf3-/-}$ contained a median number of ~3 and ~3.5 nucleosomes per clutch, respectively (FIG. 3D, right). Finally, a median number of only ~2 nucleosomes per clutch were found in mESCs$^{H1tKO}$ (FIG. 3D, right). While the variability in the median number of nucleosomes per clutch was high among the different nuclei analyzed for mNPCs and mESCs cultured in sLif, this number was more uniform among the different nuclei analyzed for 2iLif, ESCs$^{Tcf3-/-}$ and mESCs$^{H1tKO}$ (FIG. 3D, right). These results overall indicate that nucleosomes are assembled together in smaller clutches in cells with pluripotent features and in increasing numbers in somatic differentiated cells. Furthermore, clutch size drastically changes upon chromatin decondensation after TSA treatment and upon differentiation of mESCs into mNPCs.

To determine whether the observed changes in nucleosome clutches corresponded to changes in the compaction of nucleosomes inside the clutches, the median nucleosome density was calculated by dividing the median number of nucleosomes per clutch with the median area of the clutches. Indeed, the nucleosomes in hFbs were more densely compacted inside the clutches compared to TSA-hFbs (FIG. 3E). Nucleosome density was likewise higher for mNPCs and mESCs cultured in sLif with respect to mESCs cultured in 2iLif medium, mESCs$^{Tcf3-/-}$ and mESCs$^{H1tKO}$ (FIG. 3F). These results show that nucleosomes are less densely compacted in pluripotent cells and nucleosome compaction increases upon differentiation.

Example 4

Nucleosome Content Inside Clutches is Predictive of the Pluripotency Grade of Human Induced Pluripotent Stem Cells Given the correlation between clutch size and pluripotency level of different mESCs, the inventors next aimed to study whether the identification of the number of nucleosomes per clutch could be predictive of the pluripotency grade in hiPSC clones.

To this end, different hiPSC clones were generated from hFbs and were characterized using standard methods such as alkaline phosphatase (AP) staining, analysis of expression of stem cell genes, formation of embryoid bodies and in vivo teratoma in immune-compromised mice. Based on the results of this characterization, hiPSC clone 13 was the most pluripotent since it was AP positive, expressed high levels of the stem cell markers TRA1-60, SSEA4, Oct4, Sox2 and Nanog, formed embryoid bodies, which differentiated in the three germ layers, and generated large and fully differentiated teratomas in mice (FIG. 10A-D). In contrast, the hiPSC clone 8 was the least pluripotent since, although it showed expression of stem cell markers, the OCt4 expression level of single cells was fourteen-fold lower compared to hiPSC clone 13, it did not form the ectoderm layer from the embryoid bodies and it generated very small undifferentiated teratomas in vivo (FIG. 10A-D). To rank the pluripotency grade of all hiPSC clones in a more quantitative manner, they used a recently established gene card technology that compares the expression level of sternness genes to well established standard hiPSC clones and gives a pluripotency score based on this comparison (Bock et al., 2011). The gene card results agreed with the classical characterization, showing clone 8 as being the least and clone 13 as being the most pluripotent and allowed quantitative ranking of the rest of the hiPSC clones in order of pluripotency grade (FIG. 10E).

Figure 4:
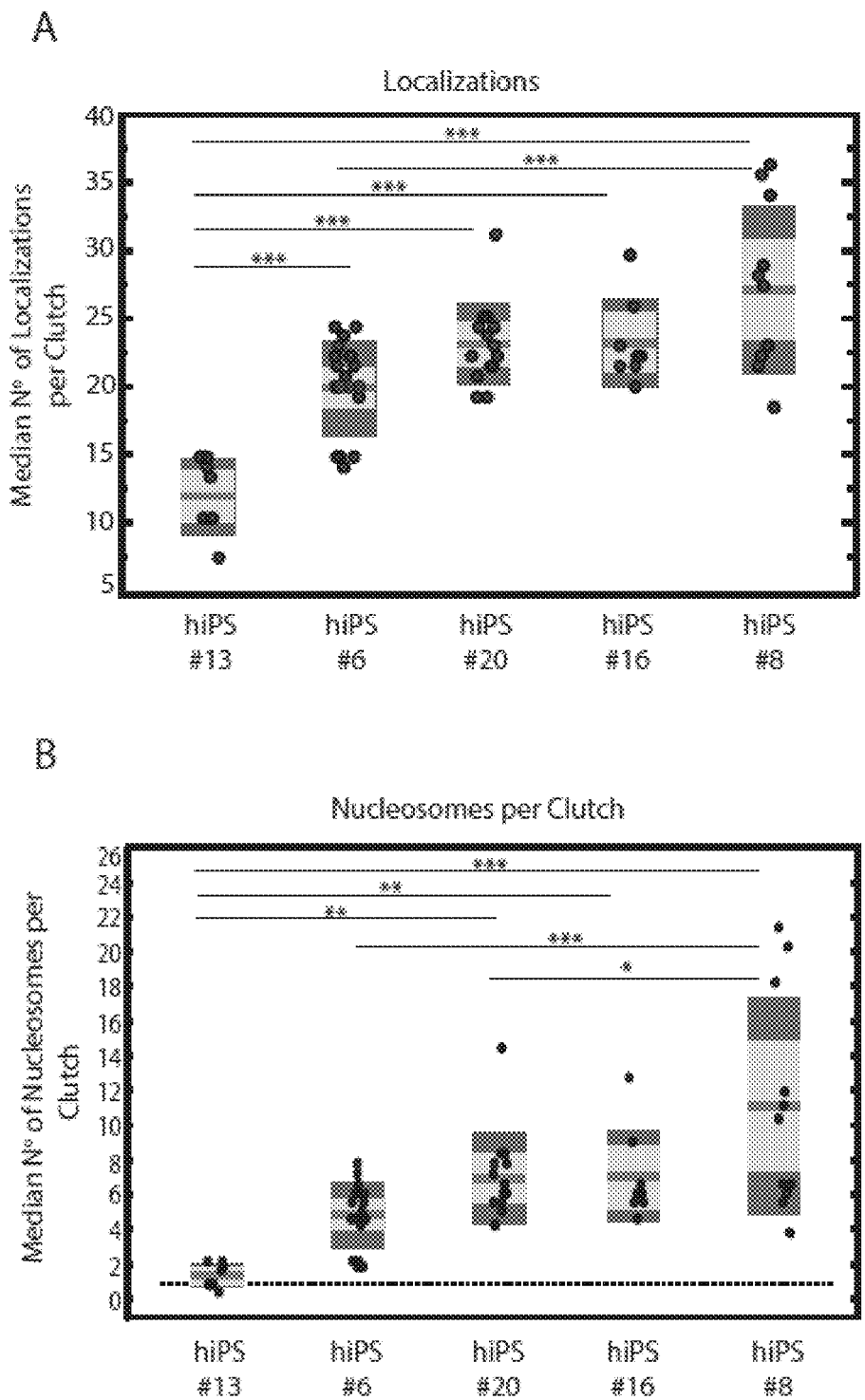
FIG. 4: Clutch size is predictive of pluripotency grade in human induced pluripotent stem cells clones. (A) Box plots showing the median number of H2B localizations per clutch in different human induced pluripotent stem cell clones (hiPSCs). (B) Box plots showing the median number of nucleosomes per clutch in the different hiPSCs. The dotted line corresponds to one nucleosome. (C) Box plots showing the median density of nucleosomes per clutch in the different hiPSCs. (D) Pluripotency score of the different hiPSCs obtained from the gene card plotted against the median number of nucleosomes. Error bars indicate standard deviations. For black dots, lines, box plot grey shades and statistics in (A-C) see description in the legend of FIG. 3. See also FIG. 10.
Figure 4:
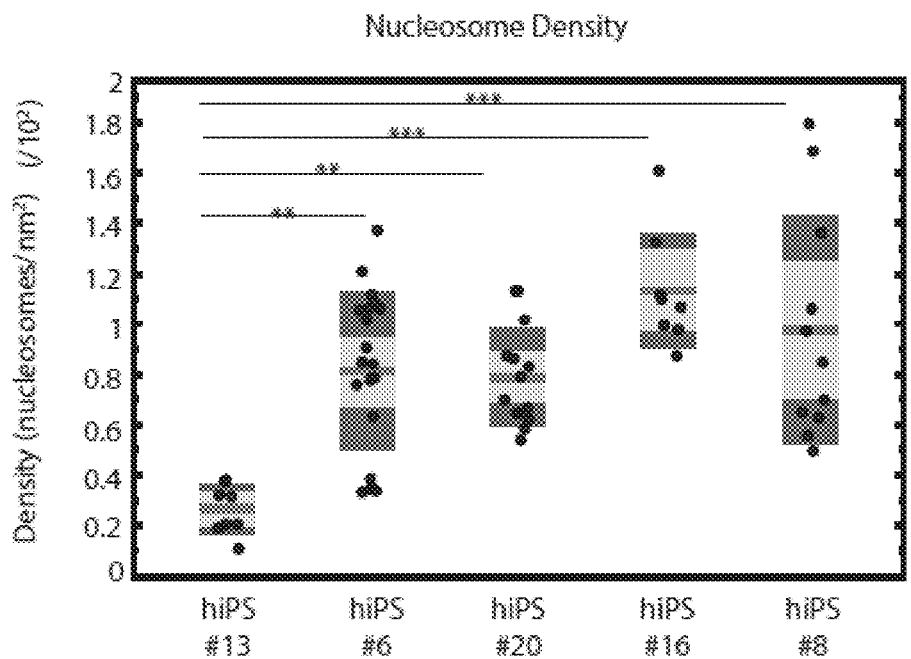
Figure 4:
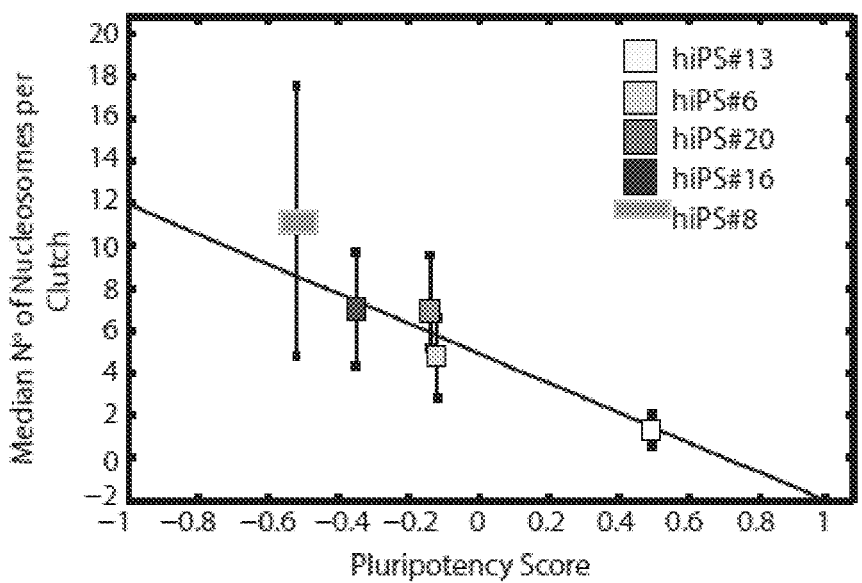

In a double blind fashion, the median number of localizations was quantified after STORM imaging of all the hiPSC clones (FIG. 4A), which showed statistically significant differences among the different clones and a gradual increase of the median number of localizations passing from the more pluripotent hiPSCs clone, #13, to the less pluripotent one, #8. The calibration curve was used to deduce the median number and density of nucleosomes inside clutches in each hiPSC clone (FIGS. 4B and 4C). There was a remarkable agreement between the pluripotency score obtained from the gene card and the clutch size (FIG. 4D), (correlation analysis showed r=−0.94 indicating high level of anticorrelation, low number of nucleosomes per clutch for high pluripotency score and vice versa). Indeed, the more pluripotent hiPSC clone 13 had clutches with a median number of only 1 nucleosome and low density (FIG. 4B and C) while clutch size and density increased progressively with the decrease in pluripotency of the hiPSC clones.

Example 5

Larger Clutches have Higher Levels of H1 and Lower Levels of RNA Polymerase II

The arrangement of nucleosomes in large and small clutches with higher and lower compaction respectively could potentially facilitate the binding of transcription factors, polymerases and other proteins to the DNA, which should be more accessible in regions containing a smaller number of nucleosomes. The compaction of the nucleosomes within the clutches, on the other hand, should be aided by the presence of linker histone protein H1, which is known to be involved in nucleosome compaction as well as to be enriched in heterochromatin (Fan et al., 2005; Shen et al., 1995; Woodcock et al., 2006). Thus, to evaluate differences in the heterochromatin content and accessibility of RNA Polymerase II (PolII), multi-color super-resolution imaging of H2B with histone H1 and of H2B with PolII was carried out. For H1, an antibody that recognizes all of its isoforms was used. In the case of PolII, an antibody against phosphoserine 5 of the carboxiterminal domain of PolII (PolII11) was used to image both PolII at the initiation complex and the elongating PolII.

Figure 5:
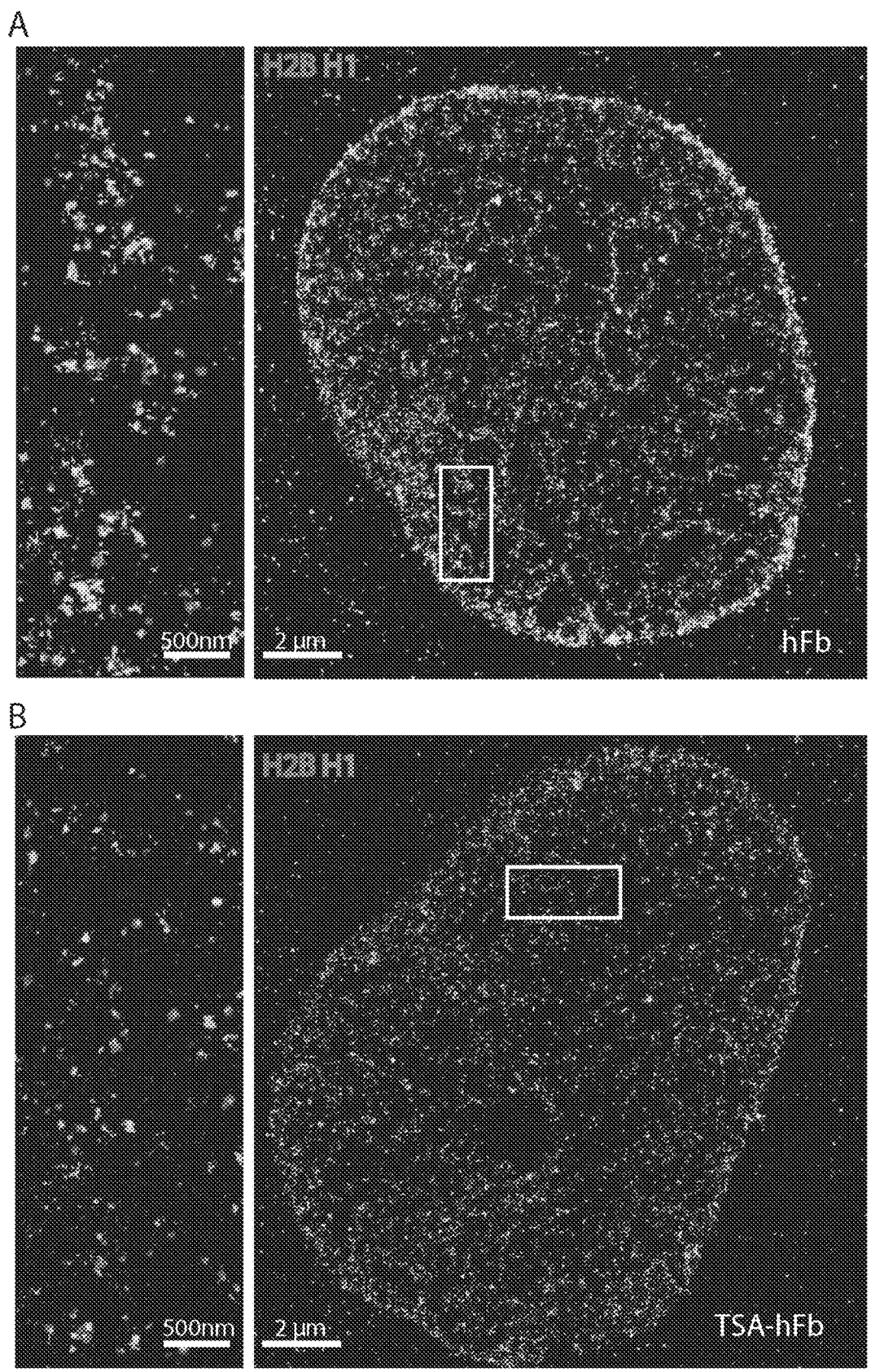
FIG. 5: The linker histone H1 increases in large clutches while RNA Polymerase II associates with small clutches. (A-B) Multi-color super-resolution images showing H2B and H1 in hFb (A) and TSA-hFb (B). Higher zooms of the regions inside white rectangles are shown next to each nucleus. (C) Plot showing the number of H2B (x-axis) and H1 (y-axis) localizations inside clutches for which these two histones showed colocalization. Error bars in x-axis indicate standard deviations and in y-axis indicate standard errors. (D) Multi-color super-resolution image showing H2B and RNA polymerase II (PolII11) in TSA-hFb. Progressive zooms of the regions inside white rectangles are shown below the image of the nucleus. (E) (upper) Plot showing the distribution of nearest neighbour distances between H2B and PolII11 in hFb (dark grey) and TSA-hFb (light grey). (lower) Plot showing the number of H2B localizations within clutches (y-axis) as a function of the nearest neighbour distances between PolII11 and H2B (x-axis) for hFb (dark grey) and TSA-hFb (light grey). Error bars indicate standard errors.
Figure 5:
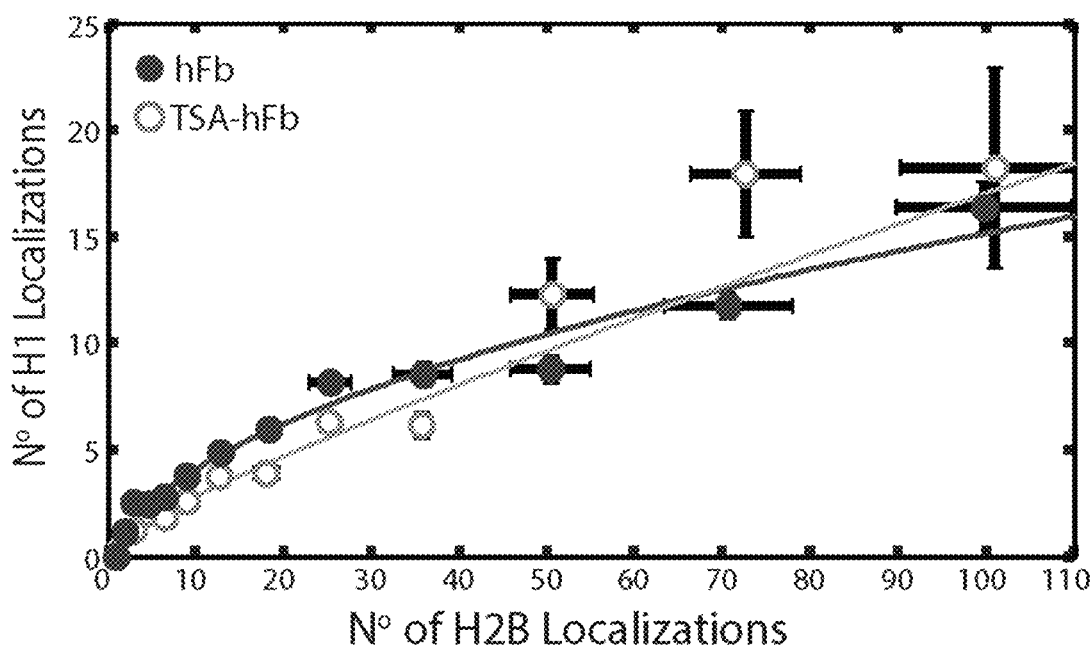
Figure 5:
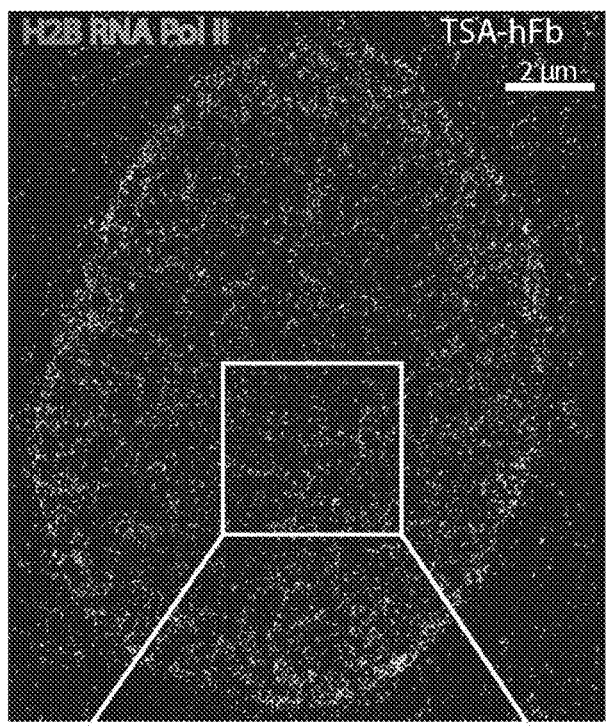
Figure 5:
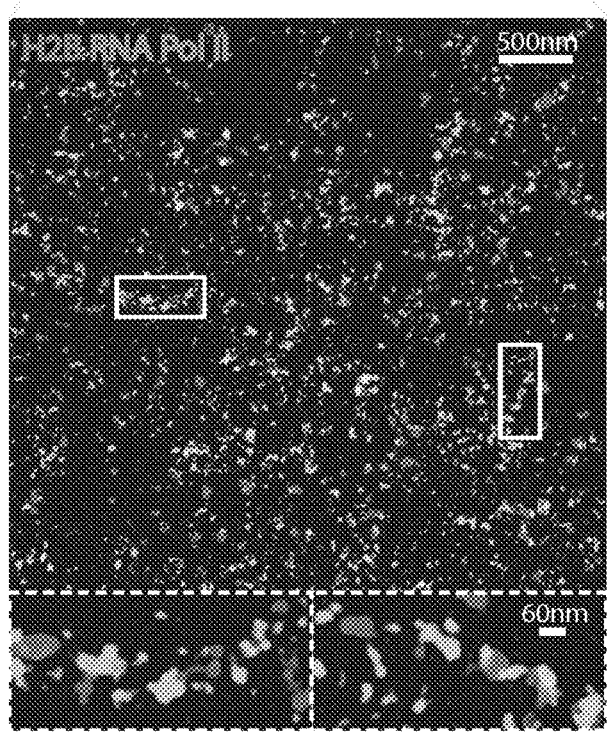
Figure 5:
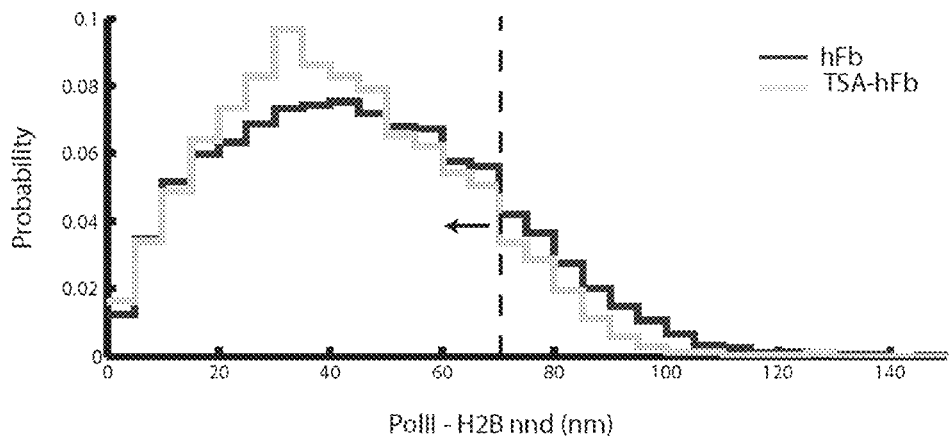
Figure 5:
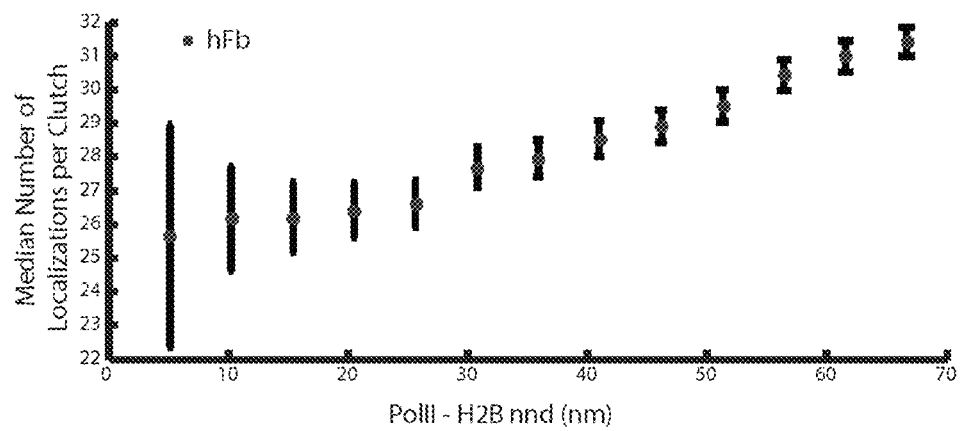
Figure 5:
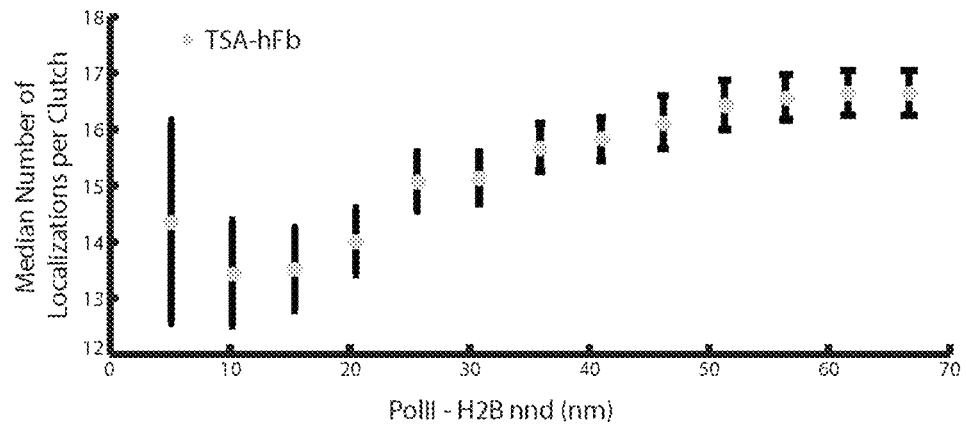

The inventors first recorded multi-color STORM images of H2B and H1 in hFbs and TSA-hFbs (FIGS. 5A and 5B), which significantly differ in the median number of nucleosomes per clutch (FIG. 3D). H1 was more enriched at the nuclear periphery of hFbs where heterochromatin is more abundant (Meister and Taddei, 2013) (FIG. 5A). A higher percentage of H2B co-localized with H1 in hFbs (61±11%) compared to TSA-hFbs (42±6%) (p=0.028). They next counted the number of H1 localizations and compared it to the number of H2B localizations inside the clutches (FIG. 5C). For both hFbs and TSA-hFbs the number of H1 localizations increased with the number of H2B localizations. Although they did not generate a corresponding calibration curve to convert from the number of H1 localizations to the number of H1 histones, this result overall suggests that the number of H1 histones correlates with the number of nucleosomes inside the clutches.

Figure 11:
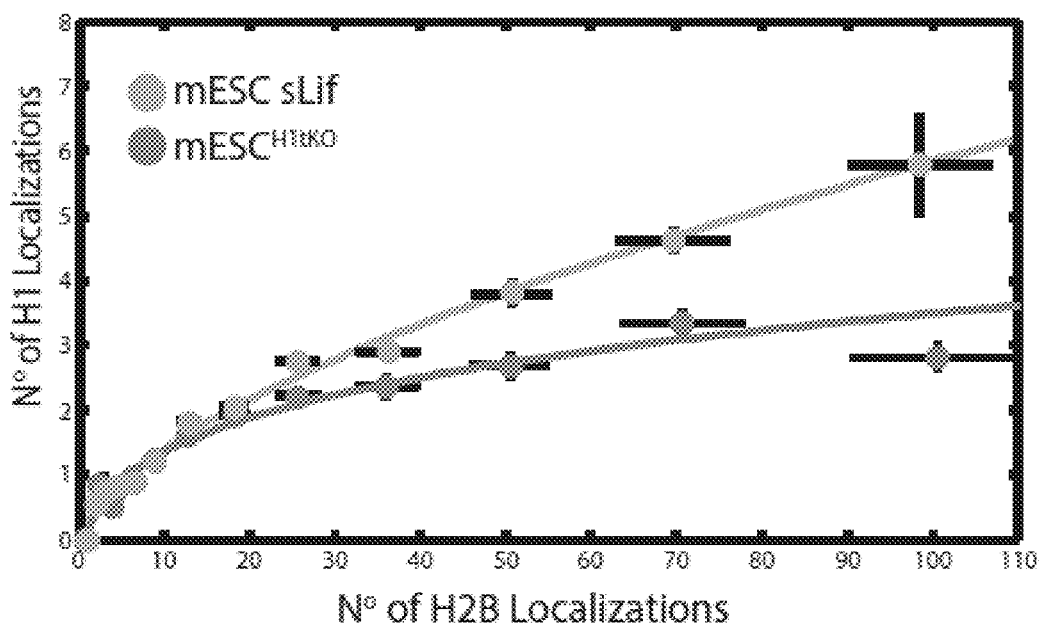
FIG. 11: Quantification of the number of H2B and H1 localizations in mESCs. Related to FIG. 5. (A) Plot showing the number of H2B (x-axis) and H1 (y-axis) localizations inside clutches for which these two histones showed colocalization in mESCs cultured in sLif (light grey) and mESCs$^{H1tKO}$ (dark grey). (B) Bar plot showing the average number of H1 localizations detected per area in the nuclei of mESCs cultured in sLif (light grey) and mESCs$^{H1tKO}$ (dark grey). (A-B) Error bars in x-axis indicate standard deviations in y-axis indicate standard errors.
Figure 11:
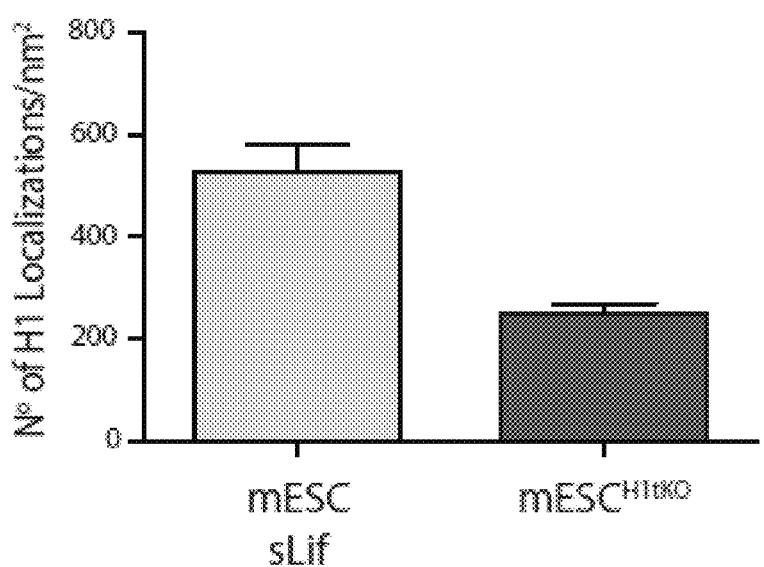

In mESCs cultured in sLif around 54±2% of H2B colocalized with H1 and the number of H1 localizations also increased with the number of H2B localizations (FIG. 11A). As expected, mESCs$^{H1tKO}$ contained much lower amount of H1 (FIG. 11B) and only around 35±4% of H2B colocalized with H1 (p=0.0057). Despite the low amount of H1 in these cells, the same trend was observed in which the number of H1 localizations was increased in clutches with an increasing number of H2B localizations (FIG. 11A). These results overall indicate that H1-H2B colocalization increases in cells containing larger clutches and in addition these large clutches contain more H1 compared to the small ones.

Next, the inventors analyzed PolII and H2B multi-color STORM images of hFbs and TSA-hFbs. In both cases, PolII was found interspersed with the nucleosome clutches (FIG. 5D and insets). Nearest neighbor distance analysis showed that the PolII-H2B distance peaked at around 40 nm (FIG. 5E, top plot). They rationalized that the analyzed the number of H2B localizations within clutches as a function of the nearest neighbor distances between PolII and H2B. Even though hFbs (dark grey) and TSA-hFbs (light grey) have clutches with very different sizes, in both cases the nearest neighbor distances between PolII and H2B were shorter for smaller clutches, indicating that PolII was indeed closer to the smaller clutches with few nucleosomes (FIG. 5E, bottom plot). These results indicate that PolII can access small clutches, which likely form the chromatin fiber arrangement of transcribed chromatin regions.

Example 6

The DNA Fiber is not Fully Occupied with Nucleosomes

The organization of nucleosomes in discrete clutches that are separated in space implies that nucleosome-depleted regions likely exist in the chromatin fiber. The inventors hypothesized that these regions might be the result of two alternative mechanisms. First, removal of one or more nucleosomes in between nucleosome-rich regions can generate the clutch-like organization of nucleosomes observed in STORM images. Second, variations in the length of the linker-DNA between subsequent nucleosomes can generate nucleosome-depleted regions if the linker-DNA length becomes larger than the spatial resolution.

Figure 6:
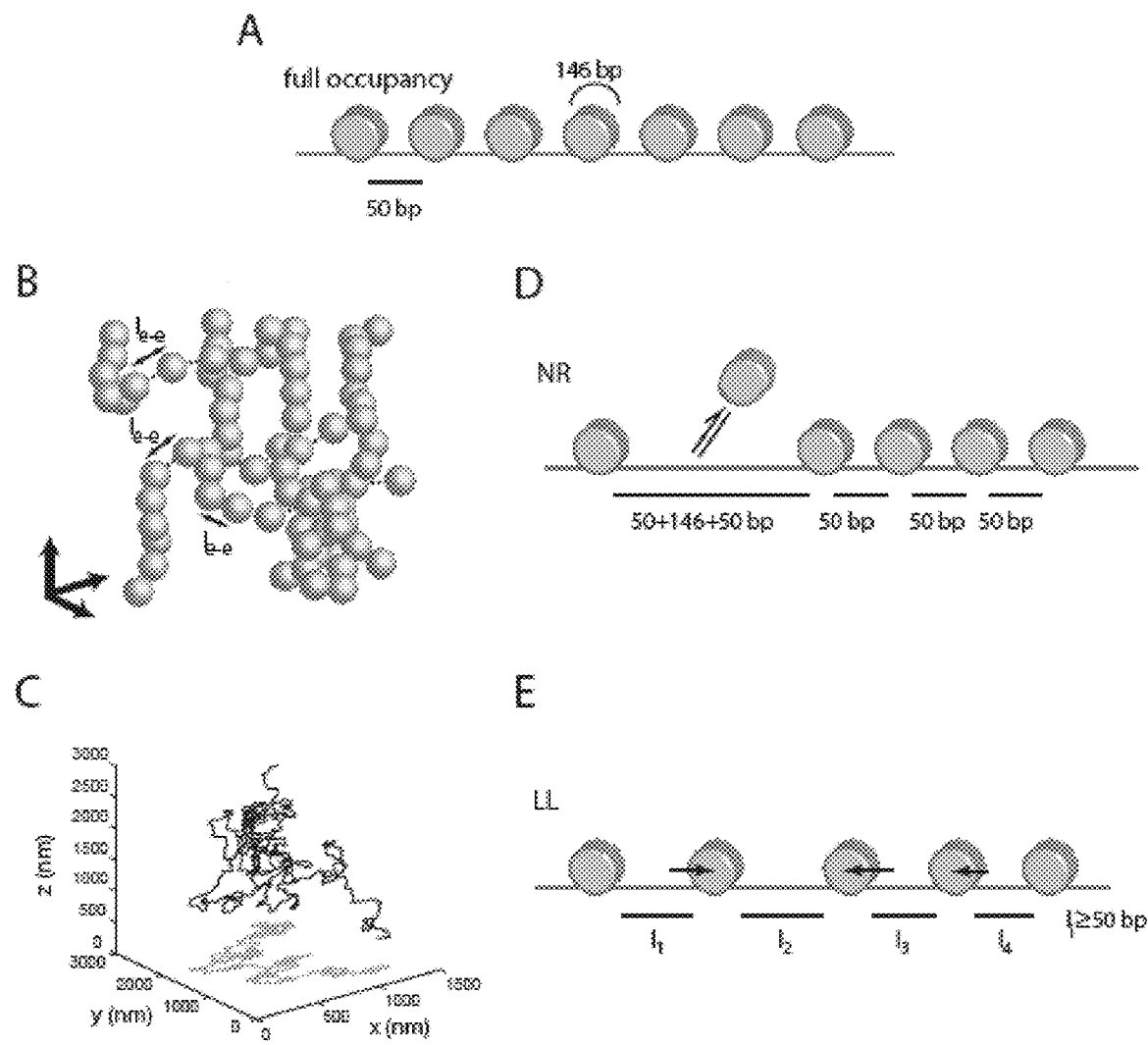
FIG. 6: Computer simulations of nucleosome occupancy. (A) Nucleosomes (light grey) are initially arranged at regular intervals of 50 bp on the DNA fiber (full occupancy). 146 bp of DNA wraps around each nucleosome. (B) A three-dimensional DNA fiber arrangement is generated by positioning nucleosomes according to a Gaussian chain model with end-to-end distances (le-e) calculated according to a worm like chain model (WLM) for a polymer with a persistence length of 150 bp (C) The resulting DNA fiber configuration is projected onto 2D space (D) In the nucleosome removal (NR) model nucleosomes are removed from the DNA with a given probability ranging from 0 to 95%. When a nucleosome is removed, the linker-DNA length between the neighboring nucleosomes increases by 146 bp. (E) In the Linker Length (LL) model the linker-DNA lengths (li) between subsequent nucleosomes are drawn from normal distributions whose averages are varied from 50 bp to 3000 bp. (F) Examples of synthetic super-resolution images obtained from the simulated arrangement of nucleosomes at 75%, 57% and 45% nucleosome occupancy. (G) Comparison of simulation results for the NR—(black squares and solid line) and LL-Models (white circles and dotted line) to experimental data for hFbs (horizontal dark grey line) and TSA-hFbs (horizontal red line) at different levels of nucleosome occupancy (x-axis). The comparison is made for the number of localizations per clutch (upper) nearest neighbour distances (nnds) of clutches (middle) and clutch area (lower). The vertical dark grey lines and black arrows show the nucleosome occupancy values for which the simulation results of the different models intersect the experimental data for the hFb. Similarly, the vertical light grey lines and black arrows show the nucleosome occupancy values for which the simulation results intersect the experimental data for the TSA-hFb. See also FIG. 12.
Figure 6:
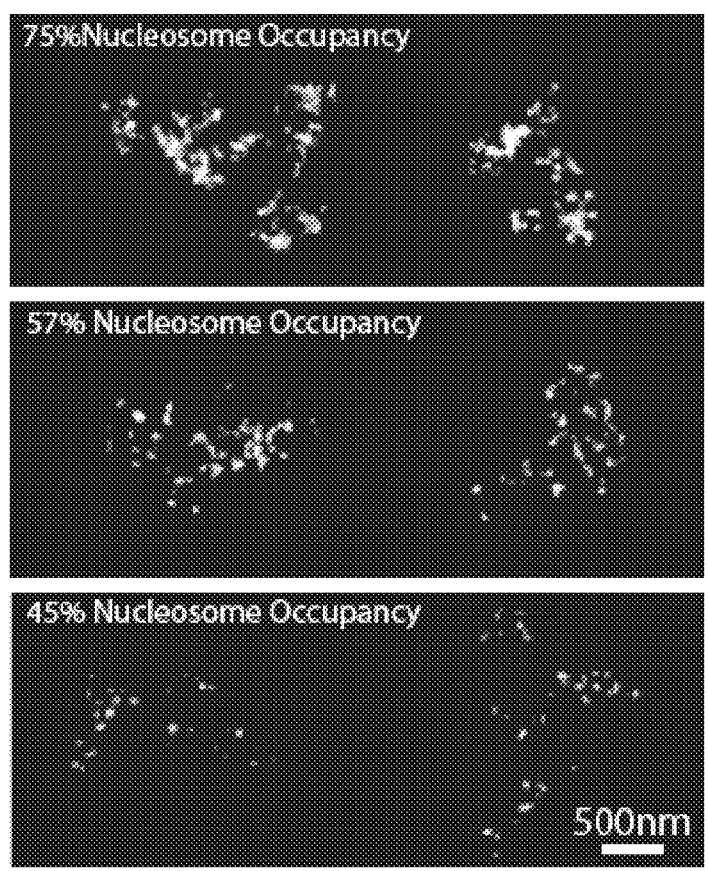
Figure 6:
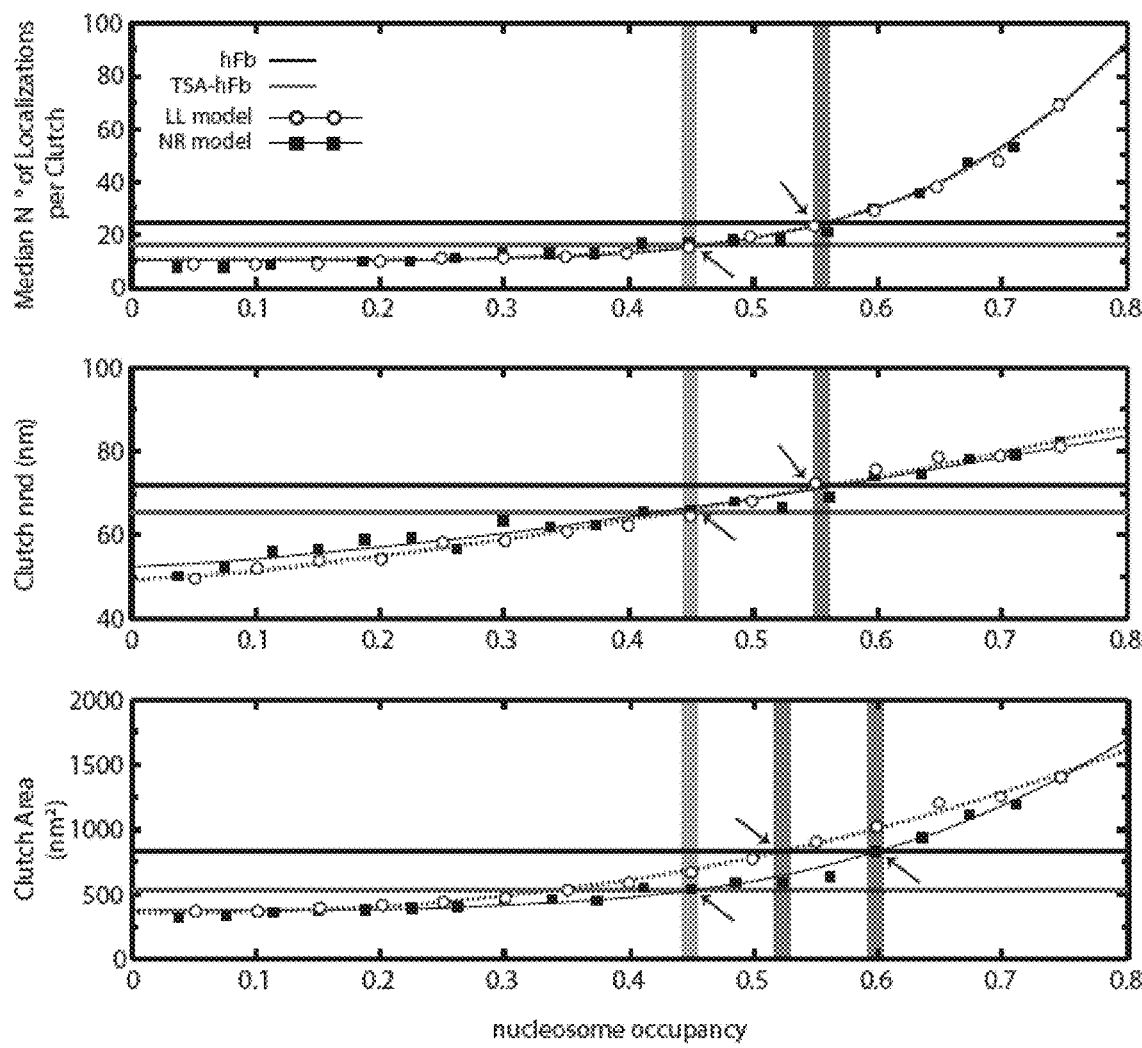

To gain more insight into nucleosome occupancy in human fibroblast cells, they used coarse-grained computer simulations of nucleosome spatial arrangement, using a simple model with only few parameters. Nucleosomes were placed along the DNA fiber at regular intervals with 146 bp of DNA wrapped around each nucleosome and with 50 bp of linker-DNA separating them, which is the average linker-DNA length measured in previous studies, (FIG. 6A). They define this configuration as full occupancy of DNA, which in reality corresponds to ~75% of DNA occupied with nucleosomes after accounting for the 50 bp linker DNA. Final nucleosome positions were generated according to a Gaussian chain model (FIG. 6B). Inter-nucleosome distances (le-e) were calculated by converting the linker-DNA length (50 bp) into an end-to-end distance according to the worm-like-chain theory for a polymer with 150 bp persistence length, which is the experimentally determined persistence length of double stranded DNA. The resulting DNA fiber configuration was then projected onto two-dimensional space (FIG. 6C).

To simulate nucleosome removal, the linker-DNA length was kept fixed at 50 bp but nucleosomes were randomly removed with a probability ranging from p=0 to p=95% (NR model) (FIG. 6D). When a nucleosome was removed, the 146 bp DNA wrapped around this nucleosome unraveled and the two neighboring nucleosomes became separated by 50+146+50 bp of DNA. In this model, a low probability of nucleosome removal led to high nucleosome occupancy of the DNA fiber and vice versa. The nucleosome occupancy level was calculated according to Equation 1 shown before.

To simulate variations in linker-DNA length (l) between subsequent nucleosomes (LL Model) the 146 bp of DNA wrapped around nucleosomes was maintained, but the linker-DNA lengths (l) were extracted from normal distributions with average linker-DNA lengths (laverage) ranging from 50 bp to ~3000 bp (FIG. 6E). Nucleosome occupancy in the LL model depended on $l_{average}$ with small $l_{average}$ leading to high occupancy and vice versa. The nucleosome occupancy level was calculated according to Equation 2 previously shown.

Finally, as a control, the potential effect of labeling efficiency was also simulated by decorating the nucleosomes with antibodies corresponding to an average of 1.6 antibodies per nucleosome (in vitro measured value, FIG. 3C, inset) and progressively decreasing the labeling efficiency by randomly removing antibodies from the nucleosomes.

Synthetic STORM images of the nucleosomes along the DNA fiber at different levels of nucleosome occupancy (FIG. 6F) or labeling efficiency (FIG. 12A) were generated by assigning to each nucleosome a given number of localizations. The number of localizations was extracted from the experimental distribution of the in vitro mononucleosome (for NR and LL models) or secondary antibody data (for labeling efficiency simulations) (FIG. 9B). The synthetic STORM images at different nucleosome occupancy levels (FIG. 6F) showed striking resemblance to the experimental images with nucleosomes grouped in clutches generating high and low density regions. The number of localizations, area and nearest neighbor distances of the nucleosome clutches in these synthetic STORM images were determined using identical analysis parameters as before, including threshold. The median number of localizations, the median nearest neighbor distances and the median area obtained from the NR model (filled squares and solid line) and the LL model (open circles and dashed line) were plotted as a function of nucleosome occupancy level (FIG. 6G). These data are the results of at least thousand simulations for each parameter value. Also shown are the corresponding median values obtained from the experimental data for hFbs (dark grey line) and TSA-hFbs (light grey line).

In the case of the number of localizations, both the NR and LL models intersected the experimental values at around 56% and 46% occupancy for the hFbs and TSA-hFbs, respectively (FIG. 6G, top). Similarly, in the case of the nearest neighbor distances, both the NR and LL models intersected the experimental values at around similar level of occupancy for both cell types (57% hFbs and 43% TSA-hFbs) (FIG. 6G, middle). In the case of the nanodomain area, the NR model intersected the experimental value for TSA-hFbs at similar level of occupancy (45%) whereas the LL model intersected the experimental value at a much lower occupancy level (34%) (FIG. 6G, bottom). In the case of the hFbs, the NR model intersected the experimental value at a slightly higher occupancy level than those obtained from the other two parameters (60%) whereas the LL model intersected this value at a slightly lower occupancy level (52%) (FIG. 6G, bottom). Finally, in the case of labeling efficiency tests, the three measured experimental parameters (number of localizations, area and nearest neighbor distances) could not be simultaneously reproduced at any given labeling efficiency for hFbs and TSA-hFbs (FIG. 12B), indicating that poor labeling efficiency alone cannot explain the experimental observations.

Taken altogether, these results indicate that the nucleosome occupancy in TSA-hFbs is around 45% and nucleosome removal is likely the dominant mechanism to generate nucleosome poor regions along the DNA fiber since all three measured parameters of the experimental data can be recapitulated with this model. In hFbs, around 56% of the DNA fiber is occupied with nucleosomes and likely both nucleosome removal and linker-DNA length modifications play a role in generating the nucleosome-depleted regions. For these nucleosome occupancy levels (45% and 56%) the simulation results not only reproduced the median values observed for the experimental data but also the full experimental distributions of the three parameters fit well to the simulated distributions (FIG. 12C-E).

Example 7

Chromatin State of Reprogrammed Cells

Three distinct experimental approaches have shown nuclear reprogramming: nuclear transfer, transcription-factor transduction and cell-fusion.

The inventors explored how the chromatin state of somatic human fibroblasts changes when using the cell-fusion method for reprogramming. Cell fusion can generate synkaryons or heterokaryons. Synkaryons proliferate, after the nuclei of the original cells fuse in a tetraploid genome, whereas heterokaryons do not proliferate and contain the original nuclei distinct sharing the same cytoplasm. Furthermore if the two fusing cell types are from different species, their gene products can be distinguished. H. M. Blau and A. Fisher laboratories have generated heterokaryons between mESCs and human somatic cells (fibroblasts and B lymphocytes), demonstrating that the reprogramming was very fast and the human nuclei were shown to start expressing pluripotent markers already 24 h after fusion. Furthermore, the reprogrammed human cells expressed a profile of transcripts seen in human ESCs that were not expressed in mouse ESCs, suggesting that the human nuclei was reprogrammed through trans-acting factors from the mouse nuclei and later the process was finalized and established by reactivated cis-acting factors from the human nuclei.

Thus, the inventors analyzed the clutches reorganization occurring in a somatic nucleus after cell fusion with Embryonic Stem Cells.

mES cells were fused with hFb cells and stained with surface markers. Fused cells were then FACS sorted. Sorted cells were fixed at different time points after fusion, The histones were imaged and the nucleosome clutches quantified as previously described.

Figure 13:
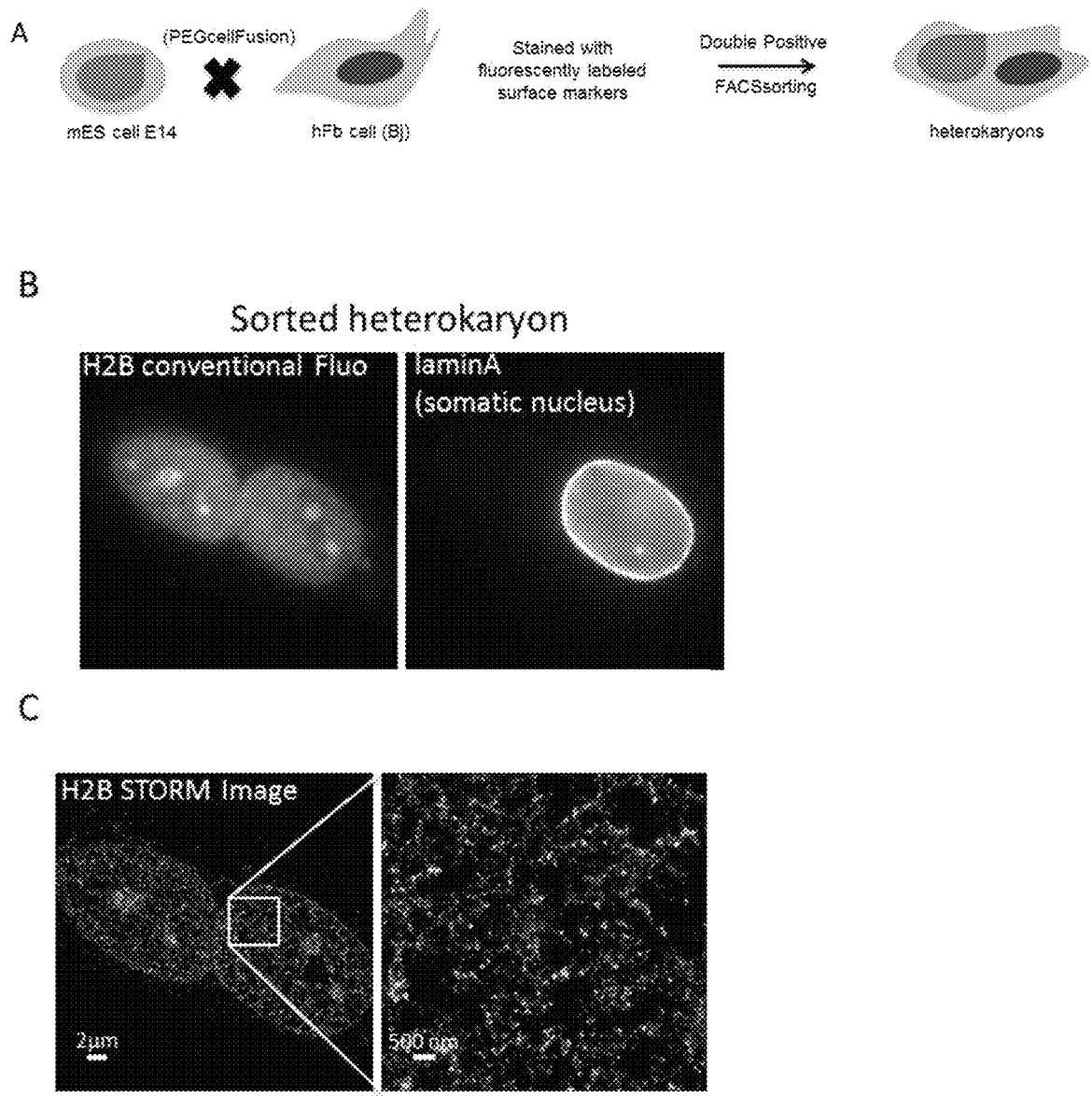
FIG. 13: (A) Experimental procedure. (B) Conventional image of histone H2B in the two nuclei of a fused cell. Lamin A is used as a marker to distinguish the human fibroblast nucleus from the mESC nucleus. mESC nucleus does not express lamin A. (C) STORM image of histone H2B in the two nuclei of a fused cell. (D) Quantification of clutch size in the two nuclei 7 hours and 24 hours after fusion.
Figure 13:
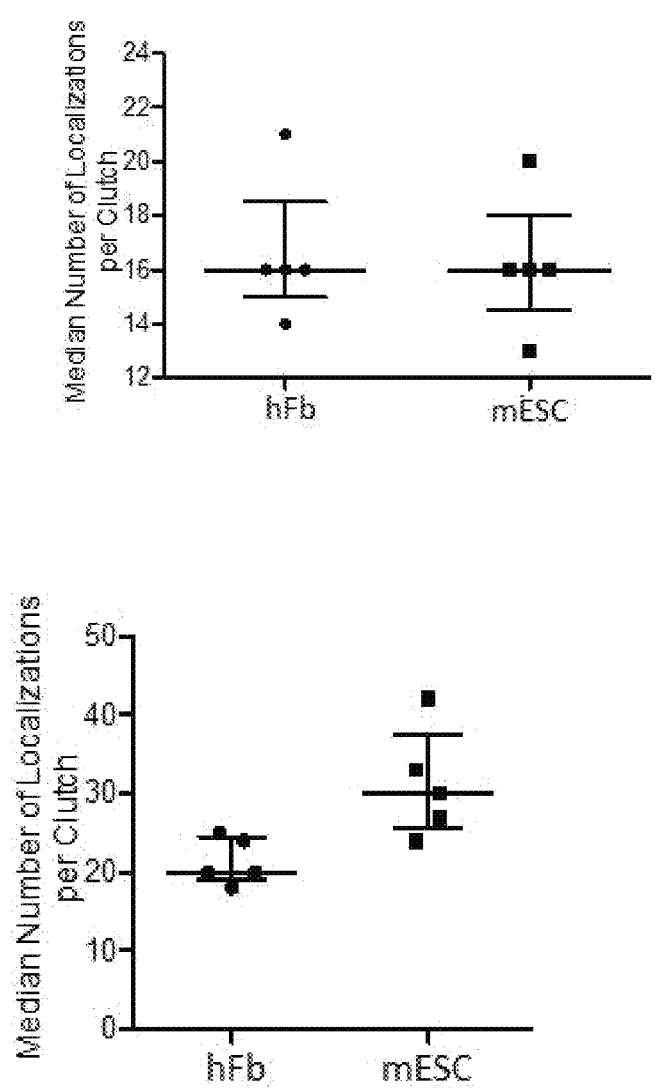

The results demonstrate changes in the chromatin state of both the somatic human fibroblast and the mESC nuclei (see FIG. 13) Thus, fusion change the chromatin state.

REFERENCES

Bates, M., Huang, B., Dempsey, G. T., and Zhuang, X. (2007). Multicolor super-resolution imaging with photoswitchable fluorescent probes. Science 317, 1749-1753.
Bibel, M., Richter, J., Lacroix, E., and Barde, Y. A. (2007). Generation of a defined and uniform population of CNS progenitors and neurons from mouse embryonic stem cells. Nature protocols 2, 1034-1043.
Bock, C., Kiskinis, E., Verstappen, G., Gu, H., Boulting, G., Smith, Z. D., Ziller, M., Croft, G. F., Amoroso, M. W., Oakley, D. H., et al. (2011). Reference Maps of human ES and iPS cell variation enable high-throughput characterization of pluripotent cell lines. Cell 144, 439-452.
Dani, A., Huang, B., Bergan, J., Dulac, C., and Zhuang, X. (2010). Superresolution imaging of chemical synapses in the brain. Neuron 68, 843-856.
Fan, Y., Nikitina, T., Zhao, J., Fleury, T. J., Bhattacharyya, R., Bouhassira, E. E., Stein, A., Woodcock, C. L., and Skoultchi, A. I. (2005). Histone H1 depletion in mammals alters global chromatin structure but causes specific changes in gene regulation. Cell 123, 1199-1212.
Fussner, E., Ching, R. W., and Bazett-Jones, D. P. (2011a). Living without 30 nm chromatin fibers. Trends in biochemical sciences 36, 1-6.
Fussner, E., Djuric, U., Strauss, M., Hotta, A., Perez-Iratxeta, C., Lanner, F., Dilworth, F. J., Ellis, J., and Bazett-Jones, D. P. (2011b). Constitutive heterochromatin reorganization during somatic cell reprogramming. The EMBO journal 30, 1778-1789.
Grigoryev, S. A., Arya, G., Correll, S., Woodcock, C. L., and Schlick, T. (2009). Evidence for heteromorphic chromatin fibers from analysis of nucleosome interactions. Proceedings of the National Academy of Sciences of the United States of America 106, 13317-13322.
Huang, B., Jones, S. A., Brandenburg, B., and Zhuang, X. (2008a). Whole-cell 3D STORM reveals interactions between cellular structures with nanometer-scale resolution. Nature methods 5, 1047-1052.
Huang, B., Wang, W., Bates, M., and Zhuang, X. (2008b). Three-dimensional super-resolution imaging by stochastic optical reconstruction microscopy. Science 319, 810-813.
Kornberg, R. D., and Lorch, Y. (1999). Twenty-five years of the nucleosome, fundamental particle of the eukaryote chromosome. Cell 98, 285-294.
Kuhl, S. J., and Kuhl, M. (2013). On the role of Wnt/beta-catenin signaling in stem cells. Biochimica et biophysica acta 1830, 2297-2306.
Marks, H., Kalkan, T., Menafra, R., Denissov, S., Jones, K., Hofemeister, H., Nichols, J., Kranz, A., Stewart, A. F., Smith, A., et al. (2012). The transcriptional and epigenomic foundations of ground state pluripotency. Cell 149, 590-604.
Meshorer, E., Yellajoshula, D., George, E., Scambler, P. J., Brown, D. T., and Misteli, T. (2006). Hyperdynamic plasticity of chromatin proteins in pluripotent embryonic stem cells. Developmental cell 10, 105-116.
Nieuwenhuizen, R. P., Lidke, K. A., Bates, M., Puig, D. L., Grunwald, D., Stallinga, S., and Rieger, B. (2013). Measuring image resolution in optical nanoscopy. Nature methods 10, 557-562.
Ying, Q. L., Wray, J., Nichols, J., Batlle-Morera, L., Doble, B., Woodgett, J., Cohen, P., and Smith, A. (2008). The ground state of embryonic stem cell self-renewal. Nature 453, 519-523.
Pereira C Fl, Terranova R, Ryan N K, Santos J, Morris K J, Cui W, Merkenschlager M, Fisher A G (2008) Heterokaryon-based reprogramming of human B lymphocytes for pluripotency requires Oct4 but not Sox2. PLoS Genet. September 5; 4(9):e1000170.
Rust, M. J., Bates, M., and Zhuang, X. (2006). Sub-diffraction-limit imaging by stochastic optical reconstruction microscopy (STORM). Nature methods 3, 793-795.
Struhl, K., and Segal, E. (2013). Determinants of nucleosome positioning. Nature structural & molecular biology 20, 267-273.
Toth, K. F., Knoch, T. A., Wachsmuth, M., Frank-Stohr, M., Stohr, M., Bacher, C. P., Muller, G., and Rippe, K. (2004).

Trichostatin A-induced histone acetylation causes decondensation of interphase chromatin. Journal of cell science 117, 4277-4287.

Woodcock, C. L., and Ghosh, R. P. (2010). Chromatin higher-order structure and dynamics. Cold Spring Harbor perspectives in biology 2, a000596.

Yi, F., Pereira, L., and Merrill, B. J. (2008). Tcf3 functions as a steady-state limiter of transcriptional programs of mouse embryonic stem cell self-renewal. Stem cells 26, 1951-1960.

The invention claimed is:

1. Method for detecting the chromatin state of a cell comprising
  a) contacting a sample containing cells previously fixed and permeabilized with a first antibody capable of specifically binding to a histone protein,
  b) contacting the antibody:histone complex formed in step a) with a secondary antibody having at least one photoswitchable fluorophore adapted to be optically excited at a certain wavelength $\lambda_1$ and to emit light at a wavelength $\lambda_2$ different from $\lambda_1$,
  c) recording a super resolution image of nucleosome organization by means of a sensor being sensitive at least to the wavelength of emission of the photoswitchable fluorophore by exciting the sample with an optical radiation having a wavelength $\lambda_1$,
  d) correlating the image obtained in step c) with size of nucleosomal clutches, the number of nucleosomes in a clutch per the area of that clutch and/or number of nucleosomes per nucleosomal clutches, and
  e) comparing data obtained in step d) with a corresponding reference value to obtain a score based on size of nucleosomal clutches, the number of nucleosomes in a clutch per the area of that clutch and/or number of nucleosomes per nucleosomal clutch,
wherein a cell comprising smaller clutches, less number of nucleosomes in a clutch per the area of that clutch or less nucleosomes per clutches compared to the corresponding reference value indicates that said cell is in an open chromatin state and wherein a cell comprising bigger clutches, more number of nucleosomes in a clutch per the area of that clutch or more nucleosomes per clutches compared to the corresponding reference value indicates that said cell is in a closed chromatin state.

2. The method according to claim 1, wherein the cell in an open chromatin state is selected from the group consisting of a transcriptionally active cell, a pluripotent stem cell, a cancer cell, a drug perturbed cell and a reprogrammed cell.

3. The method according to claim 1, wherein the secondary antibody further comprises a second fluorophore adapted to be optically excited at a wavelength $\lambda_3$ and reactivate the first fluorophore by bringing it from its dark state back to its ground state, upon which the first fluorophore can be excited again at its excitation wavelength $\lambda_1$ and emit light at its emission wavelength $\lambda_2$.

4. The method according to claim 3, wherein a plurality of super resolution images are taken by means of the sensor being also sensitive at least to the wavelength of emission of the second fluorophore $\lambda_2$ rendering a further super resolution image by collecting the sensed light emissions recorded in the plurality of images.

5. The method according to claim 4, wherein, before recording each super resolution image of the plurality of super resolution images, the sample is excited one or more times with an optical radiation having a wavelength $\lambda_1$ and subsequently excited one or more times with an optical radiation having a wavelength $\lambda_3$.

6. The method according to claim 4, wherein the super resolution image is rendered from a list of locations with x and v coordinates in the sample where an optical emission of a photoswitchable fluorophore adapted to emit light at a wavelength $\lambda_2$ is present.

7. The method according to claim 6, wherein
  a density image of resolution lower than or equal to the rendered high resolution image and representing the same area as said rendered high resolution image is provided wherein each pixel of the density image has a value proportional to the number of locations of the location list falling within the area represented by said pixel,
  a binary image representing the same area as the density image comprising zero value pixels if the corresponding value represented by the density image in the same location is lower than a predefined threshold; and, nonzero if said value is higher, is provided,
  identifying connected regions of pixels representing values higher than the predefined threshold,
  for each connected region, providing a list of clutch positions by grouping the localization coordinates within said connected region according to a distance-based criterion being the position of the clutch the centroid position of the localization coordinates associated with said clutch.

8. The method according to claim 7, wherein the size of each clutch is calculated as a measure of the spreading of the positions of all the localization coordinates associated with said clutch and/or the number of nucleosomes within said clutch.

9. The method according to claim 7, wherein the density of nucleosomes within a clutch calculated as the number of nucleosomes within that clutch divided by the area occupied by said clutch.

10. The method according to claim 3, wherein the power of the optical radiation having a wavelength $\lambda_3$ is monotonically increased.

11. The method according to claim 1, wherein the histone protein is H2B.

12. A method for isolating a cell in an open chromatin state comprising
  a) detecting the chromatin state of a cell by a method according to claim 1, and
  b) isolating a cell having smaller clutches, less number of nucleosomes in a clutch per the area of that clutch or less nucleosomes per clutches.

13. The method for isolating a cell in an open chromatin state according to claim 12, wherein the cell in an open chromatin state is selected from the group consisting of a transcriptionally active cell, a pluripotent cell, a cancer cell, a drug-perturbed cell and a reprogrammed cell.

14. A method for isolating a cell in a closed chromatin state
  a) detecting the chromatin state of the cell by a method according to claim 1, and
  b) isolating a cell having bigger clutches, more number of nucleosomes in a clutch per the area of that clutch or more nucleosomes per clutches.

15. A method for detecting the chromatin state of a cell and isolating a cell in an open chromatin state or in a closed chromatin state, said method comprising using a kit comprising a first antibody capable of specifically binding to a histone protein and a photoswitchable fluorophore linked-secondary antibody, the method comprising a) contacting a sample containing cells previously fixed and permeabilized with a first antibody capable of specifically binding to a histone protein,
b) contacting the antibody:histone complex formed in step a) with a secondary antibody having at least one photoswitchable fluorophore adapted to be optically excited at a certain wavelength $\lambda_1$ and to emit light at a wavelength $\lambda_2$ different from $\lambda_1$,
c) recording a super resolution image of nucleosome organization by means of a sensor being sensitive at least to the wavelength of emission of the photoswitchable fluorophore by exciting the sample with an optical radiation having a wavelength $\lambda_1$,
d) correlating the image obtained in step c) with size of nucleosomal clutches, the number of nucleosomes in a clutch per area of that clutch and/or number of nucleosomes per nucleosomal clutches, and
e) comparing data obtained in step d) with a corresponding reference value to obtain a score based on size of nucleosomal clutches, the number of nucleosomes in a clutch divided by the area of that clutch and/or number of nucleosomes per nucleosomal clutch, and
f) isolating a cell in an open chromatin state having smaller clutches, less number of nucleosomes in a clutch per the area of that clutch or less nucleosomes per clutches compared to the corresponding reference value or isolating a cell in a closed chromatin state having bigger clutches, more number of nucleosomes in a clutch per area of that clutch or more nucleosomes per clutches compared to the corresponding reference value.

* * * * *

UNITED STATES PATENT AND TRADEMARK OFFICE
CERTIFICATE OF CORRECTION

PATENT NO. : 10,564,167 B2
APPLICATION NO. : 15/510082
DATED : February 18, 2020
INVENTOR(S) : Melike Lakadamyali et al.

Page 1 of 1

It is certified that error appears in the above-identified patent and that said Letters Patent is hereby corrected as shown below:

On the Title Page

Item (71) Applicants:
INSTITUCIÓ CATALANA DE RECERCA I ESTUDIS AVANçATS
Should read:
INSTITUCIÓ CATALANA DE RECERCA I ESTUDIS AVANÇATS Item (73) Assignees:
FUNDACIÓ INSTITUT DE CIÈNCIES FOTÒNEQUES
Should read:
FUNDACIÓ INSTITUT DE CIÈNCIES FOTÒNIQUES Item (73) Assignees:
INSTITUCIÓ CATALANA DE RECERCA ↑ ESTUDIS AVANçATS
Should Read:
INSTITUCIÓ CATALANA DE RECERCA I ESTUDIS AVANÇATS In the Claims Claim 6, Column 44, Line 3:
and v coordinates in the sample where an optical emission
Should read:
and y coordinates in the sample where an optical emission Claim 10, Column 44, Line 36:
10. The method according to claim 3, wherein the power
Should read:
10. The method according to claim 3, wherein power Signed and Sealed this
Twenty-eighth Day of July, 2020

Andrei Iancu
*Director of the United States Patent and Trademark Office*